US008927255B2

(12) United States Patent
Calvo-Byrd et al.

(10) Patent No.: US 8,927,255 B2
(45) Date of Patent: Jan. 6, 2015

(54) EFFECTS OF ALTERATION OF EXPRESSION OF THE MTFA GENE AND ITS HOMOLOGS ON THE PRODUCTION OF FUNGAL SECONDARY METABOLITES

(71) Applicant: Board of Trustees of Northern Illinois University, Dekalb, IL (US)

(72) Inventors: Ana M. Calvo-Byrd, Dekalb, IL (US); Vellaisamy Ramamoorthy, Dekalb, IL (US)

(73) Assignee: Board of Trustees of Northern Illnois University, DeKalk, IL (US)

( * ) Notice: Subject to any disclaimer, the term of this patent is extended or adjusted under 35 U.S.C. 154(b) by 0 days.

(21) Appl. No.: 14/070,094

(22) Filed: Nov. 1, 2013

(65) Prior Publication Data

US 2014/0134742 A1 May 15, 2014

Related U.S. Application Data

(60) Provisional application No. 61/721,777, filed on Nov. 2, 2012.

(51) Int. Cl.
*C12N 15/80* (2006.01)
*C12N 1/14* (2006.01)
*C07K 14/37* (2006.01)
*C12P 37/00* (2006.01)

(52) U.S. Cl.
CPC . *C12N 1/14* (2013.01); *C07K 14/37* (2013.01); *C12P 37/00* (2013.01)
USPC ................ 435/254.11; 435/320.1; 435/254.3; 435/69.1; 435/477; 435/375

(58) Field of Classification Search
None
See application file for complete search history.

(56) References Cited

PUBLICATIONS

Barrios-Gonzalez et al., "Penicillin Production by Solid State Fermentation", *Biotechnology Letters*, 10(11): 793-798 (1988).

Brown et al., "Twenty-five coregulated transcripts define a sterigmatocystin gene cluster in *Aspergillus nidulans", Proc. Natl. Acad. Sci. USA*, 93: 1418-1422 (1996).

Calvo et al., "veA is Required for Toxin and Sclerotial Production in *Aspergillus parasiticus", Applied & Environmental Microbiology*, 70(8): 4733-4739 (2004).

Calvo, "The VeA regulatory system and its role in morphological and checmical development in fungi" *Fungal Genetics and Biology*, 45: 1053-1061 (2008).

Cole et al., *Handbook of Toxic Fungal Metabolites*, Academic Press, Chap. 1-2, 18 (1981).

Duran et al., "Production of cyclopiazonic acid, alfatrem, and aflatoxin by *Aspergillus flavus* is regulated by veA, a gene necessary for sclerotial formation", *Applied Microbiology and Biotechnology*, 73: 1158-1168 (2007).

Fernandez-Canon, "Overexpression of two penicillin structural genes in *Aspergillus nidulans", Molecular and General Genetics MGG*, 246(1): 110-118 (1995).

Käfer, "Meiotic and Mitotic Recombination in *Aspergillus* and its Chromosomal Aberrations," *Advance in Genetics*, vol. 19, Ed. E.W. Caspari, Academic Press, pp. 33-131 (1977).

Kato et al., "The Expression of Sterigmatocystin and Penicillin Genes in *Aspergillus nidulans* is Controlled by veA, a Gene Required for Sexual Development", *Eukaryotic Cell*, 2(6): 1178-1186 (2003).

Keil et al., "Overproduction of a single protein, Pc-Pex11p, results in 2-fold enhanced penicililin production by *Penicillin chrysogenum", Fungal Genetics and Biology*, 42: 154-164 (2005).

Keller et al., "Metabolic Pathway Gene Clusters in Filamentous Fungi", *Fungal Genetics and Biology*, 21: 17-29 (1997).

Kim et al., "The veA gene activates sexual development in *Aspergillus nidulans", Fungal Genetics and Biology*, 37: 72-80 (2002).

Miller et al., "Direct and indirect gene replacements in *Aspergillus nidulans", Molecular and Cellular Biology*, 5(7): 1714-1721 (1985).

Miller et al., "Position-dependent and—independent mechanisms regulate cell-specific expression of the SpoC1 gene cluster of *Aspergillus nidulans", Molecular and Cellular Biology*, 7(1): 427-434 (1987).

Myung et al., "FvVE1 Regulates Biosynthesis of Fumonisins and Fusarins in *Fusarium verticillioides", Journal of Agricultural and Food Chemistry*, 57: 5089-5094 (2009).

Osherov et al., "Conidial Germination in *Aspergillus nidulans* Requires RAS Signaling and Protein Synthesis", *Genetics*, 155: 647-656 (2000).

Pontecorvo, "The Genetics of *Aspergillus nidulans", Advances in Genetics*, 5: 141-238 (1953).

Ramamoorthy et al., "veA-dependent RNA-pol II transcription elongation factor-like protein, RtfA, is associated with secondary metabolism and morphological development in *Aspergillus nidulans", Molecular Microbiology*, 84(4): 795-814 (2012).

Ramamoorthy et al. "The Putative C2H2 Transcription Factor MtfA is a Novel Regulator of Secondary Metabolism and Morphogenesis in *Aspergillus nidulans", Plos One*, 8(9): 1-16 (2013).

Sambrook et al., "Molecular Cloning, A Laboratory Manual," 3rd Ed., vol. 2, Chap. 1, 5-8 (2001).

Yelton et al., "Developmental regulation of the *Aspergillus nidulans* trpC gene", *Proceedings of the National Academy of Sciences*, 80: 7576-7580 (1983).

Yu et al., "Conservation of structure and function of the aflatoxin regulatory gene *aflR* from *Aspergillus nidulans* and *A. flavus", Current Genetics*, 29: 549-555 (1996).

*Primary Examiner* — Jim Ketter

(74) *Attorney, Agent, or Firm* — Barnes & Thornburg LLP; Alice O. Martin

(57) ABSTRACT

Many fungal secondary metabolites are of industrial interest, such as antibiotics, while others are undesirable compounds such as mycotoxins. Overexpression of mtfA enhances production of fungal compounds with applications in the medical field, and overexpression or impaired mtfA expression decreases the production of compounds that negatively affect health/agriculture/economy such as mycotoxins.

10 Claims, 12 Drawing Sheets

A

1kb

AN8741.2

AN8740.2

Mdlanlisqpgpepaltaksrysppafepgsfyaastsftrtqaplsppvedrssrcslpsisal
ldsadgastqapkrqrlsspmhrepldknpsagaapirlpptpplrpgsgfhsaghspsssi
ssismikseypappsapvslpglpsptdrssissqgsapqhqhgpyaspapsvapsysspv
epspssamyyqhqrpassgtyqappppphqpmispvtpawqhhhyfppssntpyq $C_2H_2$ zinc finger domain qnhdryi C-r-t-C-h-k-a-f-s-r-p-s-s-l-r-i-h-s-h-s-h-t-g-e-k-p-f-r-C-t-h-a-

$C_2H_2$ zinc finger domain g-C-g-k-a-f-s-v-r-s-n-m-k-r-h-e-r-g-c-h-t-g-r-a-v-a-m-v

B

```
Ate   1 MDLASLIT-PGPTPFASRP-PRASYSPPASSSGSYKAPNEPHYTGSYFPAMPTATPVTTT
Afl   1 MDLASLIT-PGPEPIYKS---RASYSPPPSSAGSYKRPAE---HDSYF------------
Acl   1 MDLANLIS-HPTSEAASTFKSRSAQSPPAFQANPYKRLSGSS-MSSYFTSVP-----TTA
Afu   1 MDVASLIS-PSESDTVPTFRSRSIQNS---SASHYKRLSEQS-TGSYFSAVP-----THT
Ani   1 MDLANLISQPGPEPALTA---KSRYSPPAFEPGSFYAAST-------------------

Ate  59 TSYSRSPQPPLSPPVEDQP-KCSLPSISTLLGAADSAPMPPAKRQRLSTPARRESDSWL
Afl  42 -SYSRAPQAPLSPPVEDQP-KCSLPSISTLLEGADSASTYAAKRQRTSPPPRRESEFRS
Acl  54 TSYSRTPQPPLSPPVDDRP-RCSLPSISTLLEGADSAAAHAAKRQRTSLSAHRDLDARP
Afu  51 TSYSRTPQPPLSPPAEDQS-KCSLPSISILLENADGAAAHAAKRQRNSLSTHRDSDPRP
Ani  38 -SFTRT-QAPLSPPVEDRSSRCSLPSISALLDSADGASTQAPKRQRLSSPMHREPLDKN

Ate 117 Q-------TTPCLPPTPPLRPGSGFHSSGHRSPSSNKPTESAPFP-------QQPPVTLP
Afl  99 PY---DSVSTPNGPPTPPLRPESGFHS-GHHSPSASSVTSGKAIKLE---SYSQTPMTLP
Acl 112 QSQPYDTITPHALPPTPPLRPGSGFRSNGHSPSASSVSATSASTVIK-TETYPQPHIGLP
Afu 109 ---PYDSITPHAMPPTPPLRPGSGFHSNGHSPSTSSVSAASSSALMKNTESYPQAPIGLP
Ani  95 PS---AGAAPIRLPPTPPLRPGSGFHSAGHSPSSSISSISMIKSEYPAPPSAPVSLPGLP

Ate 163 SPTERSSISSQGSAH----APYASPAPSVA-SYSSPVEPSPAPSTLYYQR-------PAA
Afl 152 SPSDRSSISSQGSVHHVSAAPYASPAPSVA-SYSSPVESS-APSAMYYQRPSGSYQTPAT
Acl 171 SPTDRSSISSQGSVQHAPGAPYASPAPSVA-SYSSPVEPSTPSSAAYYQRKA----PSAP
Afu 166 SPTDRSSISSQGSVQHAASAPYASPAPSVS-SFSSPIEPSTPSTAAYYQRNP----APNT
Ani 152 SPTDRSSISSQGSAPQHQHGPYASPAPSVAPSYSSPVEPS-PSSAMYYQHQR--------

Ate 211 PPAPSAA-AAAPAP-----AQPLISPVTPAWQHHHYFPPSSSTPYQQNHDRYICRTCHKA
Afl 210 VPSPSAAPMPASAT-----HQQMTPVTPAWQHHHYFPPSSSAPYQQNHDRYICRTCHKA
Acl 226 FQNPGSVPSASAA------HQQLITPITPAWQHHHYFPPSSSTAYQQNHDRYICRTCHKA
Afu 221 FQNPSPFPQTSTASLPSPGHQQMISPVTPAWQHHHYFPPSSSTSYQQNHDRYICRTCHKA
Ani 203 PASSGTYQAPPPPPQ----HQPMISPVTPAWQHHHYFPPSSNTPYQQNHDRYICRTCHKA

Ate 265 FSRPSSLRIHSHSHTGEKPFRCTHAGCGKAFSVRSNMKRHERGCHSGRPVATAMV-
Afl 265 FSRPSSLRIHSHSHTGEKPFRCTHAGCGKAFSVRSNMKRHERGCHTGRPVATAMV-
Acl 280 FSRPSSLRIHSHSHTGEKPFRCTHAGCGKAFSVRSNMKRHERGCHTGRPVATAMVS
Afu 281 FSRPSSLRIHSHSHTGEKPFRCTHAGCGKAFSVRSNMKRHERGCHTGRPVATAMVQ
Ani 259 FSRPSSLRIHSHSHTGEKPFRCTHAGCGKAFSVRSNMKRHERGCHTGR--AVAMV-
```

$C_2H_2$ zinc finger domain $C_2H_2$ zinc finger domain

FIG. 2

EFFECTS OF ALTERATION OF EXPRESSION OF THE MTFA GENE AND ITS HOMOLOGS ON THE PRODUCTION OF FUNGAL SECONDARY METABOLITES

CROSS REFERENCE TO RELATED APPLICATIONS

This application claims priority from U.S. provisional application No. 61/721,777, filed Nov. 2, 2012, the content of which is herein incorporated by reference in its entirety.

SEQUENCE LISTING

The instant application contains a Sequence Listing which has been submitted electronically in ASCII format and is hereby incorporated as part of the application. Said ASCII copy, created on Jan. 20, 2014, is named 702289_SEQ-ST25.txt and is 111,626 bytes in size.

The United States Government has rights in this invention pursuant to Contract No. NIH R15AI081232 between the United States Government and The Board of Trustees of Northern Illinois University.

BACKGROUND

Many fungal secondary metabolites are of industrial interest, such as antibiotics, while others are undesirable compounds such as mycotoxins. Overexpression of mtfA enhances production of fungal compounds with applications in the medical field, and overexpression or impaired mtfA expression decreases the production of compounds that negatively affect health/agriculture/economy such as mycotoxins.

Numerous fungal secondary metabolites, also denominated natural products, have beneficial biological activities that can be use in the medical field, including antibiotics and antitumoral drugs among others.

Other fungal natural products, such as mycotoxin, are detrimental for human and animal health and negatively impact agriculture causing economic losses.

Species of the genus *Aspergillus* produce numerous secondary metabolites (Adrio and Demain, 2003; Reverberi et al., 2010; Brakhage and Schroeckh, 2011), including compounds with beneficial effects, such as antibiotics and other molecules with application in the medical field. Other secondary metabolites produce by these organisms are detrimental, such as mycotoxins (Bennett and Klich, 2003). *Aspergillus nidulans*, a model filamentous fungus studied for more than fifty years, produces the mycotoxin sterigmatocystin (ST). ST and the carcinogenic compounds called aflatoxins (AF), produced by related species such as *A. flavus, A. parasiticus*, and *A. nomiusi* (Cole and Cox, 1981), are both synthesized through a conserved metabolic pathway (Payne and Yu, 2010; Sweeney and Dobson, 1999; Payne and Brown, 1998) where ST is the penultimate precursor. The genes responsible for ST/AF biosynthesis are clustered. Within the clusters, the regulatory gene aflR encodes a transcription factor that acts as a specific cluster activator (Keller and Hohn, 1997; Yu et al., 1996; Fernandes et al., 1998).

*Aspergillus nidulans* also produces the beta-lactam antibiotic penicillin and the antitumoral compound terraquinone.

In fungi secondary metabolism regulation and is often found to be govern by genetic mechanisms also controlling asexual and sexual development (Calvo et al., 2002). One of this main common regulatory links is the global regulatory gene veA, first described to be a developmental regulator in *A. nidulans* (Kim et al., 2002). In 2003 we describe for the first time the connection between veA and the synthesis of numerous secondary metabolites, including ST (Kato et al., 2003). Absence of the veA gene in *A. nidulans* prevents aflR expression and ST biosynthesis. VeA also regulates the production of other metabolites, including penicillin (Kato et al., 2003). In other fungi, veA homologs also regulate the synthesis of penicillin in *Penicillium chrysogenum* (Hoff et al., 2010) as well as cephalosporin C in *Acremonium chrysogenum* (Dreyer et al., 2007). Furthermore, veA also regulates the biosynthesis of other mycotoxins, for example AF, cyclopiazonic acid and aflatrem in *Aspergillus flavus* (Duran et al., 2007; Calvo et al., 2004; Duran et al., 2009), trichothecenes in *F. graminerum* (Merhej et al., 2011), and fumonisins and fusarins in *Fusarium* spp, including *F. verticillioides* and *F. fujikuroi* (Myung et al., 2011; Niermann et al., 2011).

veA is extensively conserved in *Ascomycetes* (Myung et al., 2011). Most of the studies on the veA regulatory mechanism of action have been carried out using the model fungus *A. nidulans*. It is known that KapA α-importin transport the VeA protein to the nucleus, particularly in the dark, a condition that favors ST production (Stinnett et al., 2007, Araujo-Bazan et al., 2009). In the nucleus, VeA interacts with several proteins such as the light-responsive protein FphA, which interacts with the LreA-LreB. FphA, LreA and LreB also have influence fungal development and mycotoxin production (Purschwitz et al., 2008). While FphA negatively regulates sexual development and the synthesis of ST, the LreA and LreB proteins play the opposite role. In the nucleus VeA also interacts with VelB and LaeA (Bayram et al., 2008; Calvo, 2008; Bayram and Braus, 2012). LaeA, a chromatin-modifying protein is also required for the synthesis of ST and other secondary metabolites (Reyes-Dominguez et al., 2007; Bok and Keller, 2004). Deletion of velB decreases and delayed ST production, indicating a positive role in ST biosynthesis (Bayram et al., 2008; Bayram and Braus, 2012).

In addition to its role as global regulator of development and secondary metabolism, VeA is also require for normal plant pathogenicity by several mycotoxigenic species, such as *A. flavus* (Duran et al., 2009), *F. verticillioides* (Myung et al., 2012), *F. fujikuroi* (Wiemann et al., 2010), and *F. graminearum* (Merhej et al., 2011). Deletion of veA homologs in these organisms results in a decrease in virulence with a reduction in mycotoxin biosynthesis.

SUMMARY

Over-expression of the fungal transcription factor encoding gene, mtfA (master transcription factor A), located in nuclei of fungal cells leads to an increase in production of penicillin and a decrease in mycotoxin production. Elimination of this gene also leads to decrease in mycotoxin.

For the first time overexpression of mtfA is shown to increase penicillin production and decrease mycotoxin production in the model fungus *Aspergillus nidulans*. Variations in the expression of mtfA also affect the synthesis of other secondary metabolites. Deletion of mtfA in the model fungus *Aspergillus nidulans* also decreases or eliminates sterigmatocystin production.

Manipulations to alter the expression of the fungal mtfA gene increase the production of both beneficial fungal secondary metabolites, such as penicillin G, and decrease the production of those secondary metabolites that are detrimental, such as aflatoxin-related mycotoxins.

An application is to increase the production of valuable fungal secondary metabolites and decrease the production of detrimental fungal secondary metabolites in fungal cells.

Increase of beneficial fungal secondary metabolites and decrease of detrimental fungal secondary metabolites is achieved by alteration of the expression of the gene mtfA in cells.

Secondary metabolism in the model fungus *Aspergillus nidulans* is controlled by the global conserved regulator VeA, which also governs morphological differentiation. Among the secondary metabolites regulated by VeA is the mycotoxin sterigmatocystin (ST). The presence of VeA is necessary for the biosynthesis of this carcinogenic compound. A revertant mutant was identified that able to synthesize ST in the absence of VeA. The point mutation occurred at the coding region of a gene encoding a novel putative C2H2 zinc finger domain type transcription factor denominated as mtfA (master transcription factor). The *A. nidulans* mtfA gene product localized at nuclei independently of the illumination regime. Deletion of the mtfA gene restored mycotoxin biosynthesis in the absence of veA, but drastically reduced mycotoxin production when mtfA gene expression was altered, by deletion or overexpression, in the *Aspergillus nidulans* strains with a veA wild type allele. mtfA regulates ST production by controlling the expression of the specific ST gene cluster activator aflR. Importantly, mtfA is also a regulator of other secondary metabolism gene clusters and natural product biosynthesis, such as genes involved in terraquinone production and penicillin biosynthesis. As in the case of ST, deletion or overexpression of mtfA was also detrimental for the expression of terraquinone genes. However, production of penicillin was increased more than 25% by overexpressing mtfA. Furthemore, in addition to its effect on secondary metabolism, mtfA controls sexual and asexual development in *A. nidulans*. Deletion of mtfA results in a reduction of conidiation and sexual development. mtfA putative orthologs conserved in other fungal species are also disclosed.

In summary, deletion of mtfA in a deletion veA genetic background increases ST toxin production; deletion or overexpression of mtfA in a wild type (veA+) genetic background results in a reduction of ST (Because mtfA is not found in plant or animals, mtfA could be used as a genetic target to prevent or reduce toxin production and possible the production of other secondary metabolites); deletion or over-expression of mtfA in a wild type (veA+) genetic background results in a decrease in the expression of terraquinone genes; deletion of mtfA in a wild type (veA+) genetic background results in a decrease in penicillin production; and deletion of mtfA leads to a reduction of sexual and asexual development in fungus.

Overexpression of mtfA in a wild type (veA+) genetic background results in an increase (more than 25% increase) in penicillin production. Other fungi, including *Penicillium chrysogenum*, contain a mtfA ortholog. Manipulation of mtfA leads to an increase in penicillin production in *A. nidulans.*

The RM7 gene and MtfA gene are the same gene. RM7's initial name was renamed mtfA based on the *Aspergillus nidulans* nomenclature, but they are the same sequence. The accession number and the coding region of the *Aspergillus nidulans* mtfA gene in the disclosure is: accession number ANID_08741 sequence (SEQ ID NO: 1):

```
ATGGATCTCGCCAACCTCATCTCCCAACCGGGGCCTGAGCCTGCTCTGAC

GGCCAAATCAAGATACAGCCCTCCTGCCTTTGAACCGGGCTCCTTCTACG

CCGCATCTACTTCATTCACGCGGACACAAGCGCCACTATCGCCTCCAGTC
```

-continued

```
GAGGATAGATCTTCTCGCTGCTCACTGCCATCAATCTCTGCGCTTCTTGA

CAGCGCAGACGGCGCCTCGACACAAGCTCCAAAGCGCCAACGGCTCAGCT

CTCCAATGCACCGTGAACCGCTTGACAAGAACCCATCTGCCGGCGCTGCT

CCCATCCGTCTCCCGCCCACTCCTCCATTGCGCCCCGGCTCCGGCTTCCA

CAGCGCCGGCCACTCGCCCTCGAGCTCCATCTCATCCATCTCGATGATCA

AGTCCGAGTACCCGGCACCACCATCAGCTCCAGTCTCTCTTCCGGGCCTT

CCCAGCCCAACCGACCGCTCGTCCATCTCGAGCCAAGGGTCTGCGCCGCA

GCACCAGCATGGTCCCTACGCCTCGCCAGCTCCCAGCGTGGCGCCCTCTT

ACTCCTCGCCCGTTGAGCCCTCACCCTCATCGGCAATGTACTACCAACAC

CAGCGGCCCGCATCCTCAGGCACATACCAGGCTCCTCCACCCCCGCCGCA

ACACCAGCCCATGATCTCGCCCGTGACACCGGCCTGGCAGCACCACCACT

ACTTCCCTCCTTCCTCAAACACACCCTACCAGCAGAACCACGACCGATAT

ATCTGCCGCACCTGCCACAAGGCGTTCTCGCGGCCCTCGAGTCTGCGCAT

CCACAGCCATAGCCACACCGGCGAGAAGCCATTTCGGTGCACACATGCCG

GATGCGGCAAAGCCTTTAGTGTACGGAGCAACATGAAGCGCCATGAGCGC

GGCTGCCATACCGGGAGGGCTGTCGCGATGGTGTAA
```

BRIEF DESCRIPTION OF THE DRAWINGS

FIG. 2 RM7 mutant has single gene mutation at locus AN8741.2 Map of mtfA gene. Two solid horizontal arrows indicate the two coding regions in the genome fragment of the genomic library plasmid pRG3-AMA-NOT1 that complement the RM7-R2: The coding regions are locus AN8741.2 encoding a putative C2H2 zinc finger domain transcription factor and locus AN8741.2 encoding a hypothetical proteins. Sequencing of the corresponding region in the RM7 revealed that mutation occurred at Locus AN8741.2 designated as mtfA gene. Vertical arrow indicates mutated amino acid in putative C2H2 zinc finger domain containing protein as result of point mutation at start codon (ATG to ATT resulting change of methonine to isoleucine). The protein sequence contains two zinc finger domains represented in lines. Sequence alignment. The amino acid alignment of mtfA gene of *A. nidulans* (Ani) with putative homologues of *A. terreus* (Ate), *A. flavus* (Afl), *A. clavatus* (Acl) and *A. fumigates* (Afu) were analyzed using ClusterW (http://www.ebi.ac.uk/Tools/clustalw2/index.htm) land boxshade (http://www.ch.embnet.org/software/BOX_form.html) multiple sequence alignment software programs. MtfA of *A. nidulans* and its homologs having C2H2 zinc finger domain are underlined. Upward arrow indicates the amino acid metheonine at the position first amino acid of MtfA is converted to isoleucine and protein synthesis could have started using the next methonine as a start codon.

FIG. 2A discloses SEQ ID NO: 45 and FIG. 2B discloses SEQ ID NOS 46-49 and 45, respectively, in order of appearance.

Figure 4:
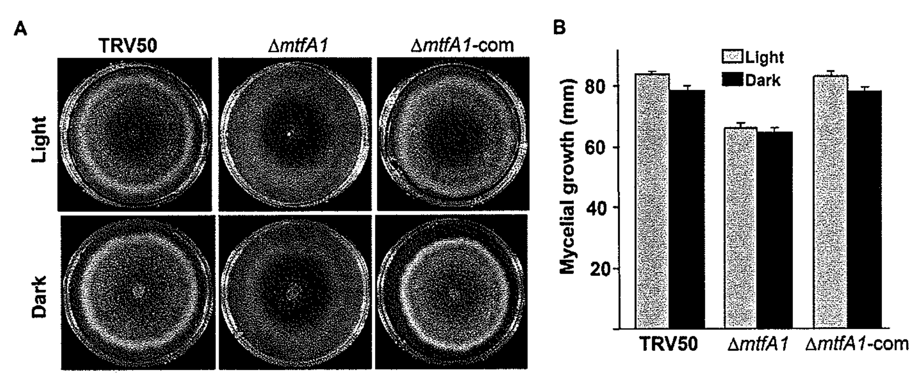
FIG. 4 ΔmtfA mutant is defective in growth. A) Mycelial growth: Approximately 500 conidia of each strain were inoculated in the center of the GMM plates and incubated at 37° C. in dark and light conditions for 6 days. B) Quantification of colony diameter of ΔmtfA strains and control strains on GMM.

Conidiogenesis: strains grown in dark as described in 4A were observed for overall development of conidial head formation. Pictures of conidial masses were taken at 2 cm away from the point of inoculation using dissecting microscope. Quantitative analysis of asexual reproduction in ΔmtfA mutant. A 7-mm-diameter core was removed at 2 cm away from the point of inoculation from culture grown as described in FIG. 4A and homogenized in water. Conidia were counted using a hemacytometer (B). Values are means of three replications. Error bar indicates standard errors. C & D. Quantitative analysis of sexual reproduction: Strains grown as described in FIG. 4A were used for the counting Hulle cells (C) and cleistothecia production (D). Hulle cells were counted simultaneously in the same core that was used for conidial counting in FIG. 5B. Cleistothecia were counted after spraying the mycelial disc of 15 mm diameter (taken at 2 cm away from the point of inoculation from the cultures grown as described in FIG. 4A) with 70% ethanol under dissecting microscope. Values are means of three replications. Error bar indicates standard errors. Asterisks indicate no Hulle or cleistothecia production.

Figure 5:
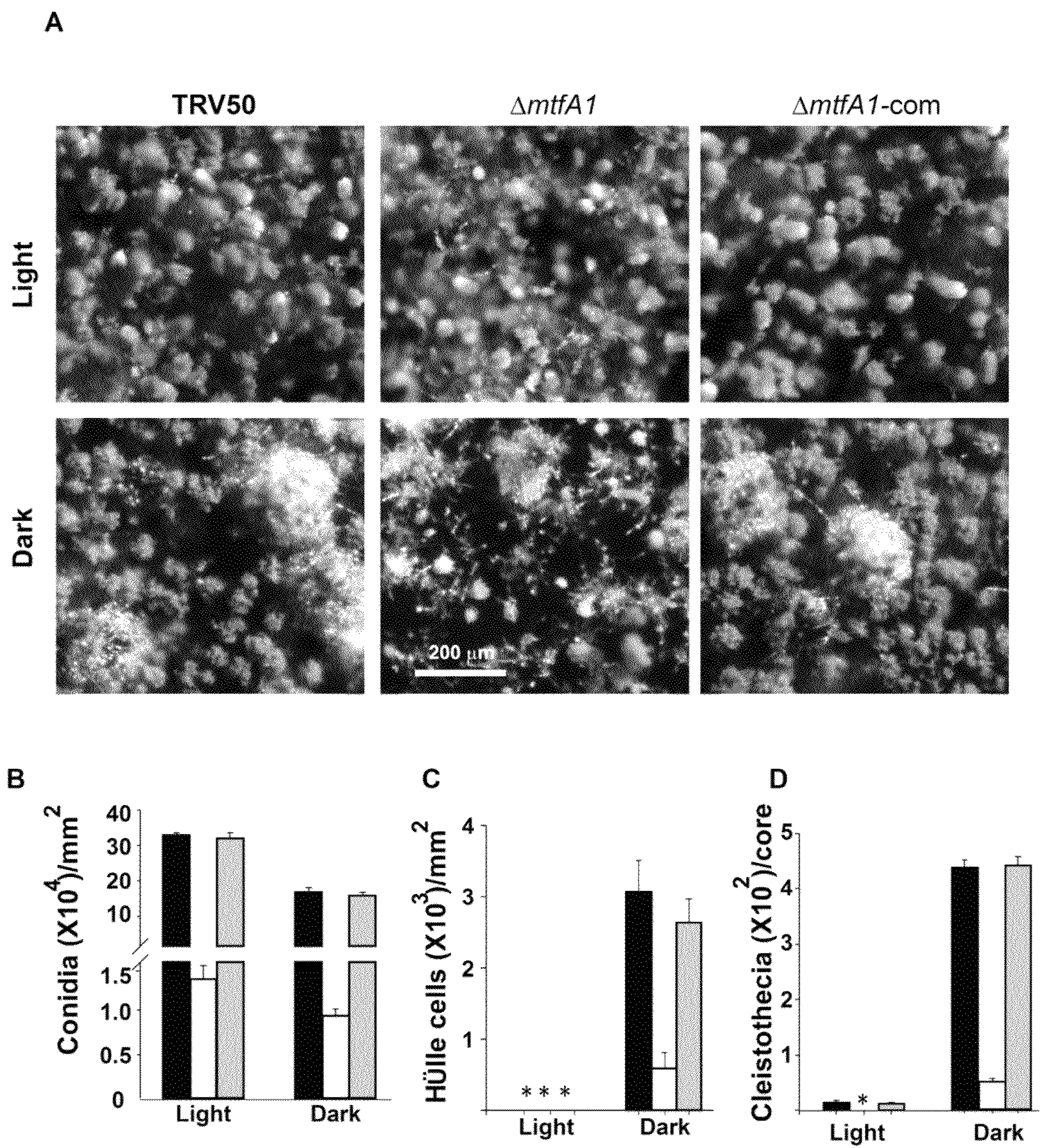
FIG. 5 ΔmtfA mutant is defective in asexual and sexual development
Figure 6:
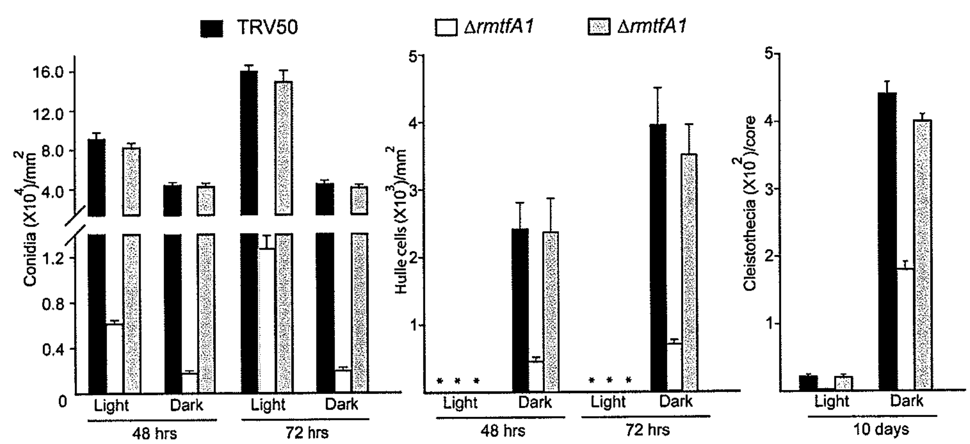
Figure 7A:
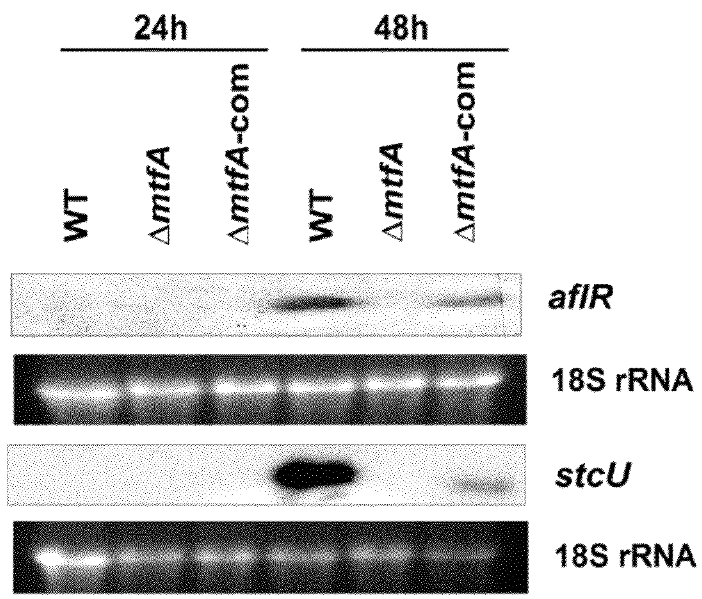
Figure 7B:
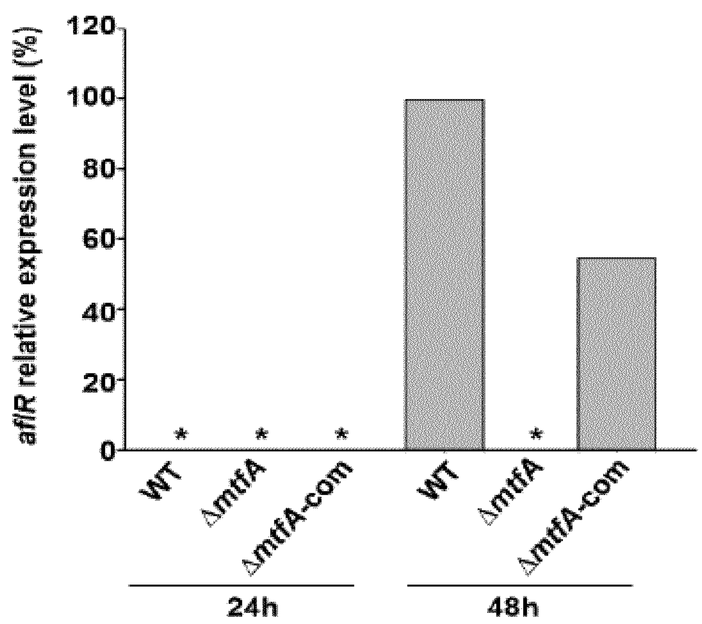
Figure 7C:
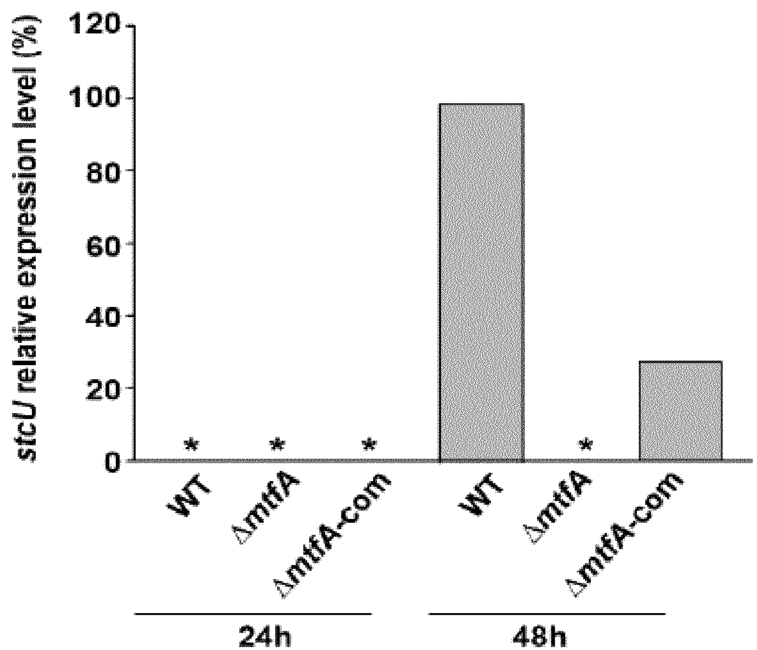
Figure 7D:
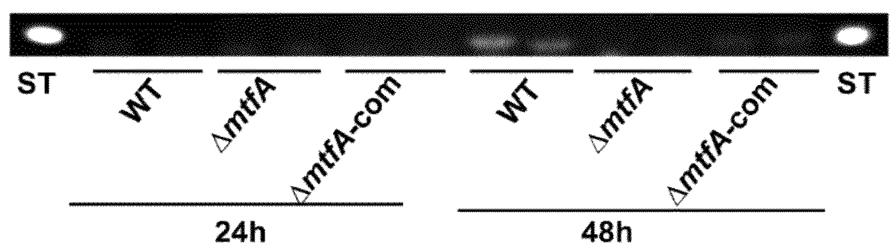
Figure 7E:
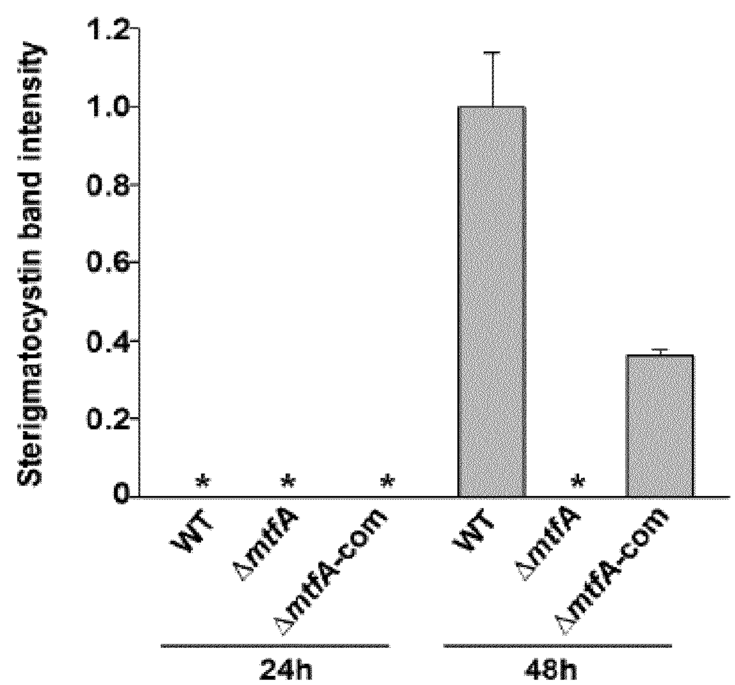

FIG. 6 Analysis of asexual and sexual reproduction of ΔmtfA mutant by top agar inoculation. Quantitative analysis of asexual reproduction in ΔmtfA mutant. Strains were spread-inoculated with 5 ml of top agar containing $10^6$ conidia $ml^{-1}$ on GMM and incubated at 37° C. in dark or light conditions. Culture discs were taken randomly from the plates and the total number of conidia was counted as described in FIG. 5B. Values are means of three replications. Error bar indicates standard errors. Quantitative analysis of sexual reproduction: Strains grown as described above were used for assessing Hulle cells (B) and cleistothecia production (C). Culture discs were taken randomly from the plates and the total number of Hulle cells and cleistothecia were counted as described in FIGS. 5C and 5D. Values are means of three replications. Error bar indicates standard errors. Asterisks indicate no hulla or cleistothecia production.

FIG. 7 mtfA regulates mycotoxin synthesis. TLC analysis of ST production. Strains were grown in GMM liquid shaken cultures (inoculums: $10^6$ conidia $ml^{-1}$) and incubated at 37° C. Twenty-four h and 48 h old culture supernantants were analyzed for ST as described in the experimental procedure. Band C. Densitometries of A. Analysis of aflR and stcU expression by Northern blot. The mycelia were collected at 48 and 72 hrs of incubation. rRNA serves as a loading control.

Figure 8:
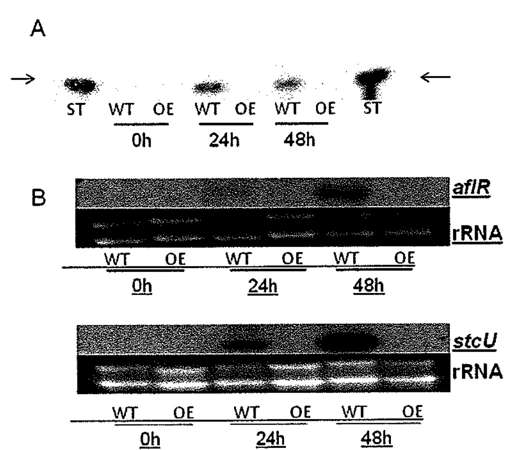

FIG. 8 Overexpression of mtfA suppresses the ST production on GMM medium. TLC analysis of ST production. Strains were inoculated in GMM liquid medium at $10^6$ conidia $ml^{-1}$ and grown for 16 hrs. Mycelia were collected and equal amounts of mycelia were inoculated in TMM agarmedium. The cultures were further incubated for 24 and 48 hrs. Mycelia were collected and toxin analysis was carried out as described in the experimental procedure. Analysis of aflR and stcU expression by Northern blot. The cultures grown as described in FIG. 8A were used for the expression of aflR and stcU analysis. Mycelia were collected at 0 hrs, shifting time—from liquid GMM to solid TMM, 24 and 48 hrs of incubation on TMM. Total RNAs were extracted and expression of aflR and stcU were analyzed. rRNA serves as a loading control.

Figure 9:
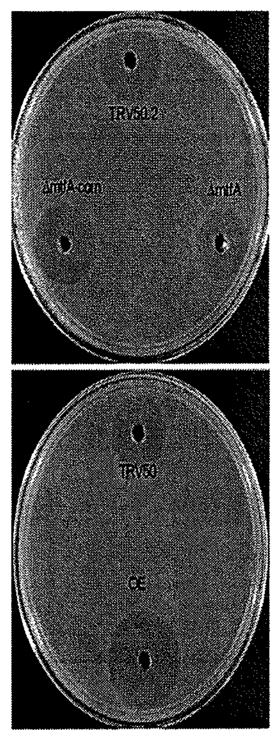

FIG. 9 MtfA regulates penicillin biosynthesis: Deletion of mtfA reduces penicillin production (upper photo) while overexpression of mtfA increases penicillin production (lower photo). The experiment was repeated several times with the same results.

Figure 10:
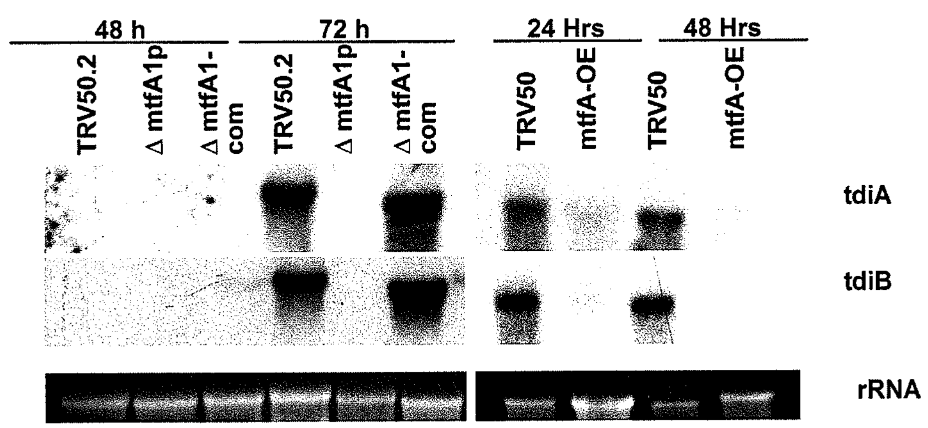

FIG. 10 mtfA controls the expression of genes involved in the synthesis of other secondary metabolites. Deletion or over-expression of mtfA decreases the expression of terraquinone gene tdiA and tdiB. Left panels, strains (WT, deletion mtfA and complementation strain) were grown in GMM liquid shaken cultures (inoculum: $10^6$ conidia $ml^{-1}$) and incubated at 37° C. for 48 and 72 h. Right panels, stains (WT and overexpression mtfA) were inoculated in GMM liquid medium at $10^6$ conidia $ml^{-1}$ and grown for 16 hrs. At that time, mycelia were collected and equal amounts of mycelia were inoculated in TMM liquid medium. The cultures were grown for additional 24 and 48 h after the shift. Total RNAs were extracted and expression of tdiA and tdiB were analyzed. rRNA serves as a loading control.

DETAILED DESCRIPTION OF THE DISCLOSURE

Figure 1:
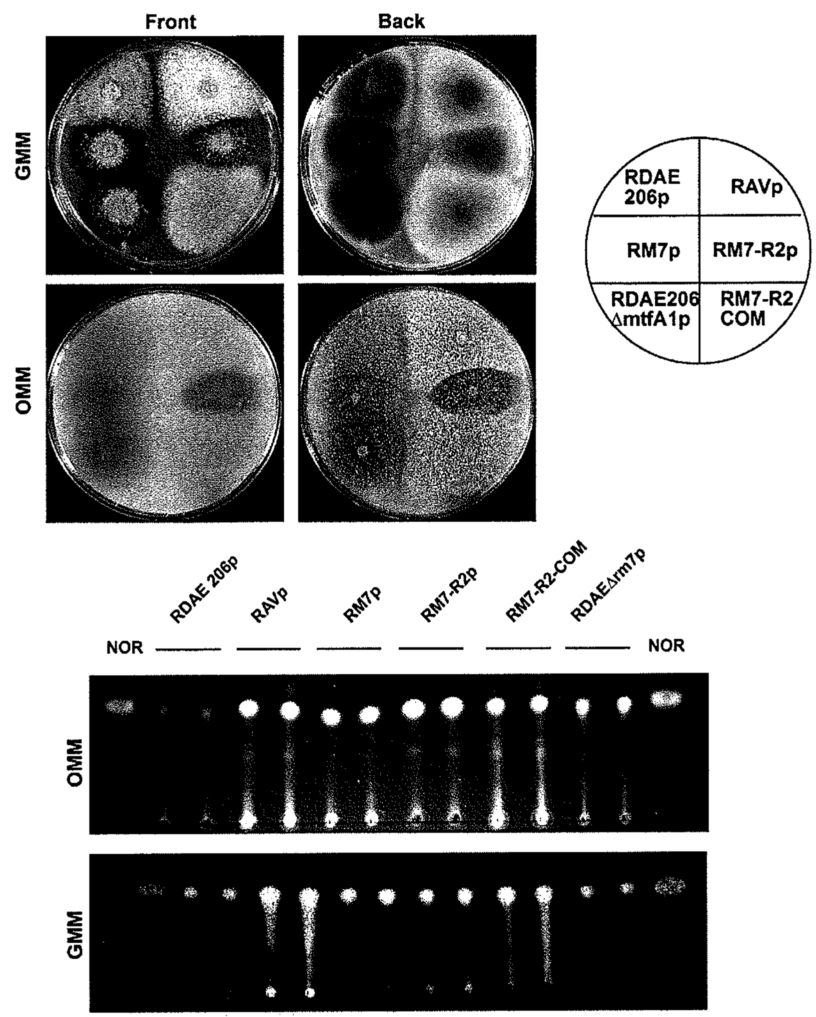
FIG. 1. Revertant mutant 7 (RM7) produces NOR. Mycelia growth and production of NOR compound. Approximately 500 conidia of RM7 and RDAE206 were inoculated on top of OMM and incubated for six days at 37° C. under dark conditions. Pinkish or orange color was observed at the bottom of the plates. TLC analysis of NOR production was done. Fungal strains were top-agar inoculated at $10^6$ conidia/ml on top of OMM and GMM and incubated at light and dark conditions for six days. Mycelial cores were taken, toxin were extracted and analyzed as described in methods and materials.

Locus AN8741.2 Encoding C2H2 Type Transcription Factor is Mutated in RM7 Mutant Seven revertant mutants were generated capable of restoring NOR (orange color intermediate used an indicator of toxin biosynthesis) by chemical mutagenesis of RDAE206 strain which does not have veA gene and does not produce NOR. Genetic and linkage group analysis among these mutant indicated that all the mutants belongs to different linkage group (data not shown). Mutation in rtfA restored the production of NOR (FIG. 1). In order to identify possible other regulatory elements acting downstream of veA gene in the ST biosynthetic pathway, the mutated gene in RM7 mutant was analyzed. In order to make sure RM7 mutant carries single mutation in particular gene, RM7 mutant was crossed with RAV-Pyro2 that lacks veA and stcE genes. However, the heterokaryon of this cross did not produce cleistothecia as described previously (Ramamoorthy et al., 2011). Thus, RM7 mutant was crossed with RAV-pyro1 which lacks stcE gene only. The progeny segregation pattern is described in the methods and material section. Progeny analysis of crosses between RM7 and RAV-pyro1 mutants clearly showed that mutation occurred in a single locus or very closely linked genes in the RM7 mutant (data not shown).

The mutated gene in the RM7-R2 progeny strain (sup-, ΔsteE), obtained as a result of cross between RM7 and Rav-pyro1, not only brought about defective conidiation but also produced pinkish pigmentation instead of orange pigmentation on OMM. This could be due to unknown effect caused by the suppressor gene mutation. Thus, RM7-R2 progeny were used to identify the mutated gene using genomic DNA library complementation (Osherov and May 2000). Defective conidiation/normal conidiation phenotype and pink/bright orange pigmentation were used as two selection markers for selection of positive transformants directly on the transformation medium with assumption that the positively complemented strain would appear full conidiation and produce orange color pigmentation on OMM medium. Upon transformation of RM7-R2 progeny with the genomic library, several positive transformants were obtained that restored conidiation and bright orange color pigmentation on OMM medium. From the positive transformants, Plasmid DNA were rescued, and sequenced. Sequencing of these rescued plasmids indicated that same kind of plasmids was recovered in independent transformants and the genomic fragment in the plasmid contained two hypothetical proteins: one is putative C2H2 finger domain protein, and another one is unknown hypothetical protein. In order to find out where exactly the mutation happened in the RM7 mutant, the corresponding genomic sequences were amplified from RM7 mutant and sequence-analyzed. Sequence analysis indicated that gene encoding C2H2 finger domain containing gene (designated as mtfA) is mutated and the mutation is G-T transversion at nucleotide 3 of ORF of mtfA, changing start codon from ATG (metheonine) to ATT (isoleucine) of MtfA (FIG. 2). The amino acid sequence of *A. nidulans* MtfA revealed significant identity with orthologous protein from other *Aspergillus* spp such as *A. clavatus* (64%), *A. oryzae* (64% identity), *A. niger* (62%) *A. terreus* (61%), *A. flavus* (61)%, and *A. fumigates* (59%) (FIG. 2). MtfA is also conserved in other Acomycetes. No MtfA orthologous protein was found in *Saccharomyces cerevisiae*. Similarly, there is no orthologous proteins of MtfA in plants and animal kingdom.

Figure 3:
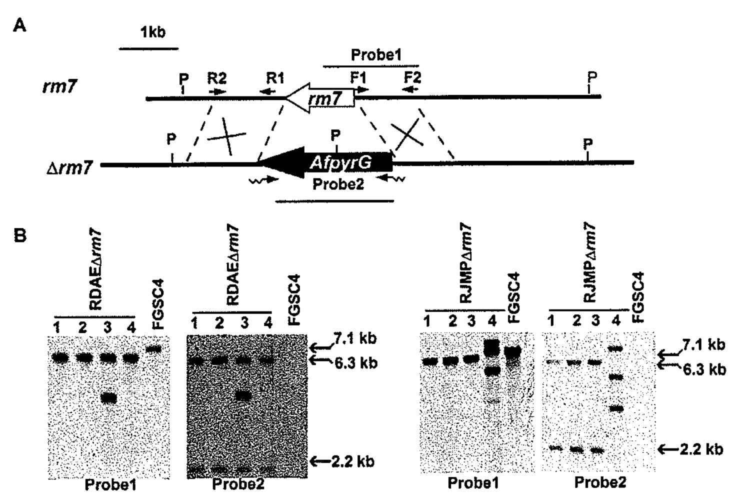
FIG. 3 Targeted replacement of the mtfA gene. The restriction map of the mtfA locus (open arrow) in wild-type is shown in the top line. Gene replacement construct ΔmtfA using *A. fumigates* pyrG gene (AfpyrG) as a selection marker gene is shown in the bottom line. Recombination events between the mtfA locus and ΔmtfA gene replacement constructs are shown by crosses (X). Restriction enzymes: P, PstI. Replacement construct was obtained from FGSC. Primers used for construction of the replacement construct are shown by small arrows as described in FGSC. Southern blot analyses. The ΔmtfA gene replacement construct was transformed in RDAE206 and RJMP 1.49 strains independently. Digested genomic DNA with PstI was hybridized with probe P1 containing 5' flanking sequence of mtfA, probe P2 containing the coding sequence of AfpyrG. TLC analysis of NOR production. Growth conditions and toxin analysis by various strains on OMM and GMM medium were carried out as described in FIG. 1B.

Verification of the Generated mtfA Deletion Mutants by DNA Analysis and Effects of the mtfA Deletion Mutation on NOR Production To make sure that NOR production in RDAE206 strain is indeed due to point mutation of mtfA and also to assess the effect of complete deletion of mtfA on ST synthesis, RDAE 206 and wild-type strain (RJMP1.49) with veA+ genetic background for complete deletion of the mtfA gene were taken. mtfA gene replacement construct was transformed into RDAE206 strain (FIG. 3) and RJMP1.49. The gene replacement was confirmed by Southern blot analysis. (FIG. 3).

A RDAE206ΔmtfA mutant produces NOR as RM7 mutants (FIG. 1) does on OMM and GMM medium indicating mtfA gene functions in connection with veA and regulates mycotoxin synthesis.

Deletion of mtfA Results in a Slight Decrease on Fungal Growth (FIG. 4) and Defects in Sexual and Asexual Development (FIGS. 5 and 6)

mtfA is a positive regulator of both asexual and sexual development in *A. nidulans*. Deletion of mtfA in *A. nidulans* results in a reduces of conidiation and cleistothecia (fruiting bodies) formation. Complementation of the deletion mutant with the mtfA wild type allele rescues wild type morphogenesis.

mtfA Deletion Decreases ST Production in a Strain with a veA Wild Type Allele

Mutation of mtfA (RM7 strain) and deletion of mtfA (RDAE206ΔmtfA) was reported to restore NOR synthesis in ΔveA genetic background. Interestingly, mutation of mtfA in veA1 genetic background (RM7-R2 strain) also synthesized the same level of NOR as ΔmtfA did. A question was how does mtfA function in ST synthesis in veA+ genetic background. So, the production of ST levels was determined in an ΔmtfA mutant. ST analysis indicated that a ΔmtfA mutant does not produce ST, whereas, wild type (TRV50) and complemented strain (ΔmtfA+com) produced higher levels of ST at 48 hrs of incubation on GMM solid cultures (FIG. 7).

The expression of transcript levels of aflR and stcU gene involved in the ST biosynthetic pathway were analyzed. Northern blot analysis of aflR and stcU transcripts clearly indicated that these genes expression is not observed in ΔmtfA deletion mutant whereas aflR and stcU expression is clearly noticed in its isogenic wild-type and complemented strains (FIG. 7).

A mtfA over-expressing strain, mtfA-OE, was also generated expression mtfA under the control of the alcA promoter. Initially, the strains were grown on liquid GMM for 16 hrs. After shifting the mycelium to the induction medium, the mtfA-OE strain produces less amount of ST compared to the isogenic wild-type strain after 24 and 48 hrs of induction. Similarly, the expression analysis of aflR and stcU was analyzed for confirmation of the ST synthesis data. Northern blot analysis of aflR and stcU indicated that the expression of aflR and stcU was suppressed at 24 and 48 hrs of incubation (FIG. 8) under inducing condition of mtfA overexpression.

mtfA Positively Regulates Penicillin Biosynthesis.

VeA regulates biosynthesis of penicillin genes and mtfA is also influenced by VeA with regard to ST production. To see whether mtfA regulates the PN production, the amount of PN production in ΔmtfA strains was compared with isogenic wild-type strains TRV50.2 and its complemented strain ΔmtfA-com. Deletion of mtfA significantly reduced the level of PN production compared to its isogenic wild-type strain TRV50.2 (FIG. 9). Interestingly, overexpression of mtfA showed enhanced levels of PN compared to its isogenic wild-type stain TRV50. mtfA is positively regulates PN production (FIG. 9).

mtfA Regulates the Expression of Terrequinone Gene.

In order to determine if mtfA is also involved in regulation of terrequinone, anti-tumor compound, biosynthesis, we analyzed the expression of mRNA levels of tdiA and tdiB in the terrequinone biosynthetic cluster were analyzed. At 48 and 72 h of incubation in GMM, the expression of tdiA and tdiB were noticed in TRV50.2 and ΔmtfA-complementation strains, however, the ΔmtfA did not exhibit expression of neither tdiA nor tdiB mRNA transcript at 48 or 72 h of incubation on GMM (FIG. 10). Interestingly, mtfA-OE strain showed lower levels of both tdiA and tdiB transcripts compared to the isogenic wild-type strain, TRV50 at both 24 and 48 h after induction shift for mtfA overexpression (FIG. 10).

MtfA Subcellular Localization

MtfA is located mainly in nuclei

EXAMPLES

Examples are provided for illustrative purposes and are not intended to limit the scope of the disclosure.

Materials and Methods

Novel veA-Dependent Genetic Elements

To identify novel veA-dependent genetic elements involved in the regulation of ST biosynthesis in the model system *A. nidulans*, a mutagenesis in a deletion veA strain to was performed to obtain revertant mutant that regain the capacity to produce toxin. Several revertant mutants (RM) were obtained. In the present study we characterized one of the selected revertants, RM7 is disclosed. This revertant presented a point mutation in a gene that we denominated mtfA (master transcription factor) encoding a novel putative C2H2 zinc finger domain type transcription factor. The mtfA effect on ST production is veA-dependent. Additionally, mtfA regulates the production of other secondary metabolites, such as penicillin and terraquinone. Furthermore, mtfA is also important for sexual and asexual development in *A. nidulans.*

A. *Aspergillus nidulans* mtfA coding region was fused to the alcA(p)promoter and introduced into *Aspergillus nidulans* cells. Cells were grown in penicillin inducing medium were antibiotic levels increased approximately 25%.

B. *Aspergillus nidulans* mtfA coding region was fused to the alcA(p)promoter and introduced into *Aspergillus nidulans* cells. Cells were grown under conditions that allow the production of the mycotoxin sterigmatocystin, an aflatoxin-related mycotoxin. Induction of the overexpression promoter under these conditions C. Deletion of the mtfA coding region results in elimination or reduction of the mycotoxin sterigmatocystin even under conditions that induce toxin production.

Improved yield in penicillin G production has been already achieved by overexpression of mtfA. Over-expression can be also be achieved by using other strong promoters (contitutive or inducible) or by introducing multicopies of all or parts of the mtfA gene in cells.

Fungal Strains and Growth Conditions

Fungal strains used in this study are listed in Table 1. Media used include complete media YGT (0.5% yeast extract, 2% dextrose, trace elements), glucose minimal media (GMM) (1% dextrose, nitrate salts, trace elements pH-6.5) and oat meal media (OMM) (1% oat meal). Nitrate salts, trace elements and vitamins were as described previously (Kafer 1977). Uridine and uracil, amino acids and vitamins were added when necessary to supplement the auxotrophic markers. Uracil and uridine were added to YGT media for pyrG auxotroph. Glucose was replaced with threonine in threonine minimal medium (TMM) for induction of alcA promoter.

Genetic Techniques

Crosses between strains were followed as described (Pontecorvo et al. 1953.). Crossing between RAV-pyro1 and RM7 was made and progenies were analyzed for the presence/absence of veA and suppressor mutation based on production of NOR and colony morphology and finally confirmed by PCR. The cross resulted in progenies that falls in four groups based on phenotype such as 1. RM7 Parental type (strongly defective in conidiation, positive for NOR production); 2. RAV-pyro1 parental type (normal condiation, positive for NOR production); 3. Recombinant type RM7-R1 (ΔveA and ΔstcE) (appeared as that of RDAE 206 strain. i. e. slightly defective in conidiation and negative for NOR production) and recombinant type RM7-R2 (moderately defective in conidiation and positive for NOR production).

Identification of Mutated Gene in the RM7 Mutant

To find mutated gene in RM7 mutant, it should be complemented with genomic library and positive complemented strain should not produce NOR as that of parental RDAE206 in which mutagenesis was carried out.

RM7-R2 (sup-) producing a brownish-pink pigmentation and moderated defect in conidiation was used for complementation with the *A. nidulans* genomic library. Positive transformants that restored wild-type phenotype were selected. Genomic DNA was prepared from these transformants; plasmid DNA was rescued by transforming *E. coli* cells with total genomic DNA. For each gene, 5-10 ampicillin-resistant colonies were picked and the plasmid DNA was extracted and analyzed by restriction digestion and PCR as described previously (Osherov and May 2000). Finally, both the ends of insert DNA fragments of the isolated plasmid were sequenced and the total genomic sequences present in the plasmid DNA were acquired from the *A. nidulans* genome database at broad Institute webpage (http://www.broadinstitute.org/annotation/genome/aspergillus_group/MultiHome-.html) by BLAST analysis. The exact location of the mutation in RM7 mutants is identified by PCR amplifying and sequencing the corresponding genomic region.

Fungal Transformation and Genetic Manipulation

Polyethylene glycol-mediated transformation of protoplasts was carried out as described earlier (Miller et al. 1985; Yelton et al. 1983). DNA and RNA isolation, gel electrophoresis, standard molecular manipulations, and Southern and Northern blot analysis were performed as described previously (Miller et al. 1987; Miller et al. 1985; Sambrook and Russell 2003; Vallim et al. 2000).

Creation of the mtfA Deletion Mutant by Gene Replacement and Generation of the Complementation Strain The entire coding region of mtfA gene (locus AN8741.2) was replaced in RDAE206 and RJMP 1.49 strains using the gene deletion cassette obtained from FGSC (http://www.fgsc.net). The deletion cassette was transformed into protoplasts of RDAE206 and RJMP 1.49 strains and transformants were selected on appropriate selection medium and finally confirmed by Southern blot analysis. The deletion strains were designated as RDAEΔmtfA and ΔmtfA respectively.

To complement ΔmtfA, the entire mtfA gene with upstream and downstream fragment was amplified with RM7com1 and RM7com2 primer pair, digested with SacII and KpnI and cloned into pSM3 vector as pSM3-rm7com. The complementation vector, pSM3-rm7com was transformed into ΔmtfA strain and transformants selected on appropriate selection medium and complementation was confirmed by PCR and Southern blot analysis. The complemented stain is designated as ΔmtfA-com.

Strains isogenic with respect to the auxotrophic markers were generated and used in this study, differing only in the presence or absence of mtfA.

Overexpression of mtfA

To over express the mtfA gene, the entire gene of mtfA was amplified starting from start codon to stop codon with RM7-OE1 and RM7-OE2 primer pair, digested with kpnI and PacI and cloned into pmacro having alcA promoter and trpC terminator as pMacroRm7OE vector. The pMacroRm7OE vector was transformed into RJMP 1.49 and transformants were selected on appropriate selection medium and confirmed by Southern blot analysis.

For mtfA over-expression analysis, 400 ml of liquid GMM was inoculated with spore suspension to the final concentration of $10^6$ conidia/ml and incubated for 16 hrs at 37° C. and 250 rpm. The mycelium was collected, washed with double distilled water and squeezed in between paper towel. Equal amount of mycelium was then inoculated on the induction medium, threonine minimal medium ( ). The mycelium was collected at 24 and 48 hrs after shift to the induction medium and ST and RNA analysis for aflR and stcU were carried out.

The strains used in this study were isogenic with respect to the auxotrophic markers differing only in the modifications at the mtfA locus.

Toxin Analysis.

Plates containing 25 ml of solid GMM or OMM with appropriate supplements were inoculated with five milli liter of top agar with spore suspension containing $10^6$ spores/ml. The cultures were incubated in dark. Three cores (16 mm diameter) from each replicate plate were collected in a 50 ml Falcon tube. Alternatively, strains were grown in GMM liquid shaken cultures (inoculum $10^6$ conidia $ml^{-1}$) and incubated at 37° C., Twenty-four h and 48 h old culture supernantants were analyzed for ST. NOR and ST was also analyzed in TMM overexpression mtfA and control cultures NOR or ST were extracted with $CHCl_3$. The extracts were dried overnight and then resuspended in 200 μl of $CHCl_3$. Two micro liter of ST/NOR standard and 25 μl of the samples were fractionated in the silica gel thin-layer chromatography (TLC) plate using benzene and glacial acetic acid [95:5 (v/v)] as a solvent system for ST analysis and chloroform:acetone:n-hexane (85:15:20) as a solvent system for NOR. The plates were then sprayed with aluminum chloride (15% in ethanol) and baked for 10 min at 80° C. ST/NOR bands on TLC plates were viewed by exposing the plates under UV light (375-nm).

Morphological Studies

Asexual and sexual developmental studies were performed in *A. nidulans* strains TRV50, ΔmtfA, ΔmtfA-COM (Table 1). Plates containing 25 ml of solid GMM with the appropriate supplements were spread-inoculated with 5 ml of top agar containing $10^6$ spores/ml. The cultures were incubated at 37° C. in dark or in light conditions. A 7-mm-diameter core was removed from each spread plate culture and homogenized in water to release the spores. Conidia were counted using a hemacytometer. Identical cores were taken to examine cleistothecial production under a dissecting microscope. To increase visualization of cleistothecia, the cores were sprayed with 70% ethanol to remove conidiphores.

For radial growth analysis, approximately 500 conidia of each strain were point inoculated and incubated for 6 days under light and dark conditions. The radial growth was measured after six days of incubation. Experiments were performed triplicate, and the mean and standard error were calculated.

Penicillin Analysis

The PN bioassay was performed as previously described (Brakhage et al., 1992) with some modifications, using *Bacillus calidolactis* C953 as the test organism. Briefly, strains were inoculated with approximately $10^6$ spores $ml^{-1}$ in 25 ml of seed culture medium, and incubated at 26° C. for 24 h at 250 rpm. Mycelia were then transferred to PN-inducing medium (Brakhage et al., 1992). The experiment was carried out with three replicates. After 96 h, the cultures were filtered using Miracloth (Calbiochem, USA) and the supernatants were collected for analysis. Three hundred milliliters of Tryptone-Soy Agar was supplemented with 20 ml of *B. calidolactis* C953 culture and plated on three 150-mm-diameter Petri dishes. One hundred microliters of each culture supernatant was added to 7-mm-diameter wells. Bacteria were allowed to grow at 55° C. for 16 h and inhibition halos were visualized and measured. To confirm that the observed antibacterial activity was due to the presence of PN and not to the presence of different fungal compounds in the supernatant, additional controls containing commercial penicillinase from *Bacillus cereus* (Sigma, Mo., USA) were used. A standard curve using various concentrations of PN G (Sigma, Mo., USA) was used to determine PN concentration in the samples.

Gene Expression Analysis

Total RNA was extracted from lyophilized mycelial samples using RNeasy Mini Kit (Qiagen) or Triazol (Invitogen), following the manufacturer's instructions. Northern blots were used to evaluate gene expression levels of aflR, stcU, tdiA and tdiB. For making probe for northern blots were aflR, a 1.3-kb EcoRV-XhoI fragment of pAHK25 (Brown et al., 1996); stcU, a 0.75-kb SstII-SmaI fragment of pRB7 (Yu et al., 1996).

Conservation of MtfA Homologs from Different Fungal Specie

When comparing with other fungal species, the deduced amino acids of the homologs from different fungal species are used. Tables 2 and 3 show a high degree of conservation between MtfA homologs from different fungal species, including species that produce penicillin (*Penicillium chrysogenum*) or other important secondary metabolites such as lovastatin (*Aspergillus terreus*) at industrial levels, among others.

TABLE 1

Study of mMtfA subcellular localization: mtfA was tagged with GFP

| Sl. No | Strain name | Genotype | Description | Reference |
|---|---|---|---|---|
| 1 | FGSC4 | Wild-type | Wild-type control | FGSC |
| 2 | RDAE206 | yA1, pabA1, pyrG89, argB2, ΔstcE::argB, ΔveA ::argB | Mutagenesis study | |
| 3 | RAV1 | wA1, yA2, pabA1, pyrG89, argB2, ΔstcE::argB, veA1 | Positive NOR producer | |
| 4 | RAV-pyro1 | wA1, yA2, pyroA4, argB2, ΔstcE::argB, veA1 | To cross with RM7 to find out mutation pattern in RM7 mutants | Ramamoorthy et al., 2011 |
| 5 | RAV-pyro1 | wA1, yA2, pyroA4, argB2, ΔstcE::argB, ΔstcE::argB | To cross with RM7 to find out mutation pattern in RM7 mutants | Ramamoorthy et al., 2011 |
| 6 | RM7 | yA2, pabA1, pyrG89, argB2, ΔstcE::argB, ΔveA::argB, mtfA⁻⁻ | mutants | Ramamoorthy et al., 2011 |
| 7 | RM7-R2 | wA1, yA2, pyrG89, argB2, ΔstcE::argB, mtfA⁻⁻, veA1 | For transformation and identification of mutation in the genome | Present |
| 8 | RM7-R2-com | wA1, yA2, pyrG89, argB2, ΔstcE::argB, mtfA⁻⁻ pRG3-AMA-NOTI-mtfA::pyr4, veA1 | Complementation of RM7-R2 with wild-type mtfA | Present |
| 9 | RJMP1. 49 | pyroA4, pyrG89 argB2, delnku::argB, veA+ | For generation of mtfA gene replacement | Present |

TABLE 1-continued

Study of mMtfA subcellular localization: mtfA was tagged with GFP

| Sl. No | Strain name | Genotype | Description | Reference |
|---|---|---|---|---|
| 10 | TRV50 | pyroA4, pyrG89, pyrG+, argB2, delnku::argB, veA+ | Wild-type control strain | Present |
| 11 | TRVΔmtfA | pyroA4, pyrG89, ΔmtfA::AfpyrG, argB2, delnku::argB, veA+ | To study mtfA functionality | Present |
| 12 | TRVΔmtfA-com | pyroA4, pyrG89, ΔmtfA::AfpyrG, argB2, delnku::argB, veA+ mtfA::pyroA | Complementation strain of TRVΔmtfA | Present |
| 13 | mtfAOE | pyroA4, pyrG89, alcA::mtfA::pyr4, argB2, Δnku::argB veA+ | To over-express mtfA | Present |
| 14 | TRV-Stag | pyroA4, pyrG89 mtfA::stag::afpyrG, argB2, delnku::argB, veA+ | To study interacting proteins by pull down experiments | Present |
| 15 | TNO2A7 | pyroA4, riboB2, pyrG89, argB2, nkuA::argB veA1 | | Present |
| 16 | | | | |

TABLE 2

Amino acid comparison of the predicted gene products of mtfA homologs. (SEQ ID NOS 2-14, respectively, in order of appearance). The analysis indicates high conservation of this gene and gene product in different fungal species. Shaded part indicates the domains with highest conservation.

```
A. nidulans      1  MDLANQPGPEPALTAKSRYSPPAFEPGSFYAA------S-----------------T
A. oryzae        1  MDLAS-PGPEPIYKSRASYSPPPSSAGSYKRP------AE------------HDSYF
A. niger         1  MDLASHPGPDPIMKSRASYSPPM---TSYKRS------IEHTSDSYFP--SV---PI
A. kawachii      1  MDLASHPGPDPIMKSRASYSPPM---TSYKRS------IEQTSDSYFP--SV---PI
N. fischeri      1  MDVAS-PSESDTVPTFRSRSIQNSSASHYKRL------SEQYTGSYFS--AAPTHTT
P. chrysogenum   1  MDLSNHSAAVKPI-----YTP------------------------------V---ES
C. immitis       1  MNVSSCDQPHQLRAPASSYSEHR-----------RSP---SIPKPLQT--ESSSCAS
A. capsulatus    1  MNLSHSYHSPPST-----YP---HSGTSQKRQSLQSESSLSVSNGYYD---RNASNL
U. reesii        1  MNVSSCDQTAPFHGSATSYFEHHQR--------IRSP---SIPKRSHE--ENSSSAS
P. marneffei     1  ------------------------------------------------------------
B. fuckeliana    1  -MA--------------------------------------SSLVSNPYTVHPMAQHSSY
N. tetrasperma   1  -------------------------------------------MAPTTLTPQ--YPAQPY
N. crassa        1  -------------------------------------------MAPTTLTPQ--YPAQPY
M. oryzae        1  -MA--------------------------------------ATMIQQPYPIH--QQQSQY
C. globosum      1  -MA--------------------------------------NTMVTHYAHVP--QHSLQY
F. oxysporum     1  ------------------------------------------------------------

A. nidulans     38  SFT-RTQARSSALLDSTQAP-------KRQRLSSPMH--
A. oryzae       42  SRAPQAQ-PEGADSTYAA-------KRQRTSPPPR--
A. niger        47  TRSPQPQSPEGAMHAA-------KRTRMTPPLQ--
A. kawachii     47  TRSPQPHSPEGAMHAA-------KRTRMTPPLQ--
N. fischeri     52  SRTPQPPLSPPAEDQ-PKCSLPSISILLENAAHAA-------KRQRTSLSTH--
P. chrysogenum  23  -YKRSPPLSPPA--PKVFEGQHAATSLTLNLPERQRLSPSLG--
C. immitis      45  PYSRFERLPLSPPEEDGKTQFRGVVSDAHV------AKRQRTNPPPS--
A. capsulatus   50  AYARSPQPQ-SRFQGADQLSPVHI------AHRPNPLST--
U. reesii       48  PYPPFATLPLSPPEGKTTFQSVDTHV------AKRQRANPPPS--
P. marneffei     1  ------------------------------------------MDNVPASKRA-------
B. fuckeliana   22  VNAPQPPPT-SGLSSPTEQAQQQSSPQQAAFKE-----
N. tetrasperma  16  GFAP----PPS-NKCSLPSISNLLVMADQPTSETSPQSQQLH----------
N. crassa       16  GFAP----PPS-NKCSLPSISNLLVMADQPTSETSPQSQQLH----------
M. oryzae       20  MVQPQGPP-D-NKCSLPSISNLLGLADQPTSETSAQYTPRAEATTRLLATG
C. globosum     20  GYMP----PPA-AKCSLPSISNLLGLADQPTSETSPQSQQQQAQQQQQQC
F. oxysporum     1  -------------MEE-QKCSLPSISNLLGLPTSESSPTSRQHSPRFEV-----
```

TABLE 2-continued

Amino acid comparison of the predicted gene products of mtfA homologs. (SEQ ID NOS 2-14, respectively, in order of appearance). The analysis indicates high conservation of this gene and gene product in different fungal species. Shaded part indicates the domains with highest conservation.

```
A. nidulans      88  -------------------REPLDKNP-SA--------GAAPIEGSGFHSA
A. oryzae        92  -------------------RESEFRSP-YDS--------VSTPNGHSG
A. niger         98  -------------------RDLDSRQQ-SQAY--DLKANGPQIGSSFHSA
A. kawachii      98  -------------------RDLDSRQQ-SQAY--DLKANGPQIGSSFHSA
N. fischeri     102  -------------------RD--SGPP-YDS--------ITPHGSGFHSN
P. chrysogenum   78  -------------------D---------------RHVRVQSYEGSGHAHR
C. immitis       97  -------------------IDLGMERRT------IDQTLKQRPLMNST
A. capsulatus   101  -------------------GEVDLKSQGHGAT--QKPIHRPRMIGSGLDGR
U. reesii       100  -------------------IDLALERRG--AC--ADQAIRQRPLMGGV
P. marneffei     11  ------------------------RH---------DSGDYSRGFCSGFTEG
B. fuckeliana    76  -----------------------DYESGHQYGPSSSMSSRGQSDGGFDGR
N. tetrasperma   61  -------------------FSKPDNNSSQF--GNPA-SIRANSSEASFEGY
N. crassa        61  -------------------FSKPDNNSSQF--GNPA-SIRANSSEASFEGY
M. oryzae        78  ---KQATKGNNLAVILTSQTAAQQSNSSHY--SNAVQSVRQTSETSFDGY
C. globosum      75  MSSSWWDMGHLDTDSTPAQGSKPETNSSHY--TNPV-TIRTSSDASFEGF
F. oxysporum     41  ---------------------PPPSHGHSRAG--SEWAKSSHRSTDASFEGY

A. nidulans     120  GHSPSS--------SISSISMIKSEYPA--PPSAPVS-LP---G-SPTDRSSISSQGS
A. oryzae       124  HHSPSA--------SSVTSGK----AIK--LESYSQT-PM---T-SPSDRSSISSQGS
A. niger        136  GHSPAS--------S-ISAASDAAAPKR--SDSYPQV-PM---A-SPSDRSSISSQGS
A. kawachii     136  GHSPAS--------S-ISAASDAAAPKR--SDSYPQV-PM---A-SPSDRSSISSQGS
N. fischeri     132  GHSPSA--------SSVSATSSSAVMKN--TETYSQA-PI---G-SPTDRSSISSQGS
P. chrysogenum  104  RASPVE--------SLSHKEAH------------------------QHHLHRSSISSNSS
C. immitis      132  SQSPSTSSPPRSAISLPSLVRSYPSPV----SEVPEGRRM---SQISRHSRGASTSQTSQ
A. capsulatus   140  NHSPAGSSPSSAHSPISVANLT---SSSSADPSYQHRMPQ---GPPQSTNSP
U. reesii       137  NHSPSASSPPRTAISLPSLIGSYPSPV----SEAPEGRRM---SQISRHSSSSQ
P. marneffei     38  SSPASLPSGRSHSASISSAVSHPSHQQRTSLPSISASLQN---T-PIHPSERLSISSLAS
B. fuckeliana   113  QSPSQASTSSYSVVSAPNYYFN-PSQVSAINNMEPHAQRQPVQTVTRRVSMPVSSMQYG-
N. tetrasperma   99  RSPSSKPASQSQG---SSNYYYETTPPLSQHEADSR--QM--ATAAPRAPVQSSTFQTQ-
N. crassa        99  RSPSSKPASQSQG---SSNYYYETTPPLSQHEADSR--QM--ATATPRAPVQSSTFQTQ-
M. oryzae       133  NSPSNKSVSQLPA---TGYYFEATPPPGHME-MEPR--PH--MTSVSRVPVQAPFACSA-
C. globosum     132  NSPSTRSVSQVPN---GSNYFFETTPPLQME-ADAR--QMTAAAAVSVQASAYQPQ-
F. oxysporum     78  SSPTRKPSNQAYPGSAPRTYYYETTPPLEAD---AQ--RQASVTAATPPATAPYPQ-

A. nidulans     165  APQ-HQHGPYASPAAPSS----PSSAMYYQHQRPASSGTYQAP-------
A. oryzae       165  VHH-VSAAPYASPAA-SSS----APSAM-YYQRP---SGSYQTP--ATVPS
A. niger        180  VQH-VSSASYASPA-SS----ASSAMF-YQRT--------------APS
A. kawachii     180  VQG-VSSASYASPA-SS----ASSAMF-YQRT--------------APS
N. fischeri     177  VQH-AAGAPYASPA-SFSS----TPSTAAYYQRNP-APNQNP--GSFPP
P. chrysogenum  132  VHIPRNTVPYASPV-TAP----Q--QPMYYPRRPTT-SQPSTPASAPQ
C. immitis      185  LSGPET--RYPSPPNVNSPTFAAA----PKPTEYYPASR---PVPPVA------
A. capsulatus   194  VSLPEKHYAPSSNLSSTPFAL----ANSTE--YYHRPS-HPPSTSIPLAAP-
U. reesii       190  HPGPEA--RYPSPPTLSSPSFAAP----PKPEYYSSGAR---PTNFPPVT------
P. marneffei     94  HDSSRL--SHAIPSPSST--TASITTTA----TPSTS-YYSTSE--EKAYPRSHSTSAPV
B. fuckeliana   171  HSPFNGSYTMSPGAQSYYP---QTQSPQVSSLYYQRPL--PQQFPPPM------
N. tetrasperma  151  ---YPSSAGYS-SQSGMNPYYPPMQPTPPPQ-QQMSGLYYQRPL--PQTPA-------
N. crassa       151  ---YPSSAGYS-SQSGMNPYYPPMQPTPPPQ-QQMSGLYYQRPL--PQTPA-------
M. oryzae       184  ---YSAPYGMA-PSNPMAAYYPTMQPTPPPQQPQISSLYYQRPL--PQAFP-P-------
C. globosum     185  ---YAPGPAYM-SQPAMTSYYPPMQSAAPPQ-TQMSGLYYQRPL--PQPPP-------
F. oxysporum    132  ---QAHPTVYA-NPAPVGAYYPAAQVPPAV-QPQEMNPYYQRPL--PQAYPPP-------
```

TABLE 2-continued

Amino acid comparison of the predicted gene products of mtfA homologs. (SEQ ID NOS 2-14, respectively, in order of appearance). The analysis indicates high conservation of this gene and gene product in different fungal species. Shaded part indicates the domains with highest conservation.

```
A. nidulans     213 ------------PPPPQHQPMIS-TPAWQHHHYFPPSSNTPYQQNHDRYICRTCHKAF
A. oryzae       213 PS------AAPMPASATHQQMIT-TPYQQNHDRYICRTCHKAF
A. niger        219 TS------AAPLPTPAAPQQIIS-NPAWQHHHYFPPSSTTPYQQNHDRYICRTCHKAF
A. kawachii     219 TS------AAPLPTPAAPQQIIS-NPAWQHHHYFPPSSTTPYQQNHDRYICRTCHKAF
N. fischeri     228 TS------AASLP-SPGHQQMIS-TTPYQQNHDRYICRTCHKAF
P. chrysogenum  184 MPPVQVQTQQPHSHSHSSSALIS-TPYQQNHDRYICRTCHKAF
C. immitis      230 --------FAVLPSQPTHPQVL-GSPAWQHHHYFPPSNLNHDRYICRICHKAF
A. capsulatus   247 -----------PAQQHHHHSM-----ISTWQHHHYFPPSNTAPYPQNHDRYICRICHKAF
U. reesii       235 --------FAVLPSQPTHPQMV-ALGSPAWQHHHYFPPSNLNHDRYICRICHKAF
P. marneffei    143 TP---------STLVPPPPAMLSNHLT
B. fuckeliana   220 --------------MPVSVTLTPSSGANPWQHHHYISPSSASQDRYICQTCNKAF
N. tetrasperma  197 --------------VPVPVTLAPVTGANPWQHHHYIASQDRYICQTCNKAF
N. crassa       197 --------------VPVPVTLAPVTGANPWQHHHYIASQDRYICQTCNKAF
M. oryzae       230 --------------MPVNVSMGPQSGANPWQHHHYISPSAASQDRYICQTCNKAF
C. globosum     231 --------------MSMSMTLAPTA-GNPWQHHHYIAPSASQDRYICPTCSKAF
F. oxysporum    178 --------------VSMPA--PAPSGANPWQHHHYLNGAAASQDRYICPTCNKAF

A. nidulans     260 SRPSSLRIHSHSHTGEKPFRCTHAGCGKAFSVRSNMKRHER------AVAMV--
A. oryzae       266 SRPSSLRIHSHSHTGEKPFRCTHAGCGKAFSVRSNMKRHER------PVATAMV
A. niger        272 SRPSSLRIHSHSHTGEKPFRCTHAGCGKAFSVRSNMKRHER------GCHSGRPVATAMV
A. kawachii     272 SRPSSLRIHSHSHTGEKPFRCTHAGCGKAFSVRSNMKRHER------GCHSGRPVATAMV
N. fischeri     280 SRPSSLRIHSHSHTGEKPFRCTHAGCGKAFSVRSNMKRHER------PVATAMV
P. chrysogenum  243 SRPSSLRIHSHSHTGEKPFRCTHAGCGKAFSVRSNMKRHER------GCHSGRPAPAPAA
C. immitis      281 SRPSSLRIHSHSHTGEKPFRCPHAGCGKAFSVRSNMKRHER------GCHPGRSAPPSAL
A. capsulatus   291 VNCGKSFSVRSNMKRHER------PTQAALV
U. reesii       286 SRPSSLRIHSHSHTGEKPFRCPHAGCGKAFSVRNQPRSQRSLIEKRKGYAIGFDEWVLTM
P. marneffei    194 SRPSSLRIHSHSHTGEKPFRCTHAGCGKAFSVRSNMKRHER------GCHSGRPMTATVV
B. fuckeliana   266 QNCGKAFSVRSNMKRHER------GCHSFESASMV--
N. tetrasperma  243 ------GCHSFESSNGRSS
N. crassa       243 ------GCHSFESSNGRSS
M. oryzae       276 ------GCHNYDSSSSNGT
C. globosum     276 FPGCGKAFSVRSNMKRHER------GCHNYDSSSTTSS
F. oxysporum    222 ------GCHSFEFNGSVIR

A. nidulans         ------------------------------------------------------------
A. oryzae       320 ------------------------------------------------------------
A. niger        326 ------------------------------------------------------------
A. kawachii     326 ------------------------------------------------------------
N. fischeri     334 Q-----------------------------------------------------------
P. chrysogenum  297 TALVV-------------------------------------------------------
C. immitis      335 VN----------------------------------------------------------
A. capsulatus   345 N-----------------------------------------------------------
U. reesii       346 ITPTIRSTNEQIYTTASCKIANVAVININRRIAELRKSFRNRRSNGTLSPTKRRVKLAFS
P. marneffei    248 ------------------------------------------------------------
B. fuckeliana       ------------------------------------------------------------
N. tetrasperma  297 GNSNN---GASA------------------------------------------------
N. crassa       297 GNSNN---SASA------------------------------------------------
M. oryzae       330 AMH---------------------------------------------------------
C. globosum     330 TGTMNSNTGGSR------P-----------------------------------------
F. oxysporum    276 G-----------------------------------------------------------
```

TABLE 3

Amino acid sequence comparison of MtfA in *Aspergillus nidulans* with other fungal species. The comparisons were done using the BLASTp tool provided by NCBI (National Center for Biotechnology Information) and EMBOSS Needle - Pairwise Sequence Alignment tool provided by EMBL-EBI (European Bioinformatics Institute).

| Name of the species, with the strain information | NCBI | | EMBOSS Needle - Pairwise Sequence Alignment (global alignment) | | |
|---|---|---|---|---|---|
| | Accession number | E-value (Blastp) | Length | % Identity | % Similarity |
| *Aspergillus oryzae* [RIB40] | XP_001823905.1 | 0 | 332 | 64.2 | 70.8 |
| *Aspergillus clavatus* [NRRL 1] | XP_001270264.1 | 2E−111 | 347 | 65.1 | 71.2 |

TABLE 3-continued

Amino acid sequence comparison of MtfA in *Aspergillus nidulans* with other fungal species. The comparisons were done using the BLASTp tool provided by NCBI (National Center for Biotechnology Information) and EMBOSS Needle - Pairwise Sequence Alignment tool provided by EMBL-EBI (European Bioinformatics Institute).

| Name of the species, with the strain information | NCBI | | EMBOSS Needle - Pairwise Sequence Alignment (global alignment) | | |
|---|---|---|---|---|---|
| | Accession number | E-value (Blastp) | Length | % Identity | % Similarity |
| *Aspergillus niger* [CBS 513.88] | XP_001395874.1 | 5E−106 | 336 | 62.8 | 71.1 |
| *Aspergillus kawachii* [IFO 4308] | GAA87693.1 | 6E−106 | 336 | 62.8 | 70.8 |
| *Aspergillus fumigatus* [Af293] | XP_747808.1 | 2E−100 | 342 | 62 | 71.3 |
| *Neosartorya fischeri* [NRRL 181] | XP_001257459.1 | 5E−94 | 353 | 60.9 | 68.8 |
| *Aspergillus flavus* [NRRL3357] | XP_002380969.1 | 9E−94 | 332 | 64.2 | 70.8 |
| *Aspergillus terreus* [NIH2624] | XP_001209872.1 | 6E−93 | 344 | 62.5 | 68.9 |
| *Penicillium chrysogenum* [Wisconsin 54-1255] | XP_002566301.1 | 3E−74 | 351 | 49.3 | 58.7 |
| *Coccidioides immitis* [RS] | XP_001239027.1 | 1E−64 | 355 | 44.5 | 54.6 |
| *Ajellomyces capsulatus* [H88] | EGC49893.1 | 9E−64 | 364 | 45.9 | 58.0 |
| *Uncinocarpus reesii* [1704] | XP_002585289.1 | 6E−54 | 440 | 34.1 | 42.0 |
| *Penicillium marneffei* [ATCC 18224] | XP_002148846.1 | 1E−52 | 342 | 38 | 43.9 |
| *Botryotinia fuckeliana* | CCD44702.1 | 6E−47 | 347 | 40.3 | 51.9 |
| *Neurospora tetrasperma* [FGSC 2508] | EGO52630.1 | 2E−44 | 347 | 39.8 | 50.1 |
| *Neurospora crassa* [OR74A] | XP_964590.1 | 2E−44 | 343 | 39.1 | 50.1 |
| *Magnaporthe oryzae* [70-15] | XP_003720663 | 4E−50 | 335 | 38.5% | 50.4% |
| *Chaetomium globosum* [CBS 148.51] | XP_001222401.1 | 6E−39 | 382 | 34.0 | 45.8 |
| *Fusarium oxysporum* [Fo5176] | EGU84033.1 | 3E−38 | 350 | 34.9 | 43.4 |

TABLE 4

| | Species | Accession | NCE Forward Blast | | |
|---|---|---|---|---|---|
| | | | % Value | @ Identity | Length |
| 1 | *Aspergillus oryzae* [RIB40] | XP_001823905.1 | 0.00E+00 | 64% | 319 |
| 2 | *Aspergillus clavatus* [NRRL1] | XP_001270264.1 | 2.00E·122 | 64% | 335 |
| 3 | *Aspergillus niger* [CBS 513.88] | XP_001395874.1 | 5.00E·106 | 62% | 325 |
| 4 | *Aspergillus kawachii* [IFO 4308] | GAA87693.1 | 6.00E·106 | 62% | 325 |
| 5 | *Aspergillus fumigatus* [Af 293] | XP_747808.1 | 2.00E·100 | 59% | 336 |
| 6 | *Neosartorya fischeri* [NRRL 181] | XP_001257459.1 | 5.00E·94 | 59% | 334 |
| 7 | *Aspergillus flavus* [NRRL3357] | XP_002380969.1 | 9.00E·94 | 64% | 319 |
| 8 | *Aspergillus terreus* [NIH2624] | XP_001209872.1 | 6.00E·93 | 61% | 319 |
| 9 | *Penicillin chrysogenum* [Wisconsin 54-1255] | XP_002566301.1 | 3.00E·74 | 48% | 303 |
| 10 | *Coccidiodes Immitis* [RS] | XP_001239027.1 | 1.00E·64 | 49% | 336 |
| 11 | *Ajellomyces capsulatus* [H88] | EGC49893.1 | 9.00E·64 | 50% | 345 |
| 12 | *Uncinocarpus reesii* [1704] | XP_002585289.1 | 6.00E·54 | 47% | 423 |
| 13 | *Penicillin maneffei* [ATCC 18224] | XP_002148846.1 | 1.00E·52 | 53% | 247 |
| 14 | *Botryotinia Fuckeliana* | CCD44702.1 | 6.00E·47 | 42% | 317 |
| 15 | *Neurospara tetrasperma* [FGSC 2508] | EGO52630.1 | 2.00E·44 | 43% | 305 |
| 16 | *Neurospara crassa* [OR74A] | XP_964590.1 | 2.00E·44 | 45% | 305 |
| 17 | *Magnaporthe oryzae* [70-15] | XP_003720663 | 4.00E·50 | 43% | 309 |
| 18 | *Chaetomium globosum* [CBS 148.51] | XP_001222401.1 | 6.00E·39 | 38% | 342 |
| 19 | *Fusarium oxysporum* [Fo 5176] | EGU84033.1 | 3.00E·38 | 42% | 276 |

| | Species | EMBOSS Needle-Alignment (Global alignment) | | |
|---|---|---|---|---|
| | | Length | % identity | % Similarity |
| 1 | *Aspergillus oryzae* [RIB40] | 332 | 64.20% | 70.80% |
| 2 | *Aspergillus clavatus* [NRRL1] | 347 | 65.10% | 71.20% |
| 3 | *Aspergillus niger* [CBS 513.88] | 336 | 62.80% | 71.10% |
| 4 | *Aspergillus kawachii* [IFO 4308] | 336 | 62.80% | 70.80% |
| 5 | *Aspergillus fumigatus* [Af 293] | 342 | 62.00% | 71.30% |
| 6 | *Neosartorya fischeri* [NRRL 181] | 353 | 60.90% | 68.80% |
| 7 | *Aspergillus flavus* [NRRL3357] | 332 | 64.20% | 70.80% |
| 8 | *Aspergillus terreus* [NIH2624] | 344 | 62.50% | 68.90% |
| 9 | *Penicillin chrysogenum* [Wisconsin 54-1255] | 351 | 49.30% | 58.70% |
| 10 | *Coccidiodes Immitis* [RS] | 355 | 44.50% | 54.60% |
| 11 | *Ajellomyces capsulatus* [H88] | 364 | 45.90% | 58.00% |
| 12 | *Uncinocarpus reesii* [1704] | 440 | 34.10% | 42.00% |
| 13 | *Penicillin maneffei* [ATCC 18224] | 342 | 38.00% | 43.90% |
| 14 | *Botryotinia Fuckeliana* | 347 | 40.30% | 51.90% |
| 15 | *Neurospara tetrasperma* [FGSC 2508] | 347 | 39.80% | 50.10% |
| 16 | *Neurospora crassa* [OR74A] | 343 | 39.10% | 50.10% |

TABLE 4-continued

| | | | | |
|---|---|---|---|---|
| 17 | *Magnaporthe oryzae* [70-15] | 335 | 38.50% | 50.40% |
| 18 | *Chaetomium globosum* [CBS 148.51] | 382 | 34.00% | 45.80% |
| 19 | *Fusarium oxysporum* [Fo 5176] | 350 | 34.90% | 43.40% |

| Species | Phylum | Class | Genus |
|---|---|---|---|
| 1 *Aspergillus oryzae* [RIB40] | Ascomycota | Eurotiomycetes | *Aspergillus* |
| 2 *Aspergillus clavatus* [NRRL1] | Ascomycota | Eurotiomycetes | *Aspergillus* |
| 3 *Aspergillus niger* [CBS 513.88] | Ascomycota | Eurotiomycetes | *Aspergillus* |
| 4 *Aspergillus kawachii* [IFO 4308] | Ascomycota | Eurotiomycetes | *Aspergillus* |
| 5 *Aspergillus fumigatus* [Af 293] | Ascomycota | Eurotiomycetes | *Aspergillus* |
| 6 *Neosartorya fischeri* [NRRL 181] | Ascomycota | Eurotiomycetes | *Neasartarya* |
| 7 *Aspergillus flavus* [NRRL3357] | Ascomycota | Eurotiomycetes | *Aspergillus* |
| 8 *Aspergillus terreus* [NIH2624] | Ascomycota | Eurotiomycetes | *Aspergillus* |
| 9 *Penicillin chrysogenum* [Wisconsin 54-1255] | Ascomycota | Eurotiomycetes | *Penicillin* |
| 10 *Coccidiodes Immitis* [RS] | Ascomycota | Eurotiomycetes | *Coccidioides* |
| 11 *Ajellomyces capsulatus* [H88] | Ascomycota | Eurotiomycetes | *Ajellomyces* |
| 12 *Uncinocarpus reesii* [1704] | Ascomycota | Eurotiomycetes | *Uncinocarpus* |
| 13 *Penicillin maneffei* [ATCC 18224] | Ascomycota | Eurotiomycetes | *Penicillin* |
| 14 *Botryotinia Fuckeliana* | Ascomycota | Leotiomycetes | *Botryatinla* |
| 15 *Neurospara tetrasperma* [FGSC 2508] | Ascomycota | Sordariomycetes | *Neurospora* |
| 16 *Neurospara crassa* [OR74A] | Ascomycota | Sordariomycetes | *Neurospora* |
| 17 *Magnaporthe oryzae* [70-15] | Ascomycota | Sordariomycetes | *Magnaporthe* |
| 18 *Chaetomium globosum* [CBS 148.51] | Ascomycota | Sordariomycetes | *Chaetomium* |
| 19 *Fusarium oxysporum* [Fo 5176] | Ascomycota | Sordariomycetes | *Fusarium* |

Gap opening penalty = 10.0
Gap extension penalty = 0.5

TABLE 5

| Coding region sequences of some mtfA homologs from other fungal species |
|---|

>ANID_08741 Transcript 1 (*Aspergillus nidulans*)
ATGGATCTCGCCAACCTCATCTCCCAACCGGGGCCTGAGCCTGCTCTGACGGCC
AAATCAAGATACAGCCCTCCTGCCTTTGAACCGGGCTCCTTCTACGCCGCATCT
ACTTCATTCACGCGGACACAAGCGCCACTATCGCCTCCAGTCGAGGATAGATCT
TCTCGCTGCTCACTGCCATCAATCTCTGCGCTTCTTGACAGCGCAGACGGCGCCT
CGACACAAGCTCCAAAGCGCCAACGGCTCAGCTCTCCAATGCACCGTGAACCG
CTTGACAAGAACCCATCTGCCGGCGCTGCTCCCATCCGTCTCCCGCCCACTCCTC
CATTGCGCCCCGGCTCCGGCTTCCACAGCGCCGGCCACTCGCCCTCGAGCTCCA
TCTCATCCATCTCGATGATCAAGTCCGAGTACCCGGCACCACCATCAGCTCCAG
TCTCTCTTCCGGGCCTTCCCAGCCCAACCGACCGCTCGTCCATCTCGAGCCAAG
GGTCTGCGCCGCAGCACCAGCATGGTCCCTACGCCTCGCCAGCTCCCAGCGTGG
CGCCCTCTTACTCCTCGCCCGTTGAGCCCTCACCCTCATCGGCAATGTACTACCA
ACACCAGCGGCCCGCATCCTCAGGCACATACCAGGCTCCTCCACCCCCGCCGCA
ACACCAGCCCATGATCTCGCCCGTGACACCGGCCTGGCAGCACCACCACTACTT
CCCTCCTTCCTCAAACACACCCTACCAGCAGAACCACGACCGATATATCTGCCG
CACCTGCCACAAGGCGTTCTCGCGGCCCTCGAGTCTGCGCATCCACAGCCATAG
CCACACCGGCGAGAAGCCATTTCGGTGCACACATGCCGGATGCGGCAAAGCCT
TTAGTGTACGGAGCAACATGAAGCGCCATGAGCGCGGCTGCCATACCGGGAGG
GCTGTCGCGATGGTGTAA >AO090120000155 Transcript 1 (*Aspergillus oryzae*)
ATGGATCTCGCCAGCCTTATCACTCCGGGTCCTGAACCCATCTACAAGTCTCGG
GCATCCTACAGCCCTCCTCCCAGCTCTGCGGGTTCCTACAAGCGCCCGGCTGAA
CACGACTCTTACTTCTCGTACTCGCGCGCCCCGCAAGCCCCTCTTTCCCCGCCAG
TCGAGGACCAGCCCAAGTGCTCTCTTCCCTCTATCTCGACTCTCTTGGAAGGCG
CCGACAGCGCATCGACATATGCTGCAAAGCGTCAAAGAACCAGCCCACCCCCG
CGCAGGGAGTCTGAGTTCCGTTCACCTTATGACTCAGTCTCAACACCAAATGGC
CCTCCTACTCCACCTTTGCGCCCTGAATCGGGCTTCCACAGCGGCCACCACTCTC
CCTCTGCTTCGTCCGTGACTAGTGGAAAGGCCATCAAGCTCGAGTCGTACTCGC
AAACCCCCATGACACTGCCTAGCCCGTCCGATAGATCCTCGATCTCCAGCCAGG
GCTCTGTCCACCACGTTTCCGCTGCTCCCTACGCTTCTCCTGCCCCCAGTGTGGC
CTCGTACTCTTCGCCGGTTGAATCCTCGGCTCCGTCCGCCATGTACTACCAGAG
ACCTTCCGGCTCCTACCAGACCCCCGCTACTGTGCCTAGCCCCTCCGCTGCTCCT
ATGCCTGCATCTGCCACACACCAGCAGATGATTACTCCCGTCACTCCGGCCTGG
CAGCACCACCACTACTTCCCGCCTTCCAGCTCGGCACCCTACCAACAGAACCAC
GACCGGTATATCTGCCGGACTTGCCACAAGGCCTTCTCCAGACCATCCAGCCTG
CGCATCCACTCTCACAGCCACACTGGCGAGAAGCCATTCCGCTGCACCCACGCC
GGCTGCGGTAAGGCGTTCAGCGTACGAAGCAACATGAAGCGCCACGAGCGCGG
CTGCCACACCGGACGCCCCGTCGCCACCGCCATGGTATAA >ACLA_097790 Transcript 1 (*Aspergillus clavatus*)
ATGGATCTCGCAAACCTCATCTCGCATCCCACCTCCGAGGCTGCCTCGACTTTC
AAGTCGAGGTCAGCTCAGAGTCCTCCCGCCTTTCAAGCGAACCCTTACAAGCGT
CTCTCCGGATCGTCGATGAGCTCTTACTTCACCTCCGTACCGACGACCGCGACA TABLE 5-continued

| Coding region sequences of some mtfA homologs from other fungal species |
|---|
| TCGTATTCTCGCACCCCGCAGCCACCACTCTCCCCACCCGTCGACGACCGGCCC<br>AGATGTTCGCTGCCCTCAATCTCGACTCTACTGGAGGGTGCAGACAGCGCAGCC<br>GCACATGCAGCGAAACGCCAAAGAACTAGCCTCTCGGCGCATAGGGATCTTGA<br>TGCCCGTCCTCAGTCGCAACCGTATGACACGATCACCCCACATGCCTTGCCACC<br>TACGCCGCCATTGCGTCCTGGCTCGGGTTTTCGCAGCAACGGCCATTCGCCTTC<br>AGCCTCGTCTGTTTCCGCAACGAGCGCCAGCACGGTGATCAAGACCGAAACAT<br>ATCCTCAGCCTCACATCGGCCTTCCCAGCCCGACAGATCGCTCCTCCATCTCCA<br>GCCAAGGATCGGTGCAGCATGCGCCCGGAGCGCCGTATGCGTCGCCAGCGCCT<br>AGCGTGGCATCTTACTCGTCACCTGTCGAGCCTTCCACACCGTCCAGCGCAGCC<br>TACTATCAAAGAAAGGCCCCTTCAGCTCCCTTCCAGAACCCAGGCAGCGTCCCC<br>TCAGCATCGGCCGCTCACCAGCAGCTTATCACCCCCATCACCCCCGCCTGGCAA<br>CACCACCACTATTTCCCCCCATCCAGCTCAACCGCCTACCAGCAGAACCATGAT<br>CGCTACATCTGCCGCACCTGCCACAAAGCGTTCTCGCGCCCTTCCAGTCTGCGC<br>ATCCACTCCCACAGCCACACGGGCGAGAAGCCCTTTCGCTGCACACACGCCGGC<br>TGCGGCAAGGCCTTCAGCGTGCGAAGCAATATGAAGCGCCATGAGCGTGGATG<br>CCATACAGGCCGCCCAGTCGCCACTGCTATGGTGTCATAA |
| >gi\|317033475: 64-1041 *Aspergillus niger* CBS 513.88 C2H2 finger domain protein, mRNA<br>ATGGATCTCGCCAGCCTCATCTCCCACCCGGGACCCGATCCCATCATGAAGTCT<br>AGAGCCTCATACAGCCCTCCCATGACTTCCTACAAGCGCTCCATCGAACACACC<br>TCGGACTCCTACTTCCCCTCCGTCCCGATCTCCTACACCCGCTCCCCGCAGCCTC<br>CTCTCTCCCCGCCTGTCGAGGACCAGTCCCCCAAGTGCTCTCTTCCCTCCATCTC<br>TACCTTGCTCGAGGGCGCAGATGGCGCAGCTATGCATGCAGCAAAGCGCACTA<br>GAATGACCCCTCCTCTGCAACGCGACCTTGATTCCCGCCAACAGTCGCAAGCAT<br>ATGACCTCAAAGCTAACGGCCCCCAAATCGCCTTGCCCCCCACCCCCCCATTGC<br>GCCCCGGTTCTAGCTTCCACAGCGCCGGACACTCCCCCGCCTCCTCCATCTCTGC<br>TGCCAGCGATGCTGCTGCGCCCAAGCGCTCCGACTCCTACCCTCAAGTGCCCAT<br>GGCTCTGCCTAGCCCCTCGGATCGCTCGTCCATCTCCAGCCAGGGTTCAGTTCA<br>GGGTGTCTCCAGTGCTTCCTACGCTTCTCCCGCTCCCAGCGTCTCTTCCTACTCC<br>TCTCCCATTGAGCCTTCGGCCTCGTCCGCCATGTTCTACCAACGCACGGCTCCCT<br>CCACTTCCGCCGCTCCTCTCCCGACGCCAGCAGCACCGCAACAGATTATCTCCC<br>CTGTGAACCCTGCCTGGCAGCACCACCACTACTTCCCTCCCTCCAGCACCACGC<br>CCTACCAGCAGAACCATGATCGCTATATCTGCCGCACCTGCCACAAGGCCTTCT<br>CGAGACCCTCCAGCCTGCGCATCCACTCCCACAGCCACACGGGCGAGAAGCCC<br>TTCCGCTGCACCCACGCCGGTTGTGGGAAGGCCTTCAGCGTGCGCAGCAACATG<br>AAGCGTCATGAGCGTGGCTGCCACAGTGGTCGGCCCGTCGCAACCGCCATGGTT<br>TAA |
| >(gi\|358370982: 305608-305869, 305944-306659) *Aspergillus kawachii* IFO 4308 DNA, contig: scaffold00014, whole genome shotgun sequence<br>ATGGATCTCGCCAGCCTCATCTCCCACCCGGGACCCGATCCCATCATGAAGTCT<br>AGAGCCTCATACAGCCCTCCCATGACCTCTTACAAGCGGTCCATCGAACAGACT<br>TCCGACTCATACTTCCCCTCCGTCCCGATCTCCTACACCCGCTCCCCGCAGCCTC<br>CTCTCTCCCCGCCTGTGGAGGACCACTCTCCCAAGTGCTCTCTTCCTTCCATCTC<br>TACCTTGCTTGAGGGCGCAGATGGCGCAGCTATGCACGCAGCAAAGCGTACTA<br>GAATGACCCCTCCTCTGCAGCGCGACCTTGATTCCCGCCAACAGTCGCAAGCAT<br>ATGACCTCAAAGCCAACGGCCCCCAAATCGCCCTGCCCCCCACGCCCCCATTGC<br>GCCCTGGGTCTAGCTTCCACAGCGCCGGCCACTCCCCCGCTTCCTCCATCTCTGC<br>TGCCAGCGATGCTGCTGCGCCCAAGCGCTCCGACTCCTACCCTCAAGTGCCCAT<br>GGCTCTGCCTAGCCCTTCGGATCGGTCGTCCATCTCCAGCCAGGGTTCCGTTCA<br>GGGTGTCTCCAGCGCTTCCTACGCTTCTCCCGCGCCCAGCGTCTCTTCCTACTCC<br>TCTCCCATTGAGCCTTCGGCCTCCTCCGCTATGTTCTACCAGCGCACGGCGCCTT<br>CCACTTCGGCCGCTCCTCTCCCGACACCGGCAGCACCGCAACAGATTATCTCCC<br>CTGTGAACCCTGCCTGGCAACACCACCACTACTTCCCTCCCTCCAGCACCACGC<br>CCTACCAGCAGAACCATGATCGCTATATCTGCCGCACCTGCCACAAGGCCTTCT<br>CGAGACCTTCCAGCCTGCGCATCCACTCCCACAGCCACACGGGCGAGAAGCCCT<br>TCCGCTGCACCCACGCTGGTTGTGGGAAGGCCTTCAGTGTGCGCAGCAACATGA<br>AGCGTCATGAGCGTGGTTGCCACAGTGGTCGGCCCGTCGCAACTGCCATGGTAT<br>AA |
| >Afu6g02690 Transcript 1 (*Aspergillus fumigatus*)<br>ATGGATGTCGCAAGCCTCATCTCGCCTTCTGAATCGGATACTGTCCCGACCTTC<br>AGGTCAAGATCGATTCAGAATTCATCAGCCAGCCATTACAAGCGCCTCTCCGAA<br>CAATCAACAGGCTCTTACTTCTCTGCTGTGCCAACACATACAACGTCTTACTCTC<br>GTACCCCTCAGCCACCACTGTCCCCTCCAGCGGAGGACCAGTCCAAATGCTCGC<br>TTCCTTCCATCTCGATCCTGCTTGAGAACGCAGACGGTGCCGCCGCACACGCAG<br>CAAAACGCCAACGAAACAGCCTATCAACGCACAGGGATTCGGATCCCCGGCCT<br>CCATATGACTCGATCACACCACACGCCATGCCGCCAACGCCGCCATTGCGTCCC<br>GGTTCGGGCTTCCACAGTAATGGCCATTCTCCCTCGACATCATCTGTCTCTGCCG<br>CTAGCTCCAGCGCTTTGATGAAAAACACAGAATCGTATCCTCAGGCGCCAATTG<br>GGCTTCCTAGTCCAACGGATCGATCCTCGATCTCGAGCCAAGGGTCCGTTCAGC<br>ATGCCGCCAGCGCTCCATATGCTTCGCCTGCTCCCAGCGTATCGTCCTTCTCTTC<br>TCCCATCGAGCCCTCTACACCATCAACTGCCGCTTACTACCAAAGAAATCCTGC<br>GCCGAACACCTTCCAAAACCCAAGCCCCTTCCCCCAAACATCCACAGCATCTCT<br>TCCCTCCCCGGGTCATCAACAGATGATTTCTCCCGTCACCCCCGCCTGGCAACA |

TABLE 5-continued

| Coding region sequences of some mtfA homologs from other fungal species |
|---|
| TCACCACTACTTCCCCCCGTCCAGTTCCACGTCTTACCAGCAGAACCATGATCG<br>CTACATCTGCCGGACATGCCACAAGGCCTTTTCGCGGCCCTCCAGCCTGCGCAT<br>CCACTCCCACAGCCACACTGGCGAGAAGCCTTTCCGTTGCACACATGCCGGCTG<br>CGGCAAGGCCTTCAGCGTACGGAGCAATATGAAGCGTCATGAGCGTGGTTGCC<br>ATACGGGCCGCCCAGTTGCTACCGCCATGGTCCAATAG |
| >NFIA_049000 Transcript 1 (*Neosartorya fischeri*)<br>ATGGATGTCGCAAGCCTCATCTCGCCTTCTGAATCGGATACAGTTCCGACCTTC<br>AGGTCAAGATCGATTCAGAATTCATCAGCCAGCCATTACAAGCGCCTCTCCGAA<br>CAATATACGGGCTCTTACTTCTCTGCTGCACCAACACATACGACGTCTTACTCTC<br>GTACCCCTCAGCCACCACTGTCCCCTCCAGCCGAGGACCAGCCCAAATGCTCGC<br>TTCCTTCCATCTCGATTCTGCTTGAGAACGCAGACGGTGCCGCCGCACACGCAG<br>CAAAACGCCAAAGAACCAGTCTATCAACGCACAGGGATTCGGGGCCTCCATAT<br>GACTCGATCACACCACACGCCATGCCACCAACGCCGCCACTGCGTCCTGGTTCG<br>GGCTTCCACAGTAATGGCCATTCTCCCTCGGCATCGTCTGTCTCTGCCACCAGCT<br>CCAGCGCTGTGATGAAGAACACCGAAACGTATTCTCAGGCGCCAATTGGGCTTC<br>CTAGTCCGACGGATCGATCCTCGATCTCGAGCCAAGGGTCCGTTCAGCATGCCG<br>CCGGCGCTCCATATGCTTCGCCTGCTCCCAGCGTGTCGTCCTTCTCTTCTCCCGT<br>CGAGCCCTCTACACCATCAACTGCCGCTTACTACCAAAGAAACCCTGCGCCGAA<br>CACCTTCCAAAACCCAGGCTCCTTCCCTCCAACATCCGCGGCCTCTCTTCCTTCC<br>CCGGGTCATCAACAGATGATTTCTCCCGTCACCCCCGCCTGGCAACATCACCAC<br>TACTTCCCCCCGTCCAGTTCCACGCCTTACCAGCAGAACCATGATCGCTACATCT<br>GCCGGACATGCCACAAGGCCTTCTCGCGGCCATCCAGCCTGCGCATCCATTCCC<br>ACAGCCACACTGGCGAGAAGCCTTTCCGCTGCACACATGCCGGCTGCGGCAAG<br>GCCTTTAGCGTACGGAGCAATATGAAGCGTCACGAGCGTGGTTGCCATACGGG<br>CCGCCCGGTTGCTACCGCCATGGTCCAATAG |
| >AFL2G_ 08180 Transcript 1 (*Aspergillus flavus*)<br>ATGGATCTCGCCAGCCTTATCACTCCGGGTCCTGAACCCATCTACAAGTCTCGG<br>GCATCCTACAGCCCTCCTCCCAGCTCTGCGGGTTCCTACAAGCGCCCGGCTGAA<br>CACGACTCTTACTTCTCGTACTCGCGCGCCCCGCAAGCCCCTCTTTCCCCGCCAG<br>TCGAGGACCAGCCCAAGTGCTCTCTTCCCTCTATCTCGACTCTCTTGGAAGGCG<br>CCGACAGCGCATCGACATATGCTGCAAAGCGTCAAAGAACCAGCCCACCCCCG<br>CGCAGGGAGTCTGAGTTCCGTTCACCTTATGACTCAGTCTCAACACCAAATGGC<br>CCTCCTACTCCACCTTTGCGCCCTGAATCGGGCTTCCACAGCGGCCACCACTCTC<br>CCTCTGCTTCGTCCGTGACTAGTGGAAAGGCCATCAAGCTCGAGTCGTACTCGC<br>AAACCCCCATGACACTGCCTAGCCCGTCCGATAGATCCTCGATCTCCAGCCAGG<br>GCTCTGTCCACCACGTTTCCGCTGCTCCCTACGCTTCTCCTGCCCCCAGTGTGGC<br>CTCGTACTCTTCGCCGGTTGAATCCTCGGCTCCGTCCGCCATGTACTACCAGAG<br>ACCTTCCGGCTCCTACCAGACCCCTGCTACTGTGCCTAGCCCCTCCGCTGCTCCT<br>ATGCCTGCATCTGCCACACACCAGCAGATGATTACTCCCGTCACTCCGGCCTGG<br>CAGCACCACCACTACTTCCCGCCTTCCAGCTCGGCACCCTACCAACAGAACCAC<br>GACCGGTATATCTGCCGGACTTGCCACAAGGCCTTCTCCAGACCATCCAGCCTG<br>CGCATCCACTCTCACAGCCACACTGGCGAGAAGCCATTCCGCTGCACCCACGCC<br>GGCTGCGGTAAGGCGTTCAGCGTACGAAGCAACATGAAGCGCCACGAGCGCGG<br>CTGCCACACCGGACGCCCCGTCGCCACCGCCATGGTATAA |
| >ATEG_07186 Transcript 1 (*Aspergillus terreus*)<br>ATGGATCTCGCCAGCCTAATCACCCCGGGACCTACTCCCTTCGCATCTCGTCCG<br>CCTCGAGCTTCCTACAGTCCCCCGGCTTCTTCGTCCGGTTCATACAAGGCCCCTA<br>ATGAGCCTCATTATACGGGGTCATACTTCCCCGCCATGCCTACTGCGACTCCAG<br>TGACCACCACTACTTCCTACTCGCGCTCGCCGCAACCGCCTCTCTCTCCTCCCGT<br>CGAGGACCAGCCCAAGTGCTCTCTCCCTTCCATCTCCACCCTTCTCGGTGCCGCA<br>GACAGCGCCCCAATGCCCCCAGCTAAGCGCCAGCGCCTCAGTACCCCCGCGCG<br>CAGAGAATCCGATAGCTGGCTCCAGACAACACCATGCCTGCCTCCGACCCCCCC<br>GTTGCGTCCAGGCTCCGGCTTCCACAGCAGCGGCCACCGCTCGCCATCATCCAA<br>CAAGCCCACCGAATCGGCGCCCTTCCCGCAACAGCCCCCCGTGACGCTCCCCAG<br>TCCCACCGAGCGCTCCTCCATCTCCAGCCAGGGCTCCGCGCACGCGCCGTACGC<br>TTCGCCCGCCCCCAGCGTCGCCTCGTACTCGTCTCCCGTCGAGCCCTCCCCGGCT<br>CCCTCCACGCTGTACTACCAGCGCCCCGCCGCGCCTCCAGCGCCTTCCGCCGCC<br>GCCGCTGCTCCCGCTCCCGCGCAGCCCTTGATCTCCCCCGTCACCCCGGCCTGG<br>CAGCACCACCACTACTTCCCGCCCTCCAGCTCCACCCCCTACCAGCAGAACCAT<br>GACCGGTACATCTGCCGTACCTGCCACAAGGCATTCTCGCGCCCCTCGAGTCTG<br>CGCATCCATTCGCACAGTCACACCGGCGAGAAGCCCTTCCGCTGCACCCACGCC<br>GGCTGCGGCAAGGCCTTCAGCGTCCGCAGCAACATGAAGCGCCATGAGCGCGG<br>ATGCCACAGCGGCCGTCCGGTTGCTACCGCTATGGTATGA |
| >gi\|255951067\|ref\|CM_002566255.1\|*Penicillium chrysogenum*<br>Wisconsin 54-1255 hypothetical protein (Pc22g24110) mRNA,<br>complete cds<br>ATGGATCTCTCCAACCTCCTCTCTCACAGCGCGGCTGTCAAGCCGATCTATACTC<br>CTGTCGAGTCCAGTTACTATAAGCGCTCGCCGCCTCTGTCGCCGCCAGCCGAAG<br>AGCCCAAGGTCTCATTGCCTTCAATCTCGTCTCTCTTTGAGGGTGCTGATGGTGC<br>TCAGCACGCAGCTACCTCGCTAACCCTAAACCTTCCAGAGCGCCAACGCTTGTC<br>ACCATCTCTCGGTGACCGCCATGTCCGGGTTCAGTCCTACGAACTGCCCCCAAC<br>ACCACCTCTGCGCCCCGGCTCTGGCCACGCCCACCGCCGCGCATCTCCCGTGGA<br>GTCGCTGTCTCACAAGGAAGCACACCAGCATCACCTTCACCGTTCCTCTATCTC |

TABLE 5-continued

Coding region sequences of some mtfA homologs from other fungal species

CAGCAACAGCTCAGTCCACATCCCTCGCAACACAGTACCCTACGCCTCGCCTGT
ACCAAGCGTCTCATCCTACACATCTCCAGTCGACGCTCCTCAACAGCCAATGTA
CTACCCTCGCCCACCAACCACATCCTCCTTCCAGCCCTCAACACCAGCATCAGC
ACCCCAGATGCCCCCTGTCCAGGTCCAGACGCAGCAGCCGCACTCGCACTCTCA
CTCGTCTTCGGCTCTCATCTCTCCTGTCACCCCGGCCTGGCAACACCACCACTAC
TTCCCGCCCTCCACCACAGCCCCGTACCAGCAGAACCACGACCGCTATATCTGC
CGTACATGCCACAAGGCTTTCTCGCGCCCTTCCTCCCTGCGCATCCACTCGCACT
CGCACACTGGCGAGAAGCCCTTCCGCTGCACGCATGCCGGCTGCGGTAAGGCTT
TCTCCGTGCGCAGTAACATGAAGCGCCATGAGCGTGGCTGCCATTCTGGTCGCC
CTGCCCCTGCCCCTGCTGCTACTGCGCTTGTCGTATAG

>gi|119173021|ref|XM_001239026.1| *Coccidioides immitis* RS hypothetical protein (CIMG_10049) partial mRNA
ATGAACGTTTCAAGCCTGATCACTTGCGATCAGCCGCACCAATTGCGCGCGCCT
GCATCTTCATATTCTGAGCACCGTCGATCCCCATCCATCCCCAAGCCTTTGCAGA
CGGAGAGCAGTTCATGCGCTTCTCCATACTCGCGGTTCGAGCGTCTCCCTCTTTC
ACCGCCGGAGGAGGATGGCAAGACACAGTTCTCACTTCCTTCTATCTCGTCTCT
TCTTCGGGGCGTAGATGGTGTTTCTGATGCGCACGTTGCTAAGAGACAACGAAC
CAACCCTCCTCCTAGCATTGACTTAGGGATGGAGAGACGGACTATAGACCAAA
CATTAAAGCAGAGGCCAGCGCTGCCTTTGACGCCTCCTCTAAGGCCTGAGTCTG
GCATGAATAGCACAAGCCAGTCGCCGTCAACATCATCGCCACCACGAAGCGCC
ATCTCACTACCGAGTCTTGTTCGGAGTTATCCGTCTCCAGTTTCAGAAGTTCCAG
AGGGACGACGGATGTCACAGATATCGCGACATTCGCGAGGGGCTTCGACGTCG
CAAACTTCTCAACTTTCAGGCCCAGAAACACGTTACCCATCGCCACCAAATGTC
AACTCTCCAACCTTTGCTGCCCCTGTTGAACCAGCGCCAAAGCCGACAGAATAC
TACCCAGCCAGCCGACCGGTAACGTTTCCGCCTGTGGCGTTCGCAGTTCTGCCA
AGCCAGCCAACTCATCCTCAGGTGCTTCCTCTTGGAAGTCCTGCGTGGCAGCAC
CATCATTATTTCCCTCCTTCCAACACAGCAACTTATCCTCTCAATCACGATAGAT
ACATCTGCCGAATATGTCATAAGGCTTTCTCAAGACCGTCCAGCCTGCGAATAC
ACTCCCACAGTCATACTGGCGAGAAGCCTTTCCGGTGCCCCCATGCCGGCTGTG
GGAAAGCG1TTAGCGTGCGAAGCAACATGAAGCGACACGAAAGGGGTTGCCAT
CCTGGAAGATCAGCACCACCATCGGCCCTGGTTAACTGA >(gi|198250550: c746647-746377, c746321-745555) *Ajellomyces capsulatus* H88 supercont1.9 genomic scaffold, whole genome shotgun sequence
ATGAATTTATCCCACTTGGTGACCAGCTATCATAGCCCTCCTTCGACGTATCCAC
ACTCAGGCACTTCGCAAAAGCGCCAGTCCTTGCAGAGCGAATCTTCATTATCTG
TATCGAACGGATACTACGATCGCAATGCTTCAAATCTTGCATATGCCCGCTCTC
CTCAACCACCCTTATCCCCACCTGTCGAAGAGCAGTCCAGATTCTCTCTTCCTTC
AATATCTAGTTTATTGCAAGGAGCTGACCAACTCTCTCCTGTTCATATAGCTAA
AAAACATCGTCCCAATCCACTCTCAACTGGAGAAGTTGATTTAAAATCGCAGGG
CCATGGAGCCACCCAAAAGCCCATACACAGGCCGAGAATGATTTTACCACCGA
CCCCTCCCATGCGCCCAGGCTCCGGATTAGATGGAAGAAATCACTCTCCTGCCG
GATCGTCGCCATCGTCTGCACACTCTCCCATTTCAGTAGCCAATCTCACAAGTTC
GTCATCGGCGGACCCTTCCTATCAGCATCGGATGCCCCAAGGTCCGTTACCCCC
ACAGTCAACCAGATCGTCCGTATCTCAAAATTCTCCTGTCTCTCTACCCGAAAA
GCATTACGCTCCATCCTCCAATTTACCCACCAGCTCGACTCCATTCGCTTCCCCA
GTTGAACCCCTAGCGAATTCTACGGAATATTATCACCGCCCATCCCATCCCCCTT
CTTTCTCGACATCTATTCCTCTGGCAGCCCCGCCAGCGCAACAGCACCATCACC
ATTCTATGATCTCAACCTGGCAACACCACCACTATTTTCCACCGTCAAATACGG
CTCCCTACCCACAAAATCATGACAGGTATATCTGTCGAATATGTCACAAGGCGT
TTTCTCGGCCTTCTAGTCTGCGGATTCACTCGCACAGCCATACCGGCGAAAAGC
CATTCAAATGCCCGCATGTCAACTGTGGCAAGTCATTTAGTGTCAGGAGTAACA
TGAAGCGACATGAACGGGGTTGTCATACAGGCAGACCTACGCAAGCAGGTTTG
GTGAATTAA >gi|258569089|ref|XM_002585243.1|*Uncinocarpus reesii* 1704 conserved hypothetical protein, mRNA
ATGAACGTTTCTAGCCTGATTAGTTGTGATCAGACTGCTCCCTTCCACGGGTCTG
CAACATCATATTTCGAGCATCATCAAAGAATCCGATCGCCTTCCATTCCCAAAA
GATCACACGAAGAGAACAGCTCATCCGCCTCTCCCTACCCTCCTTTTGCAACCC
TGCCTCTTTCGCCACCAGAAGATGACGGGAAGACAACCTTCTCGCTTCCTTCTA
TCTCATCCCTTCTTCAAAGCGTCGACGCTGCTTCTGACACTCACGTTGCCAAACG
GCAACGAGCCAACCCCCCTCCTAGCATTGATTTAGCTCTGGAGAGACGAGGTGC
CTGTGCGGACCAAGCAATCAGACAAAGGCCAGCCCTTCCACTAACGCCTCCCCT
GCGACCAGAGTCGGGAATGGGCGGTGTAAATCACTCGCCATCTGCATCATCCCC
TCCCCGAACCGCTATCTCACTACCCAGCCTCATTGGAAGTTACCCATCGCCAGT
TTCAGAGGCTCCAGAAGGACGACGAATGTCGCAAATCTCACGACACTCAAGCA
GAACTTCCATCTCTCAATCCTCCCAACATCCAGGGCCGGAAGCCCGCTACCCAT
CGCCACCAACTCTCAGCTCTCCTTCCTTCGCCGCTCCTATTGAACCACCTCCAAA
GCCAGAGTACTACTCTTCTGGTGCCCGACCGACCAACTTTCCGCCAGTAACTTT
CGCTGTCCTTCCAAGTCAACCAACGCATCCGCAGATGGTGGCCTTGGGGAGTCC
TGCCTGGCAGCATCACCACTACTTTCCTCCATCAAACACAGCAACTTACCCACT
CAACCACGACAGATACATTTGCCGAATATGCCACAAGGCATTCTCACGGCCGTC
AAGCCTGCGAATTCACTCGCATAGTCACACAGGCGAGAAGCCGTTTCGATGCCC
CCATGCCGGCTGCGGGAAGGCATTCAGCGTGCGAAATCAGCCCCGCAGCCAGC TABLE 5-continued Coding region sequences of some mtfA homologs from other fungal species GCTCGTTAATTGAAAAACGGAAGGGGTACGCGATCGGATTTGACGAATGGGTT
TTGACGATGATAACGCCCACAATACGGAGTACCAACGAGCAAATCTACACAAC
TGCATCGTGTAAGATCGCGAACGTGGCGGTGATCAACATCAATAGAAGAATTG
CCGAGCTTCGCAAGTCATTTCGCAACAGACGTTCGAATGGGACGTTGTCCCCGA
CGAAGCGCCGCGTCAAATTGGCATTTTCCCTGGATTGCCAATCTACATCCTCAT
CCAGGCTTGCCCTTTTACCGCAGTCCCTTTGA >gi|212537380: 615-1358 *Penicillium marneffei* ATCC 18224
C2H2 finger domain protein, putative, mRNA
ATGGATAACGTGCCTGCAAGCAAACGTGCCCGCCATGACTCAGGCGACTACAG
CCGTGGCTTCTTACCTCCAACACCGCCAATGCGCCCCTGCTCCGGGTTCACAGA
AGGCAGCTCGCCTGCCTCTCTTCCTTCTGGACGATCACATTCTGCTTCTATAAGC
AGCGCAGTTTCGCATCCATCACACCAACAGCGTACATCTTTACCATCTATTTCTG
CATCTCTTCAAAATACACCAATCCACCCTTCAGAGCGTTTATCCATCTCCTCTCT
CGCCTCTCACGACTCTTCCCGCCTTTCTCACGCCATTCCCAGCCCTTCATCTACC
ACAGCCTCGATCACAACCACAGCGACTCCATCAACGTCATATTATTCTACATCA
GAAGAGAAAGCATATCCACGATCACATAGCACATCCGCTCCAGTGACCCCATC
AACACTTGTCCCACCACCACCCGCCATGCTCTCGCCTGTGAACCACCCAGGCTG
GCAACACCACCACTACTTCCCACTTTCGACTACGACATCATACCCACAAAACCA
CGAGCGGTATGTCTGCCGTACATGCCACAAGGCATTCTCTCGTCCATCCAGTCT
TCGAATCCACTCGCATAGCCACACTGGCGAGAAGCCATTCCGATGCACACATGC
AGGCTGCGGAAAGGCGTTCAGTGTGCGCAGCAATATGAAGCGCCACGAGCGCG
GCTGTCATAGCGGACGACCTATGACGGCAACTGTTGTCTAA >(gi|325974178: c673869-673659, c673604-673177,
c673115-672801) *Botryotinia fuckeliana* isolate T4
SuperContig_50_1 genomic supercontig, whole genome
ATGGCCTCATCGTTGGTTTCAAACCCTTATACAGTCCATCCTATGGCTCAACACT
CTTCCTACACATACGTTAACGCACCTCAACCACCACCCTCACCACCCGTAGACG
AAACTTCAAAGTGTTCCCTACCATCTATTTCAAGTCTGTTGGGTTTGGCCGATGG
ATCGAGTCCAACAGAGCAGGCTCAGCAACAGTCATCGCCACAACAAGCAGCTT
TCAAGGAAGATTATAGACCAGAGTCTGGACATCAGTACGGTCCTTCCTCATCAA
TGAGCTCTCGAGGTGCTCTTCCACCTACACCCCCAATGCAATCTGACGGTGGAT
TCGACGGCAGACAATCGCCGTCTCAAGCATCTACTTCATCATATTCAGTAGTTT
CTGCGCCAAATTATTACTTTAATCCTTCTCAAGTCTCGGCCATCAACAATATGGA
GCCTCATGCACAACGCCAGCCAGTCCAAACTGTTACTCGAAGAGTTTCAATGCC
AGTGTCTTCAATGCAATATGGCCATTCTCCGTTCAACGGATCCTACACTATGTCT
CCTGGCGCCCAGTCTTTGAGCTCTTACTATCCAAGCCCGATACAAACACAATCT
CCCCAAGTTTCTTCACTATACTATCAAAGACCACTTCCACAGCAATTTCCTCCGC
CAATGATGCCAGTGTCTGTGACTCTGACTCCATCATCCGGTGCTAATCCATGGC
AACATCATCACTATATCTCTCCTTCCTCAGCAGCCTCATTTCCTCAGTCACAAGA
TAGATACATCTGTCAGACTTGTAACAAAGCTTTTTCGAGACCATCGAGTCTCCG
AATCCACAGCCACTCACATACCGGCGAGAAACCCTTCAAGTGTCCACATCAAA
ACTGTGGGAAAGCCTTCAGCGTTAGGAGCAACATGAAGAGACACGAGCGAGGT
TGTCACAGTTTTGAAAGCGCTTCAATGGTCTGA >ENA|EGO52630|EGO52630.1 *Neurospora tetrasperma* FGSC 2508
hypothetical protein: Location: 1 . . . 1000
ATGGCACCCACGACGTTAACGCCTCAATATCCTGCCCAGCCTTATGGCTTCGCT
CCGCCACCCTCCCCTCCTTTGGACGACTCCAACAAGTGCTCCCTGCCCTCGATTT
CGAACCTGCTTGTCATGGCCGATCAGGGATCTCCTACCTCAGAGACATCTCCTC
AGTCTCAGCAATTGCACTTCTCAAAGCCTGACAACCGTCCCAACTCTTCCCAGT
TTGGCAACCCAGCATCGATCAGGGCGAACCTCCCCCCTAGTCCTCCCATGTCTT
CGGAAGCTTCTTTTGAAGGATACCGCTCTCCTTCAAGCAAGCCAGCAAGCCAGT
CTCAGGGCAGCTCCAACTACTACTATGAGACCACGCCGCCTTTGAGCCAGCATG
AAGCCGACTCCCGGCAGATGGCCACTGCTGCACCCAGAGCCCCTGTTCAGTCAT
CAACCTTCCAAACACAGTACCCGTCGTCAGCCGGCTACTCGAGTCAGTCAGGCA
TGAACCCTTATTACCCTCCCATGCAGCCGACACCCCCTCCGCAGCAGCAGATGT
CGGGCTTGTATTATCAGCGACCACTCCCTCAGACTTTCACCCCTGCTGTGCCAGT
TCCAGTCACTCTCGCACCAGTCACGGGAGCCAACCCTTGGCAACATCACCACTA
TATTGCTCCTTCTTCCACTGCATCTTTTCCGCAGTCTCAAGACCGGTACATCTGC
CAGACTTGCAACAAGGCCTTCTCTCGACCGAGCTCATTGCGAATCCACAGCCAC
TCTCACACTGGTGAGAAGCCTTTCAAGTGCCCCCATGCAGGCTGCGGAAAGGCC
TTCAGCGTTCGCAGTAACATGAAGCGTCATGAGCGTGGCTGCCACAGTTTTGAG
AGCAGCAACGGCAGAAGCAGTGGCAACAGCAACAACGGCGCATCTGCCTAG >gi|85113804|ref|XM_959497.1|*Neurospora crassa* OR74A
hypothetical protein partial mRNA
ATGGCACCCACGACGTTAACGCCTCAATATCCTGCCCAGCCTTATGGCTTCGCT
CCGCCACCCTCCCCTCCTTTGGACGACTCCAACAAGTGCTCTCTACCCTCGATTT
CGAACCTGCTTGTCATGGCCGATCAGGGATCTCCTACCTCAGAGACATCTCCTC
AGTCTCAGCAATTGCACTTCTCAAAGCCTGACAACCGTCCCAACTCTTCCCAGT
TTGGCAACCCAGCATCGATCAGGGCGAACCTCCCCCCTAGTCCTCCCATGTCTT
CGGAAGCTTCTTTTGAAGGATACCGCTCTCCTTCGAGCAAGCCAGCAAGCCAGT
CTCAGGGCAGCTCCAACTACTACTATGAGACCACGCCGCCTTTGAGCCAGCATG
AAGCCGACTCCCGGCAGATGGCCACTGCTACACCTAGAGCCCCTGTTCAGTCAT
CAACCTTCCAAACACAGTACCCGTCGTCAGCCGGCTACTCGAGTCAGTCAGGCA TABLE 5-continued

| Coding region sequences of some mtfA homologs from other fungal species |
| --- |
| TGAACCCTTATTATCCTCCCATGCAGCCGACACCCCCTCCGCAGCAGCAGATGT<br>CGGGCTTGTATTATCAGCGACCACTCCCTCAGACTTTCACCCCTGCTGTGCCAGT<br>TCCAGTCACTCTCGCACCAGTCACGGGAGCCAACCCTTGGCAACATCACCACTA<br>TATTGCTCCTTCTTCCACTGCATCTTTTCCGCAGTCTCAAGACCGGTACATCTGC<br>CAGACTTGCAACAAGGCCTTCTCTCGACCCAGCTCATTGCGAATCCACAGCCAC<br>TCTCACACTGGTGAGAAGCCTTTCAAGTGCCCCCATGCAGGCTGCGGAAAGGCC<br>TTCAGCGTTCGCAGTAACATGAAGCGTCATGAGCGTGGCTGCCACAGTTTTGAG<br>AGCAGCAACGGCAGAAGCAGTGGCAACAGCAACAACAGCGCATCTGCCTAG |
| >gi\|389646062: 228-1157 *Magnaporthe oryzae* 70-15<br>hypothetical protein (MGG_12536) mRNA, complete cds<br>ATGGCCGCCACCATGATACAACAGCCCTACCCAATTCATCAGCAGCAGTCGCAG<br>TACAGCTACATGGTTCAGCCTCAGGGCCCGCCTTCGCCGCCCATGGACGACAAC<br>AAGTGCTCGCTTCCATCCATCTCGAACCTGCTCGGCTTGGCGGATCAAGGATCA<br>CCAACCTCGGAGACCTCGGCCCAATTCCGCGAGGAGCAGAAGCAACAACAAGC<br>AGCACAACAATCAAGACCCAACTCGTCACACTATAGCAATGCAGTCCAGTCTGT<br>GCGCCAGGGCATCCCGCCAACGCCGCCAATGACTTCTGAGACCTCATTCGACGG<br>TTACAACTCGCCCTCAAACAAGTCGGTCAGCCAGCTTCCCGCCACTGGCTACTA<br>CTTTGAGGCGACGCCACCCCCAGGCCACATGGAGATGGAGCCCCGCCCGCACA<br>TGACCAGCGTTTCCAGGGTCCCAGTTCAGGCTCCCTTCGCTCAGTCTGCCTACTC<br>AGCTCCCTATGGCATGGCCCCCAGCAACCCGATGGCGGCCTACTACCCGACGAT<br>GCAGCCCACGCCTCCTCCTCAGCAGCCTCAGATCTCTAGCCTTTACTACCAGAG<br>ACCCCTTCCTCAGGCCTTCCCTCCCATGCCTGTCAACGTCTCCATGGGTCCTCAG<br>TCTGGCGCCAACCCGTGGCAGCACCACCACTACATCTCGCCATCTGCTGCGGCA<br>TCTTTCCCTCAGTCCCAGGACCGCTACATCTGCCAGACCTGCAACAAGGCATTC<br>TCCCGCCCGAGCTCCTTGAGGATACACAGCCACTCGCACACTGGCGAGAAGCCT<br>TTCAAGTGCCCTCACGCCGGCTGCGGCAAGGCTTTCAGCGTGCGCAGCAACATG<br>AAGCGCCACGAGAGGGGCTGCCACAACTATGACAGCAGCAGCAGCAACGGCAC<br>CGCCATGCACTGA |
| >gi\|116193176\|ref\|XM_001222400.1\| *Chaetomium globosum*<br>CBS 148.51 hypothetical protein (CHGG_06306) partial mRNA<br>ATGGCAAACACAATGGTCACACACTACGCGCACGTACCTCAACATAGCCTTCAG<br>TATGGCTACATGCCGCCACCTTCACCGCCAATGGATGAGGCGGCAAAGTGCTCG<br>CTCCCCTCTATCTCGAACCTCCTCGGGCTTGCAGACCAAGGATCGCCGACTTCG<br>GAAACGTCGCCCCAGTCCCAGCAGCAGCAACAGGCGCAGCAGCAGCAGCAACA<br>GCAATGTATGAGCAGCTCGTGGTGGGATATGGGACACCTAGATACTGACTCGA<br>CCCCAGCGCAAGGATCCAAGCCGGAGACGAGGCCCAACTCTTCGCATTACACC<br>AACCCGGTAACCATTCGGACAGGACTCCCGCCCAGCCCGCCCATGTCCTCGGAT<br>GCATCCTTTGAAGGTTTCAACTCGCCATCGACCAGGTCGGTGAGCCAGGTGCCG<br>AACGGGTCAAACTACTTCTTTGAGACAACGCCACCGCTTCAGATGGAAGCCGAT<br>GCACGGCAGATGACCGCTGCCGCCGCCGTCCCGCGAGTTTCTGTCCAGGCTTCA<br>GCCTACCAGCCCCAGTACGCTCCCGGCCCTGCGTACATGAGTCAACCAGCCATG<br>ACCTCATACTATCCTCCGATGCAATCCGCGGCGCCACCGCAGACGCAAATGTCC<br>GGCCTCTACTACCAACGACCGCTTCCTCAGTCTTTTCCGCCTCCGATGTCCATGT<br>CTATGACTCTTGCGCCGACGGCCGGGAACCCCTGGCAGCACCATCACTACATTG<br>CCCCTTCGGCGTCAGCATCCTTTCCCCAGAGCCAGGACCGGTATATCTGCCCGA<br>CGTGCAGCAAAGCCTTCTCGCGGCCCAGCTCGCTGCGGATCCACAGCCACTCGC<br>ACACGGGCGAGAAGCCCTTCAAGTGCCCGTTCCCGGGTTGCGGCAAGGCCTTCA<br>GTGTGCGCAGCAACATGAAGCGGCACGAACGTGGGTGCCACAACTACGACAGC<br>AGCAGCACGACGAGCAGCACCGGCACCATGAACAGCAACACCGGGGGAAGCC<br>GTCCCTGA |
| >(gi\|342883535: 113711-113828, 113878-114590) *Fusarium oxysporum* Fo5176 contig01821, whole genome shotgun sequence<br>ATGGAGGAACAAAAGTGCTCTCTACCCTCAATCTCGAACCTCTTGGGTTTGGCC<br>GATGCCGGCTCACCCACGAGTGAGTCCTCACCAACTTCACGGCAACATTCTCCT<br>CGCTTTGAAGTTCCTCCACCTTCACATGGTCATAGCCGAGCTGGATCTGAATGG<br>GCTAAATCATCGCACCGTGGGCTTCCCCCTACACCACCTATGAGCACAGACGCA<br>TCTTTCGAAGGCTACAGCTCCCCCACAAGGAAACCATCCAACCAGGCGTATCCA<br>GGCTCAGCACCAAGAACATACTATTACGAGACCACACCACCTCTAGAAGCCGA<br>TGCACAGCGTCAGGCATCAGTAACGGCTATTCCTCGAGCAACACCTCCAGCAAC<br>GGCTCCTTATCCTCAGCAAGCTCACCCCACGGTATACGCCAACCCAGCACCAGT<br>GGGCGCTTATTACCCGGCGGCACAGGTGCCTCCTGCTGTCCAGCCTCAAGAGAT<br>GAACCCTTACTACCAGCGCCCTCTCCCACAGGCTTATCCCCCACCAGTGAGCAT<br>GCCAGCACCTGCTCCCTCGGGAGCAAATCCTTGGCAGCACCATCACTATCTTAA<br>CCCAACTGGAGCGGCGGCATTCCCGCAAAGCCAGGACCGGTATATTTGCCCGA<br>CTTGCAACAAAGCCTTTAGCAGGCCCAGCAGTCTCCGAATCCACAGTCACTCAC<br>ATACCGGAGAGAAACCCTTCAAGTGTCCCCATGCTGGATGTGGCAAGGCTTTCA<br>GCGTACGCAGCAACATGAAACGTCATGAGAGGGGCTGTCACAGCTTCGAATTT<br>AATGGGTCTGTGATTCGGGGTTGA |

PUBLICATIONS

These publications are incorporated by reference to the extent they relate materials and methods disclosed herein.

BROWN, D. W., J. H. YU, H. S. KELKAR, M. FERNANDES, T. C. NESBITT et al., 1996 Twenty-five coregulated transcripts define a sterigmatocystin gene cluster in *Aspergillus nidulans*. Proceedings of the National Academy of Sciences of the United States of America 93: 1418-1422.

CALVO, A. M., J. BOK, W. BROOKS and N. P. KELLER, 2004 veA is required for toxin and sclerotial production in *Aspergillus parasiticus*. Applied and Environmental Microbiology 70: 4733-4739.

Calvo A. M. 2008. The VeA regulatory system and its role in morphological and chemical development in fungi. Fungal Genetics and Biology 45:1053-61.

COLE, R. J., and R. H. COX, 1981 *Handbook of Toxic Fungal Metabolites*. Academic Press, New York.

DURAN, R. M., J. W. CARY and A. M. CALVO, 2007 Production of cyclopiazonic acid, aflatrem, and aflatoxin by *Aspergillus flavus* is regulated by veA, a gene necessary for sclerotial formation. Applied Microbiology and Biotechnology 73: 1158-1168.

KAFER, E., 1977 Meiotic and mitotic recombination in *Aspergillus* and its chromosomal aberrations. Adv. Genet 19: 33-131.

KATO, N., W. BROOKS and A. M. CALVO, 2003 The expression of sterigmatocystin and penicillin genes in *Aspergillus nidulans* is controlled by veA, a gene required for sexual development. Eukaryotic Cell 2: 1178-1186.

KELLER, N. P., and T. M. HOHN, 1997 Metabolic pathway gene clusters in filamentous fungi. Fungal Genetics and Biology 21: 17-29.

KIM, H. S., K. Y. HAN, K. J. KIM, D. M. HAN, K. Y. JAHNG et al., 2002 The veA gene activates sexual development in *Aspergillus nidulans*. Fungal Genetics and Biology 37: 72-80.

MILLER, B. L., K. Y. MILLER, K. A. ROBERTI and W. E. TIMBERLAKE, 1987 Position-dependent and position-independent mechanisms regulate cell-specific expression of the spoc1 gene-cluster of *Aspergillus nidulans*. Molecular and Cellular Biology 7: 427-434.

MILLER, B. L., K. Y. MILLER and W. E. TIMBERLAKE, 1985 Direct and indirect gene replacements in *Aspergillus nidulans*. Molecular and Cellular Biology 5: 1714-1721.

MYUNG, K., S. J. LI, R. A. E. BUTCHKO, M. BUSMAN, R. H. PROCTOR et al., 2009 FvVE1 Regulates Biosynthesis of the Mycotoxins Fumonisins and Fusarins in *Fusarium verticillioides*. Journal of Agricultural and Food Chemistry 57: 5089-5094.

OSHEROV, N., and G. MAY, 2000 Conidial germination in *Aspergillus nidulans* requires RAS signaling and protein synthesis. Genetics 155: 647-656.

PONTECORVO, G., J. A. ROPER, L. M. HEMMONS, K. D. MACKDONALD, A. W. BUFTON et al., 1953. The genetics of *Aspergillus nidulans*. Adv. Genet. 5: 141-238.

SAMBROOK, J., and D. W. RUSSELL, 2003 *Molecular cloning: a laboratory manual, 3rd ed.* Cold Spring Harbor Laboratory Press, Cold Spring Harbor, N.Y.

YELTON, M. M., J. E. HAMER, E. R. DESOUZA, E. J. MULLANEY and W. E. TIMBERLAKE, 1983 Developmental regulation of the *Aspergillus nidulans*-Trpc Gene. Proceedings of the National Academy of Sciences 80: 7576-7580.

Yu, J. H., R. A. Butchko, M. Fernandes, N. P. Keller, T. J. Leonard, and T. H. Adams. 1996. Conservation of structure and function of the aflatoxin regulatory gene aflR from *Aspergillus nidulans* and *A. flavus*. Curr. Genet. 29: 549-555.

The invention claimed is:

1. A gene replacement construct designated ΔmtfA.

2. An ΔmtfA mutant that overexpresses mftA.

3. A method to regulate secondary metabolite synthesis by fungal genes, the method comprising:

(a) obtaining a fungus with a transcription factor, designated mtfA; and (b) altering expression of the gene encoding mtfA.

4. A method to increase production of a secondary metabolite from a fungus, the method comprising:

(a) obtaining a fungus with a gene encoding the transcription factor mtfA; and (b) increasing the production of the secondary metabolite by causing the fungus to overexpress the mtfA gene.

5. The method of claim 4 wherein the fungal secondary metabolite is penicillin or other secondary metabolites.

6. A method to retard sexual and asexual development of a fungus, the method comprising:

(a) obtaining the fungus; and (b) altering the function of the mtfA gene.

7. The method of claim 3, wherein altering the gene encoding the mtfA factor is by overexpressing or deleting the gene or parts of the gene, or inserting a segment into the coding region of the gene.

8. The method of claim 3, wherein the secondary metabolites are selected from the group consisting of mycotoxin, terraquinone, and sterigmatocystin.

9. The method of claim 7 wherein overexpressing the gene encoding mftA increases penicillin G production by the fungus, and decreases aflatoxin related mycotoxin production.

10. The method of claim 7 wherein deletion in the gene encoding mtfA decreases sterigmatocystin products.

* * * * *

UNITED STATES PATENT AND TRADEMARK OFFICE

CERTIFICATE OF CORRECTION

PATENT NO. : 8,927,255 B2
APPLICATION NO. : 14/070094
DATED : January 6, 2015
INVENTOR(S) : Ana M. Calvo-Byrd It is certified that error appears in the above-identified patent and that said Letters Patent is hereby corrected as shown below:

In the specification

Column 1, line 20, insert

--This invention was made with government support under Contract No. NIH R15A1081232 awarded by the National Institutes of Health. The U.S. Government has certain rights in the invention--

Signed and Sealed this
Fifteenth Day of December, 2015

Michelle K. Lee
*Director of the United States Patent and Trademark Office*

SEQUENCE LISTING

```
<160> NUMBER OF SEQ ID NOS: 49

<210> SEQ ID NO 1
<211> LENGTH: 936
<212> TYPE: DNA
<213> ORGANISM: Aspergillus nidulans

<400> SEQUENCE: 1

atggatctcg ccaacctcat ctcccaaccg gggcctgagc ctgctctgac ggccaaatca      60

agatacagcc ctcctgcctt tgaaccgggc tccttctacg ccgcatctac ttcattcacg     120

cggacacaag cgccactatc gcctccagtc gaggatagat cttctcgctg ctcactgcca     180

tcaatctctg cgcttcttga cagcgcagac ggcgcctcga cacaagctcc aaagcgccaa     240

cggctcagct ctccaatgca ccgtgaaccg cttgacaaga acccatctgc cggcgctgct     300

cccatccgtc tcccgcccac tcctccattg cgccccggct ccggcttcca cagcgccggc     360

cactcgccct cgagctccat ctcatccatc tcgatgatca agtccgagta cccggcacca     420

ccatcagctc cagtctctct tccgggcctt cccagcccaa ccgaccgctc gtccatctcg     480

agccaagggt ctgcgccgca gcaccagcat ggtccctacg cctcgccagc tcccagcgtg     540

gcgccctctt actcctcgcc cgttgagccc tcaccctcat cggcaatgta ctaccaacac     600

cagcggcccg catcctcagg cacataccag gctcctccac ccccgccgca acaccagccc     660

atgatctcgc ccgtgacacc ggcctggcag caccaccact acttccctcc ttcctcaaac     720

acaccctacc agcagaacca cgaccgatat atctgccgca cctgccacaa ggcgttctcg     780
```

```
cggccctcga gtctgcgcat ccacagccat agccacaccg gcgagaagcc atttcggtgc     840

acacatgccg gatgcggcaa agcctttagt gtacggagca acatgaagcg ccatgagcgc     900

ggctgccata ccgggagggc tgtcgcgatg gtgtaa                               936


<210> SEQ ID NO 2
<211> LENGTH: 258
<212> TYPE: PRT
<213> ORGANISM: Aspergillus nidulans

<400> SEQUENCE: 2

Met Asp Leu Ala Asn Gln Pro Gly Pro Glu Pro Ala Leu Thr Ala Lys
1               5                   10                  15

Ser Arg Tyr Ser Pro Pro Ala Phe Glu Pro Gly Ser Phe Tyr Ala Ala
            20                  25                  30

Ser Thr Ser Phe Thr Arg Thr Gln Ala Arg Ser Ser Ala Leu Leu Asp
        35                  40                  45

Ser Thr Gln Ala Pro Lys Arg Gln Arg Leu Ser Ser Pro Met His Arg
    50                  55                  60

Glu Pro Leu Asp Lys Asn Pro Ser Ala Gly Ala Ala Pro Ile Arg Gly
65                  70                  75                  80

Ser Gly Phe His Ser Ala Gly His Ser Pro Ser Ser Ser Ile Ser Ser
                85                  90                  95

Ile Ser Met Ile Lys Ser Glu Tyr Pro Ala Pro Pro Ser Ala Pro Val
            100                 105                 110

Ser Leu Pro Gly Ser Pro Thr Asp Arg Ser Ser Ile Ser Ser Gln Gly
        115                 120                 125

Ser Ala Pro Gln His Gln His Gly Pro Tyr Ala Ser Pro Ala Ala Pro
    130                 135                 140

Ser Ser Pro Ser Ser Ala Met Tyr Tyr Gln His Gln Arg Pro Ala Ser
145                 150                 155                 160

Ser Gly Thr Tyr Gln Ala Pro Pro Pro Pro Pro Gln His Gln Pro Met
                165                 170                 175

Ile Ser Thr Pro Ala Trp Gln His His His Tyr Phe Pro Pro Ser Ser
            180                 185                 190

Asn Thr Pro Tyr Gln Gln Asn His Asp Arg Tyr Ile Cys Arg Thr Cys
        195                 200                 205

His Lys Ala Phe Ser Arg Pro Ser Ser Leu Arg Ile His Ser His Ser
    210                 215                 220

His Thr Gly Glu Lys Pro Phe Arg Cys Thr His Ala Gly Cys Gly Lys
225                 230                 235                 240

Ala Phe Ser Val Arg Ser Asn Met Lys Arg His Glu Arg Ala Val Ala
                245                 250                 255

Met Val


<210> SEQ ID NO 3
<211> LENGTH: 247
<212> TYPE: PRT
<213> ORGANISM: Aspergillus oryzae

<400> SEQUENCE: 3

Met Asp Leu Ala Ser Pro Gly Pro Glu Pro Ile Tyr Lys Ser Arg Ala
1               5                   10                  15

Ser Tyr Ser Pro Pro Pro Ser Ser Ala Gly Ser Tyr Lys Arg Pro Ala
            20                  25                  30

Glu His Asp Ser Tyr Phe Ser Arg Ala Pro Gln Ala Gln Pro Glu Gly
```

```
        35                  40                  45

Ala Asp Ser Thr Tyr Ala Ala Lys Arg Gln Arg Thr Ser Pro Pro Pro
    50                  55                  60

Arg Arg Glu Ser Glu Phe Arg Ser Pro Tyr Asp Ser Val Ser Thr Pro
65                  70                  75                  80

Asn Gly His Ser Gly His His Ser Pro Ser Ala Ser Ser Val Thr Ser
                85                  90                  95

Gly Lys Ala Ile Lys Leu Glu Ser Tyr Ser Gln Thr Pro Met Thr Ser
            100                 105                 110

Pro Ser Asp Arg Ser Ser Ile Ser Ser Gln Gly Ser Val His His Val
        115                 120                 125

Ser Ala Ala Pro Tyr Ala Ser Pro Ala Ala Ser Ser Ser Ala Pro Ser
    130                 135                 140

Ala Met Tyr Tyr Gln Arg Pro Ser Gly Ser Tyr Gln Thr Pro Ala Thr
145                 150                 155                 160

Val Pro Ser Pro Ser Ala Ala Pro Met Pro Ala Ser Ala Thr His Gln
                165                 170                 175

Gln Met Ile Thr Thr Pro Tyr Gln Gln Asn His Asp Arg Tyr Ile Cys
            180                 185                 190

Arg Thr Cys His Lys Ala Phe Ser Arg Pro Ser Ser Leu Arg Ile His
        195                 200                 205

Ser His Ser His Thr Gly Glu Lys Pro Phe Arg Cys Thr His Ala Gly
    210                 215                 220

Cys Gly Lys Ala Phe Ser Val Arg Ser Asn Met Lys Arg His Glu Arg
225                 230                 235                 240

Pro Val Ala Thr Ala Met Val
                245


<210> SEQ ID NO 4
<211> LENGTH: 272
<212> TYPE: PRT
<213> ORGANISM: Aspergillus niger

<400> SEQUENCE: 4

Met Asp Leu Ala Ser His Pro Gly Pro Asp Pro Ile Met Lys Ser Arg
1               5                   10                  15

Ala Ser Tyr Ser Pro Pro Met Thr Ser Tyr Lys Arg Ser Ile Glu His
            20                  25                  30

Thr Ser Asp Ser Tyr Phe Pro Ser Val Pro Ile Thr Arg Ser Pro Gln
        35                  40                  45

Pro Gln Ser Pro Glu Gly Ala Met His Ala Ala Lys Arg Thr Arg Met
    50                  55                  60

Thr Pro Pro Leu Gln Arg Asp Leu Asp Ser Arg Gln Gln Ser Gln Ala
65                  70                  75                  80

Tyr Asp Leu Lys Ala Asn Gly Pro Gln Ile Gly Ser Ser Phe His Ser
                85                  90                  95

Ala Gly His Ser Pro Ala Ser Ser Ile Ser Ala Ala Ser Asp Ala Ala
            100                 105                 110

Ala Pro Lys Arg Ser Asp Ser Tyr Pro Gln Val Pro Met Ala Ser Pro
        115                 120                 125

Ser Asp Arg Ser Ser Ile Ser Ser Gln Gly Ser Val Gln Gly Val Ser
    130                 135                 140

Ser Ala Ser Tyr Ala Ser Pro Ala Ser Ser Ala Ser Ser Ala Met Phe
145                 150                 155                 160
```

```
Tyr Gln Arg Thr Ala Pro Ser Thr Ser Ala Ala Pro Leu Pro Thr Pro
                165                 170                 175

Ala Ala Pro Gln Gln Ile Ile Ser Asn Pro Ala Trp Gln His His His
            180                 185                 190

Tyr Phe Pro Pro Ser Ser Thr Thr Pro Tyr Gln Gln Asn His Asp Arg
        195                 200                 205

Tyr Ile Cys Arg Thr Cys His Lys Ala Phe Ser Arg Pro Ser Ser Leu
    210                 215                 220

Arg Ile His Ser His Ser His Thr Gly Glu Lys Pro Phe Arg Cys Thr
225                 230                 235                 240

His Ala Gly Cys Gly Lys Ala Phe Ser Val Arg Ser Asn Met Lys Arg
                245                 250                 255

His Glu Arg Gly Cys His Ser Gly Arg Pro Val Ala Thr Ala Met Val
            260                 265                 270


<210> SEQ ID NO 5
<211> LENGTH: 272
<212> TYPE: PRT
<213> ORGANISM: Aspergillus kawachii

<400> SEQUENCE: 5

Met Asp Leu Ala Ser His Pro Gly Pro Asp Pro Ile Met Lys Ser Arg
1               5                   10                  15

Ala Ser Tyr Ser Pro Pro Met Thr Ser Tyr Lys Arg Ser Ile Glu Gln
            20                  25                  30

Thr Ser Asp Ser Tyr Phe Pro Ser Val Pro Ile Thr Arg Ser Pro Gln
        35                  40                  45

Pro His Ser Pro Glu Gly Ala Met His Ala Ala Lys Arg Thr Arg Met
    50                  55                  60

Thr Pro Pro Leu Gln Arg Asp Leu Asp Ser Arg Gln Gln Ser Gln Ala
65                  70                  75                  80

Tyr Asp Leu Lys Ala Asn Gly Pro Gln Ile Gly Ser Ser Phe His Ser
                85                  90                  95

Ala Gly His Ser Pro Ala Ser Ser Ile Ser Ala Ala Ser Asp Ala Ala
            100                 105                 110

Ala Pro Lys Arg Ser Asp Ser Tyr Pro Gln Val Pro Met Ala Ser Pro
        115                 120                 125

Ser Asp Arg Ser Ser Ile Ser Ser Gln Gly Ser Val Gln Gly Val Ser
    130                 135                 140

Ser Ala Ser Tyr Ala Ser Pro Ala Ser Ser Ala Ser Ser Ala Met Phe
145                 150                 155                 160

Tyr Gln Arg Thr Ala Pro Ser Thr Ser Ala Ala Pro Leu Pro Thr Pro
                165                 170                 175

Ala Ala Pro Gln Gln Ile Ile Ser Asn Pro Ala Trp Gln His His His
            180                 185                 190

Tyr Phe Pro Pro Ser Ser Thr Thr Pro Tyr Gln Gln Asn His Asp Arg
        195                 200                 205

Tyr Ile Cys Arg Thr Cys His Lys Ala Phe Ser Arg Pro Ser Ser Leu
    210                 215                 220

Arg Ile His Ser His Ser His Thr Gly Glu Lys Pro Phe Arg Cys Thr
225                 230                 235                 240

His Ala Gly Cys Gly Lys Ala Phe Ser Val Arg Ser Asn Met Lys Arg
                245                 250                 255

His Glu Arg Gly Cys His Ser Gly Arg Pro Val Ala Thr Ala Met Val
            260                 265                 270
```

<210> SEQ ID NO 6
<211> LENGTH: 280
<212> TYPE: PRT
<213> ORGANISM: Neosartorya fischeri

<400> SEQUENCE: 6

```
Met Asp Val Ala Ser Pro Ser Glu Ser Asp Thr Val Pro Thr Phe Arg
1               5                   10                  15

Ser Arg Ser Ile Gln Asn Ser Ser Ala Ser His Tyr Lys Arg Leu Ser
            20                  25                  30

Glu Gln Tyr Thr Gly Ser Tyr Phe Ser Ala Ala Pro Thr His Thr Thr
        35                  40                  45

Ser Arg Thr Pro Gln Pro Pro Leu Ser Pro Pro Ala Glu Asp Gln Pro
    50                  55                  60

Lys Cys Ser Leu Pro Ser Ile Ser Ile Leu Leu Glu Asn Ala Ala His
65                  70                  75                  80

Ala Ala Lys Arg Gln Arg Thr Ser Leu Ser Thr His Arg Asp Ser Gly
                85                  90                  95

Pro Pro Tyr Asp Ser Ile Thr Pro His Gly Ser Gly Phe His Ser Asn
            100                 105                 110

Gly His Ser Pro Ser Ala Ser Ser Val Ser Ala Thr Ser Ser Ser Ala
        115                 120                 125

Val Met Lys Asn Thr Glu Thr Tyr Ser Gln Ala Pro Ile Gly Ser Pro
    130                 135                 140

Thr Asp Arg Ser Ser Ile Ser Ser Gln Gly Ser Val Gln His Ala Ala
145                 150                 155                 160

Gly Ala Pro Tyr Ala Ser Pro Ala Ser Phe Ser Ser Thr Pro Ser Thr
                165                 170                 175

Ala Ala Tyr Tyr Gln Arg Asn Pro Ala Pro Asn Gln Asn Pro Gly Ser
            180                 185                 190

Phe Pro Pro Thr Ser Ala Ala Ser Leu Pro Ser Pro Gly His Gln Gln
        195                 200                 205

Met Ile Ser Thr Thr Pro Tyr Gln Gln Asn His Asp Arg Tyr Ile Cys
    210                 215                 220

Arg Thr Cys His Lys Ala Phe Ser Arg Pro Ser Ser Leu Arg Ile His
225                 230                 235                 240

Ser His Ser His Thr Gly Glu Lys Pro Phe Arg Cys Thr His Ala Gly
                245                 250                 255

Cys Gly Lys Ala Phe Ser Val Arg Ser Asn Met Lys Arg His Glu Arg
            260                 265                 270

Pro Val Ala Thr Ala Met Val Gln
        275                 280
```

<210> SEQ ID NO 7
<211> LENGTH: 244
<212> TYPE: PRT
<213> ORGANISM: Penicillium chrysogenum

<400> SEQUENCE: 7

```
Met Asp Leu Ser Asn His Ser Ala Ala Val Lys Pro Ile Tyr Thr Pro
1               5                   10                  15

Val Glu Ser Tyr Lys Arg Ser Pro Pro Leu Ser Pro Pro Ala Pro Lys
            20                  25                  30

Val Phe Glu Gly Gln His Ala Ala Thr Ser Leu Thr Leu Asn Leu Pro
        35                  40                  45
```

```
Glu Arg Gln Arg Leu Ser Pro Ser Leu Gly Asp Arg His Val Arg Val
    50                  55                  60

Gln Ser Tyr Glu Gly Ser Gly His Ala His Arg Arg Ala Ser Pro Val
65                  70                  75                  80

Glu Ser Leu Ser His Lys Glu Ala His Gln His His Leu His Arg Ser
                85                  90                  95

Ser Ile Ser Ser Asn Ser Ser Val His Ile Pro Arg Asn Thr Val Pro
            100                 105                 110

Tyr Ala Ser Pro Val Thr Ala Pro Gln Gln Pro Met Tyr Tyr Pro Arg
        115                 120                 125

Pro Pro Thr Thr Ser Gln Pro Ser Thr Pro Ala Ser Ala Pro Gln Met
    130                 135                 140

Pro Pro Val Gln Val Gln Thr Gln Gln Pro His Ser His Ser His Ser
145                 150                 155                 160

Ser Ser Ala Leu Ile Ser Thr Pro Tyr Gln Gln Asn His Asp Arg Tyr
                165                 170                 175

Ile Cys Arg Thr Cys His Lys Ala Phe Ser Arg Pro Ser Ser Leu Arg
            180                 185                 190

Ile His Ser His Ser His Thr Gly Glu Lys Pro Phe Arg Cys Thr His
        195                 200                 205

Ala Gly Cys Gly Lys Ala Phe Ser Val Arg Ser Asn Met Lys Arg His
    210                 215                 220

Glu Arg Gly Cys His Ser Gly Arg Pro Ala Pro Ala Pro Ala Ala Thr
225                 230                 235                 240

Ala Leu Val Val


<210> SEQ ID NO 8
<211> LENGTH: 297
<212> TYPE: PRT
<213> ORGANISM: Coccidioides immitis

<400> SEQUENCE: 8

Met Asn Val Ser Ser Cys Asp Gln Pro His Gln Leu Arg Ala Pro Ala
1               5                   10                  15

Ser Ser Tyr Ser Glu His Arg Arg Ser Pro Ser Ile Pro Lys Pro Leu
            20                  25                  30

Gln Thr Glu Ser Ser Ser Cys Ala Ser Pro Tyr Ser Arg Phe Glu Arg
        35                  40                  45

Leu Pro Leu Ser Pro Pro Glu Glu Asp Gly Lys Thr Gln Phe Arg Gly
    50                  55                  60

Val Val Ser Asp Ala His Val Ala Lys Arg Gln Arg Thr Asn Pro Pro
65                  70                  75                  80

Pro Ser Ile Asp Leu Gly Met Glu Arg Arg Thr Ile Asp Gln Thr Leu
                85                  90                  95

Lys Gln Arg Pro Leu Met Asn Ser Thr Ser Gln Ser Pro Ser Thr Ser
            100                 105                 110

Ser Pro Pro Arg Ser Ala Ile Ser Leu Pro Ser Leu Val Arg Ser Tyr
        115                 120                 125

Pro Ser Pro Val Ser Glu Val Pro Glu Gly Arg Arg Met Ser Gln Ile
    130                 135                 140

Ser Arg His Ser Arg Gly Ala Ser Thr Ser Gln Thr Ser Gln Leu Ser
145                 150                 155                 160

Gly Pro Glu Thr Arg Tyr Pro Ser Pro Pro Asn Val Asn Ser Pro Thr
                165                 170                 175
```

```
Phe Ala Ala Ala Pro Lys Pro Thr Glu Tyr Tyr Pro Ala Ser Arg Pro
            180                 185                 190

Val Pro Pro Val Ala Phe Ala Val Leu Pro Ser Gln Pro Thr His Pro
        195                 200                 205

Gln Val Leu Gly Ser Pro Ala Trp Gln His His His Tyr Phe Pro Pro
    210                 215                 220

Ser Asn Leu Asn His Asp Arg Tyr Ile Cys Arg Ile Cys His Lys Ala
225                 230                 235                 240

Phe Ser Arg Pro Ser Ser Leu Arg Ile His Ser His Ser His Thr Gly
                245                 250                 255

Glu Lys Pro Phe Arg Cys Pro His Ala Gly Cys Gly Lys Ala Phe Ser
            260                 265                 270

Val Arg Ser Asn Met Lys Arg His Glu Arg Gly Cys His Pro Gly Arg
        275                 280                 285

Ser Ala Pro Pro Ser Ala Leu Val Asn
    290                 295


<210> SEQ ID NO 9
<211> LENGTH: 268
<212> TYPE: PRT
<213> ORGANISM: Ajellomyces capsulatus

<400> SEQUENCE: 9

Met Asn Leu Ser His Ser Tyr His Ser Pro Pro Ser Thr Tyr Pro His
1               5                   10                  15

Ser Gly Thr Ser Gln Lys Arg Gln Ser Leu Gln Ser Glu Ser Ser Leu
            20                  25                  30

Ser Val Ser Asn Gly Tyr Tyr Asp Arg Asn Ala Ser Asn Leu Ala Tyr
        35                  40                  45

Ala Arg Ser Pro Gln Pro Gln Ser Arg Phe Gln Gly Ala Asp Gln Leu
    50                  55                  60

Ser Pro Val His Ile Ala His Arg Pro Asn Pro Leu Ser Thr Gly Glu
65                  70                  75                  80

Val Asp Leu Lys Ser Gln Gly His Gly Ala Thr Gln Lys Pro Ile His
                85                  90                  95

Arg Pro Arg Met Ile Gly Ser Gly Leu Asp Gly Arg Asn His Ser Pro
            100                 105                 110

Ala Gly Ser Ser Pro Ser Ser Ala His Ser Pro Ile Ser Val Ala Asn
        115                 120                 125

Leu Thr Ser Ser Ser Ser Ala Asp Pro Ser Tyr Gln His Arg Met Pro
    130                 135                 140

Gln Gly Pro Pro Gln Ser Thr Asn Ser Pro Val Ser Leu Pro Glu Lys
145                 150                 155                 160

His Tyr Ala Pro Ser Ser Asn Leu Ser Ser Thr Pro Phe Ala Leu Ala
                165                 170                 175

Asn Ser Thr Glu Tyr Tyr His Arg Pro Ser His Pro Pro Ser Thr Ser
            180                 185                 190

Ile Pro Leu Ala Ala Pro Pro Ala Gln Gln His His His His Ser Met
        195                 200                 205

Ile Ser Thr Trp Gln His His His Tyr Phe Pro Pro Ser Asn Thr Ala
    210                 215                 220

Pro Tyr Pro Gln Asn His Asp Arg Tyr Ile Cys Arg Ile Cys His Lys
225                 230                 235                 240

Ala Phe Val Asn Cys Gly Lys Ser Phe Ser Val Arg Ser Asn Met Lys
```

```
                245                 250                 255

Arg His Glu Arg Pro Thr Gln Ala Ala Leu Val Asn
            260                 265


<210> SEQ ID NO 10
<211> LENGTH: 360
<212> TYPE: PRT
<213> ORGANISM: Uncinocarpus reesii

<400> SEQUENCE: 10

Met Asn Val Ser Ser Cys Asp Gln Thr Ala Pro Phe His Gly Ser Ala
1               5                   10                  15

Thr Ser Tyr Phe Glu His His Gln Arg Ile Arg Ser Pro Ser Ile Pro
            20                  25                  30

Lys Arg Ser His Glu Glu Asn Ser Ser Ser Ala Ser Pro Tyr Pro Pro
        35                  40                  45

Phe Ala Thr Leu Pro Leu Ser Pro Pro Glu Gly Lys Thr Thr Phe Gln
    50                  55                  60

Ser Val Asp Thr His Val Ala Lys Arg Gln Arg Ala Asn Pro Pro Pro
65                  70                  75                  80

Ser Ile Asp Leu Ala Leu Glu Arg Arg Gly Ala Cys Ala Asp Gln Ala
                85                  90                  95

Ile Arg Gln Arg Pro Leu Met Gly Gly Val Asn His Ser Pro Ser Ala
            100                 105                 110

Ser Ser Pro Pro Arg Thr Ala Ile Ser Leu Pro Ser Leu Ile Gly Ser
        115                 120                 125

Tyr Pro Ser Pro Val Ser Glu Ala Pro Glu Gly Arg Arg Met Ser Gln
    130                 135                 140

Ile Ser Arg His Ser Ser Ser Ser Gln His Pro Gly Pro Glu Ala Arg
145                 150                 155                 160

Tyr Pro Ser Pro Pro Thr Leu Ser Ser Pro Ser Phe Ala Ala Pro Pro
                165                 170                 175

Lys Pro Glu Tyr Tyr Ser Ser Gly Ala Arg Pro Thr Asn Phe Pro Pro
            180                 185                 190

Val Thr Phe Ala Val Leu Pro Ser Gln Pro Thr His Pro Gln Met Val
        195                 200                 205

Ala Leu Gly Ser Pro Ala Trp Gln His His His Tyr Phe Pro Pro Ser
    210                 215                 220

Asn Leu Asn His Asp Arg Tyr Ile Cys Arg Ile Cys His Lys Ala Phe
225                 230                 235                 240

Ser Arg Pro Ser Ser Leu Arg Ile His Ser His Ser His Thr Gly Glu
                245                 250                 255

Lys Pro Phe Arg Cys Pro His Ala Gly Cys Gly Lys Ala Phe Ser Val
            260                 265                 270

Arg Asn Gln Pro Arg Ser Gln Arg Ser Leu Ile Glu Lys Arg Lys Gly
        275                 280                 285

Tyr Ala Ile Gly Phe Asp Glu Trp Val Leu Thr Met Ile Thr Pro Thr
    290                 295                 300

Ile Arg Ser Thr Asn Glu Gln Ile Tyr Thr Thr Ala Ser Cys Lys Ile
305                 310                 315                 320

Ala Asn Val Ala Val Ile Asn Ile Asn Arg Arg Ile Ala Glu Leu Arg
                325                 330                 335

Lys Ser Phe Arg Asn Arg Arg Ser Asn Gly Thr Leu Ser Pro Thr Lys
            340                 345                 350
```

```
Arg Arg Val Lys Leu Ala Phe Ser
        355                 360


<210> SEQ ID NO 11
<211> LENGTH: 205
<212> TYPE: PRT
<213> ORGANISM: Penicillium marneffei

<400> SEQUENCE: 11

Met Asp Asn Val Pro Ala Ser Lys Arg Ala Arg His Asp Ser Gly Asp
1               5                   10                  15

Tyr Ser Arg Gly Phe Cys Ser Gly Phe Thr Glu Gly Ser Ser Pro Ala
            20                  25                  30

Ser Leu Pro Ser Gly Arg Ser His Ser Ala Ser Ile Ser Ser Ala Val
        35                  40                  45

Ser His Pro Ser His Gln Gln Arg Thr Ser Leu Pro Ser Ile Ser Ala
    50                  55                  60

Ser Leu Gln Asn Thr Pro Ile His Pro Ser Glu Arg Leu Ser Ile Ser
65                  70                  75                  80

Ser Leu Ala Ser His Asp Ser Ser Arg Leu Ser His Ala Ile Pro Ser
                85                  90                  95

Pro Ser Ser Thr Thr Ala Ser Ile Thr Thr Thr Ala Thr Pro Ser Thr
            100                 105                 110

Ser Tyr Tyr Ser Thr Ser Glu Glu Lys Ala Tyr Pro Arg Ser His Ser
        115                 120                 125

Thr Ser Ala Pro Val Thr Pro Ser Thr Leu Val Pro Pro Pro Pro Ala
    130                 135                 140

Met Leu Ser Asn His Leu Thr Ser Arg Pro Ser Ser Leu Arg Ile His
145                 150                 155                 160

Ser His Ser His Thr Gly Glu Lys Pro Phe Arg Cys Thr His Ala Gly
                165                 170                 175

Cys Gly Lys Ala Phe Ser Val Arg Ser Asn Met Lys Arg His Glu Arg
            180                 185                 190

Gly Cys His Ser Gly Arg Pro Met Thr Ala Thr Val Val
        195                 200                 205


<210> SEQ ID NO 12
<211> LENGTH: 251
<212> TYPE: PRT
<213> ORGANISM: Botryotinia fuckeliana

<400> SEQUENCE: 12

Met Ala Ser Ser Leu Val Ser Asn Pro Tyr Thr Val His Pro Met Ala
1               5                   10                  15

Gln His Ser Ser Tyr Val Asn Ala Pro Gln Pro Pro Pro Thr Ser Gly
            20                  25                  30

Leu Ser Ser Pro Thr Glu Gln Ala Gln Gln Gln Ser Ser Pro Gln Gln
        35                  40                  45

Ala Ala Phe Lys Glu Asp Tyr Glu Ser Gly His Gln Tyr Gly Pro Ser
    50                  55                  60

Ser Ser Met Ser Ser Arg Gly Gln Ser Asp Gly Gly Phe Asp Gly Arg
65                  70                  75                  80

Gln Ser Pro Ser Gln Ala Ser Thr Ser Ser Tyr Ser Val Val Ser Ala
                85                  90                  95

Pro Asn Tyr Tyr Phe Asn Pro Ser Gln Val Ser Ala Ile Asn Asn Met
            100                 105                 110
```

-continued

Glu Pro His Ala Gln Arg Gln Pro Val Gln Thr Val Thr Arg Arg Val
        115                 120                 125

Ser Met Pro Val Ser Ser Met Gln Tyr Gly His Ser Pro Phe Asn Gly
    130                 135                 140

Ser Tyr Thr Met Ser Pro Gly Ala Gln Ser Tyr Tyr Pro Gln Thr Gln
145                 150                 155                 160

Ser Pro Gln Val Ser Ser Leu Tyr Tyr Gln Arg Pro Leu Pro Gln Gln
                165                 170                 175

Phe Pro Pro Pro Met Met Pro Val Ser Val Thr Leu Thr Pro Ser Ser
            180                 185                 190

Gly Ala Asn Pro Trp Gln His His His Tyr Ile Ser Pro Ser Ser Ala
        195                 200                 205

Ser Gln Asp Arg Tyr Ile Cys Gln Thr Cys Asn Lys Ala Phe Gln Asn
    210                 215                 220

Cys Gly Lys Ala Phe Ser Val Arg Ser Asn Met Lys Arg His Glu Arg
225                 230                 235                 240

Gly Cys His Ser Phe Glu Ser Ala Ser Met Val
                245                 250

<210> SEQ ID NO 13
<211> LENGTH: 236
<212> TYPE: PRT
<213> ORGANISM: Neurospora tetrasperma

<400> SEQUENCE: 13

Met Ala Pro Thr Thr Leu Thr Pro Gln Tyr Pro Ala Gln Pro Tyr Gly
1               5                   10                  15

Phe Ala Pro Pro Pro Ser Asn Lys Cys Ser Leu Pro Ser Ile Ser Asn
            20                  25                  30

Leu Leu Val Met Ala Asp Gln Pro Thr Ser Glu Thr Ser Pro Gln Ser
        35                  40                  45

Gln Gln Leu His Phe Ser Lys Pro Asp Asn Asn Ser Ser Gln Phe Gly
    50                  55                  60

Asn Pro Ala Ser Ile Arg Ala Asn Ser Ser Glu Ala Ser Phe Glu Gly
65                  70                  75                  80

Tyr Arg Ser Pro Ser Ser Lys Pro Ala Ser Gln Ser Gln Gly Ser Ser
                85                  90                  95

Asn Tyr Tyr Tyr Glu Thr Thr Pro Pro Leu Ser Gln His Glu Ala Asp
            100                 105                 110

Ser Arg Gln Met Ala Thr Ala Ala Pro Arg Ala Pro Val Gln Ser Ser
        115                 120                 125

Thr Phe Gln Thr Gln Tyr Pro Ser Ser Ala Gly Tyr Ser Ser Gln Ser
    130                 135                 140

Gly Met Asn Pro Tyr Tyr Pro Pro Met Gln Pro Thr Pro Pro Pro Gln
145                 150                 155                 160

Gln Gln Met Ser Gly Leu Tyr Tyr Gln Arg Pro Leu Pro Gln Thr Pro
                165                 170                 175

Ala Val Pro Val Pro Val Thr Leu Ala Pro Val Thr Gly Ala Asn Pro
            180                 185                 190

Trp Gln His His His Tyr Ile Ala Ser Gln Asp Arg Tyr Ile Cys Gln
        195                 200                 205

Thr Cys Asn Lys Ala Phe Gly Cys His Ser Phe Glu Ser Ser Asn Gly
    210                 215                 220

Arg Ser Ser Gly Asn Ser Asn Asn Gly Ala Ser Ala
225                 230                 235

<210> SEQ ID NO 14
<211> LENGTH: 236
<212> TYPE: PRT
<213> ORGANISM: Neurospora crassa

<400> SEQUENCE: 14

```
Met Ala Pro Thr Thr Leu Thr Pro Gln Tyr Pro Ala Gln Pro Tyr Gly
1               5                   10                  15

Phe Ala Pro Pro Pro Ser Asn Lys Cys Ser Leu Pro Ser Ile Ser Asn
            20                  25                  30

Leu Leu Val Met Ala Asp Gln Pro Thr Ser Glu Thr Ser Pro Gln Ser
        35                  40                  45

Gln Gln Leu His Phe Ser Lys Pro Asp Asn Asn Ser Ser Gln Phe Gly
    50                  55                  60

Asn Pro Ala Ser Ile Arg Ala Asn Ser Ser Glu Ala Ser Phe Glu Gly
65                  70                  75                  80

Tyr Arg Ser Pro Ser Ser Lys Pro Ala Ser Gln Ser Gln Gly Ser Ser
                85                  90                  95

Asn Tyr Tyr Tyr Glu Thr Thr Pro Pro Leu Ser Gln His Glu Ala Asp
            100                 105                 110

Ser Arg Gln Met Ala Thr Ala Thr Pro Arg Ala Pro Val Gln Ser Ser
        115                 120                 125

Thr Phe Gln Thr Gln Tyr Pro Ser Ser Ala Gly Tyr Ser Ser Gln Ser
    130                 135                 140

Gly Met Asn Pro Tyr Tyr Pro Pro Met Gln Pro Thr Pro Pro Pro Gln
145                 150                 155                 160

Gln Gln Met Ser Gly Leu Tyr Tyr Gln Arg Pro Leu Pro Gln Thr Pro
                165                 170                 175

Ala Val Pro Val Pro Val Thr Leu Ala Pro Val Thr Gly Ala Asn Pro
            180                 185                 190

Trp Gln His His His Tyr Ile Ala Ser Gln Asp Arg Tyr Ile Cys Gln
        195                 200                 205

Thr Cys Asn Lys Ala Phe Gly Cys His Ser Phe Glu Ser Ser Asn Gly
    210                 215                 220

Arg Ser Ser Gly Asn Ser Asn Asn Ser Ala Ser Ala
225                 230                 235
```

<210> SEQ ID NO 15
<211> LENGTH: 267
<212> TYPE: PRT
<213> ORGANISM: Magnaporthe oryzae

<400> SEQUENCE: 15

```
Met Ala Ala Thr Met Ile Gln Gln Pro Tyr Pro Ile His Gln Gln Gln
1               5                   10                  15

Ser Gln Tyr Met Val Gln Pro Gln Gly Pro Pro Asp Asn Lys Cys Ser
            20                  25                  30

Leu Pro Ser Ile Ser Asn Leu Leu Gly Leu Ala Asp Gln Pro Thr Ser
        35                  40                  45

Glu Thr Ser Ala Gln Tyr Thr Pro Arg Ala Glu Ala Thr Thr Arg Leu
    50                  55                  60

Leu Ala Thr Gly Lys Gln Ala Thr Lys Gly Asn Asn Leu Ala Val Ile
65                  70                  75                  80

Leu Thr Ser Gln Thr Ala Ala Gln Gln Ser Asn Ser Ser His Tyr Ser
                85                  90                  95
```

```
Asn Ala Val Gln Ser Val Arg Gln Thr Ser Glu Thr Ser Phe Asp Gly
            100                 105                 110

Tyr Asn Ser Pro Ser Asn Lys Ser Val Ser Gln Leu Pro Ala Thr Gly
        115                 120                 125

Tyr Tyr Phe Glu Ala Thr Pro Pro Pro Gly His Met Glu Met Glu Pro
    130                 135                 140

Arg Pro His Met Thr Ser Val Ser Arg Val Pro Val Gln Ala Pro Phe
145                 150                 155                 160

Ala Gln Ser Ala Tyr Ser Ala Pro Tyr Gly Met Ala Pro Ser Asn Pro
                165                 170                 175

Met Ala Ala Tyr Tyr Pro Thr Met Gln Pro Thr Pro Pro Pro Gln Gln
            180                 185                 190

Pro Gln Ile Ser Ser Leu Tyr Tyr Gln Arg Pro Leu Pro Gln Ala Phe
        195                 200                 205

Pro Pro Met Pro Val Asn Val Ser Met Gly Pro Gln Ser Gly Ala Asn
    210                 215                 220

Pro Trp Gln His His His Tyr Ile Ser Pro Ser Ala Ala Ser Gln Asp
225                 230                 235                 240

Arg Tyr Ile Cys Gln Thr Cys Asn Lys Ala Phe Gly Cys His Asn Tyr
                245                 250                 255

Asp Ser Ser Ser Ser Asn Gly Thr Ala Met His
            260                 265


<210> SEQ ID NO 16
<211> LENGTH: 291
<212> TYPE: PRT
<213> ORGANISM: Chaetomium globosum

<400> SEQUENCE: 16

Met Ala Asn Thr Met Val Thr His Tyr Ala His Val Pro Gln His Ser
1               5                   10                  15

Leu Gln Tyr Gly Tyr Met Pro Pro Pro Ala Ala Lys Cys Ser Leu Pro
            20                  25                  30

Ser Ile Ser Asn Leu Leu Gly Leu Ala Asp Gln Pro Thr Ser Glu Thr
        35                  40                  45

Ser Pro Gln Ser Gln Gln Gln Gln Gln Ala Gln Gln Gln Gln Gln Gln
    50                  55                  60

Gln Cys Met Ser Ser Ser Trp Trp Asp Met Gly His Leu Asp Thr Asp
65                  70                  75                  80

Ser Thr Pro Ala Gln Gly Ser Lys Pro Glu Thr Asn Ser Ser His Tyr
                85                  90                  95

Thr Asn Pro Val Thr Ile Arg Thr Ser Ser Asp Ala Ser Phe Glu Gly
            100                 105                 110

Phe Asn Ser Pro Ser Thr Arg Ser Val Ser Gln Val Pro Asn Gly Ser
        115                 120                 125

Asn Tyr Phe Phe Glu Thr Thr Pro Pro Leu Gln Met Glu Ala Asp Ala
    130                 135                 140

Arg Gln Met Thr Ala Ala Ala Ala Val Ser Val Gln Ala Ser Ala Tyr
145                 150                 155                 160

Gln Pro Gln Tyr Ala Pro Gly Pro Ala Tyr Met Ser Gln Pro Ala Met
                165                 170                 175

Thr Ser Tyr Tyr Pro Pro Met Gln Ser Ala Ala Pro Pro Gln Thr Gln
            180                 185                 190

Met Ser Gly Leu Tyr Tyr Gln Arg Pro Leu Pro Gln Pro Pro Pro Met
```

```
        195                 200                 205

Ser Met Ser Met Thr Leu Ala Pro Thr Ala Gly Asn Pro Trp Gln His
    210                 215                 220

His His Tyr Ile Ala Pro Ser Ala Ser Gln Asp Arg Tyr Ile Cys Pro
225                 230                 235                 240

Thr Cys Ser Lys Ala Phe Phe Pro Gly Cys Gly Lys Ala Phe Ser Val
                245                 250                 255

Arg Ser Asn Met Lys Arg His Glu Arg Gly Cys His Asn Tyr Asp Ser
            260                 265                 270

Ser Ser Thr Thr Ser Ser Thr Gly Thr Met Asn Ser Asn Thr Gly Gly
        275                 280                 285

Ser Arg Pro
    290


<210> SEQ ID NO 17
<211> LENGTH: 214
<212> TYPE: PRT
<213> ORGANISM: Fusarium oxysporum

<400> SEQUENCE: 17

Met Glu Glu Gln Lys Cys Ser Leu Pro Ser Ile Ser Asn Leu Leu Gly
1               5                   10                  15

Leu Pro Thr Ser Glu Ser Ser Pro Thr Ser Arg Gln His Ser Pro Arg
            20                  25                  30

Phe Glu Val Pro Pro Pro Ser His Gly His Ser Arg Ala Gly Ser Glu
        35                  40                  45

Trp Ala Lys Ser Ser His Arg Ser Thr Asp Ala Ser Phe Glu Gly Tyr
    50                  55                  60

Ser Ser Pro Thr Arg Lys Pro Ser Asn Gln Ala Tyr Pro Gly Ser Ala
65                  70                  75                  80

Pro Arg Thr Tyr Tyr Tyr Glu Thr Thr Pro Pro Leu Glu Ala Asp Ala
                85                  90                  95

Gln Arg Gln Ala Ser Val Thr Ala Ala Thr Pro Pro Ala Thr Ala Pro
            100                 105                 110

Tyr Pro Gln Gln Ala His Pro Thr Val Tyr Ala Asn Pro Ala Pro Val
        115                 120                 125

Gly Ala Tyr Tyr Pro Ala Ala Gln Val Pro Pro Ala Val Gln Pro Gln
    130                 135                 140

Glu Met Asn Pro Tyr Tyr Gln Arg Pro Leu Pro Gln Ala Tyr Pro Pro
145                 150                 155                 160

Pro Val Ser Met Pro Ala Pro Ala Pro Ser Gly Ala Asn Pro Trp Gln
                165                 170                 175

His His His Tyr Leu Asn Gly Ala Ala Ala Ser Gln Asp Arg Tyr Ile
            180                 185                 190

Cys Pro Thr Cys Asn Lys Ala Phe Gly Cys His Ser Phe Glu Phe Asn
        195                 200                 205

Gly Ser Val Ile Arg Gly
    210


<210> SEQ ID NO 18
<211> LENGTH: 936
<212> TYPE: DNA
<213> ORGANISM: Aspergillus nidulans

<400> SEQUENCE: 18

atggatctcg ccaacctcat ctcccaaccg gggcctgagc ctgctctgac ggccaaatca     60
```

```
agatacagcc ctcctgcctt tgaaccgggc tccttctacg ccgcatctac ttcattcacg    120

cggacacaag cgccactatc gcctccagtc gaggatagat cttctcgctg ctcactgcca    180

tcaatctctg cgcttcttga cagcgcagac ggcgcctcga cacaagctcc aaagcgccaa    240

cggctcagct ctccaatgca ccgtgaaccg cttgacaaga acccatctgc cggcgctgct    300

cccatccgtc tcccgcccac tcctccattg cgccccggct ccggcttcca cagcgccggc    360

cactcgccct cgagctccat ctcatccatc tcgatgatca agtccgagta cccggcacca    420

ccatcagctc cagtctctct tccgggcctt cccagcccaa ccgaccgctc gtccatctcg    480

agccaagggt ctgcgccgca gcaccagcat ggtccctacg cctcgccagc tcccagcgtg    540

gcgccctctt actcctcgcc cgttgagccc tcaccctcat cggcaatgta ctaccaacac    600

cagcggcccg catcctcagg cacataccag gctcctccac ccccgccgca acaccagccc    660

atgatctcgc ccgtgacacc ggcctggcag caccaccact acttccctcc ttcctcaaac    720

acaccctacc agcagaacca cgaccgatat atctgccgca cctgccacaa ggcgttctcg    780

cggccctcga gtctgcgcat ccacagccat agccacaccg gcgagaagcc atttcggtgc    840

acacatgccg gatgcggcaa agcctttagt gtacggagca acatgaagcg ccatgagcgc    900

ggctgccata ccgggagggc tgtcgcgatg gtgtaa                              936
```

<210> SEQ ID NO 19
<211> LENGTH: 960
<212> TYPE: DNA
<213> ORGANISM: Aspergillus oryzae

<400> SEQUENCE: 19

```
atggatctcg ccagccttat cactccgggt cctgaaccca tctacaagtc tcgggcatcc     60

tacagccctc ctcccagctc tgcgggttcc tacaagcgcc cggctgaaca cgactcttac    120

ttctcgtact cgcgcgcccc gcaagcccct ctttccccgc cagtcgagga ccagcccaag    180

tgctctcttc cctctatctc gactctcttg gaaggcgccg acagcgcatc gacatatgct    240

gcaaagcgtc aaagaaccag cccacccccg cgcagggagt ctgagttccg ttcaccttat    300

gactcagtct caacaccaaa tggccctcct actccacctt tgcgccctga atcgggcttc    360

cacagcggcc accactctcc ctctgcttcg tccgtgacta gtggaaaggc catcaagctc    420

gagtcgtact cgcaaacccc catgacactg cctagcccgt ccgatagatc ctcgatctcc    480

agccagggct ctgtccacca cgtttccgct gctccctacg cttctcctgc ccccagtgtg    540

gcctcgtact cttcgccggt tgaatcctcg gctccgtccg ccatgtacta ccagagacct    600

tccggctcct accagacccc cgctactgtg cctagcccct ccgctgctcc tatgcctgca    660

tctgccacac accagcagat gattactccc gtcactccgg cctggcagca ccaccactac    720

ttcccgcctt ccagctcggc accctaccaa cagaaccacg accggtatat ctgccggact    780

tgccacaagg ccttctccag accatccagc ctgcgcatcc actctcacag ccacactggc    840

gagaagccat tccgctgcac ccacgccggc tgcggtaagg cgttcagcgt acgaagcaac    900

atgaagcgcc acgagcgcgg ctgccacacc ggacgccccg tcgccaccgc catggtataa    960
```

<210> SEQ ID NO 20
<211> LENGTH: 1008
<212> TYPE: DNA
<213> ORGANISM: Aspergillus clavatus

<400> SEQUENCE: 20

```
atggatctcg caaacctcat ctcgcatccc acctccgagg ctgcctcgac tttcaagtcg     60

aggtcagctc agagtcctcc cgcctttcaa gcgaaccctt acaagcgtct ctccggatcg    120

tcgatgagct cttacttcac ctccgtaccg acgaccgcga catcgtattc tcgcaccccg    180

cagccaccac tctccccacc cgtcgacgac cggcccagat gttcgctgcc ctcaatctcg    240

actctactgg agggtgcaga cagcgcagcc gcacatgcag cgaaacgcca aagaactagc    300

ctctcggcgc atagggatct tgatgcccgt cctcagtcgc aaccgtatga cacgatcacc    360

ccacatgcct tgccacctac gccgccattg cgtcctggct cgggttttcg cagcaacggc    420

cattcgcctt cagcctcgtc tgtttccgca acgagcgcca gcacggtgat caagaccgaa    480

acatatcctc agcctcacat cggccttccc agcccgacag atcgctcctc catctccagc    540

caaggatcgg tgcagcatgc gcccggagcg ccgtatgcgt cgccagcgcc tagcgtggca    600

tcttactcgt cacctgtcga gccttccaca ccgtccagcg cagcctacta tcaaagaaag    660

gccccttcag ctcccttcca gaacccaggc agcgtcccct cagcatcggc cgctcaccag    720

cagcttatca cccccatcac ccccgcctgg caacaccacc actatttccc cccatccagc    780

tcaaccgcct accagcagaa ccatgatcgc tacatctgcc gcacctgcca caaagcgttc    840

tcgcgccctt ccagtctgcg catccactcc cacagccaca cgggcgagaa gccctttcgc    900

tgcacacacg ccggctgcgg caaggccttc agcgtgcgaa gcaatatgaa gcgccatgag    960

cgtggatgcc atacaggccg cccagtcgcc actgctatgg tgtcataa                1008
```

<210> SEQ ID NO 21
<211> LENGTH: 978
<212> TYPE: DNA
<213> ORGANISM: Aspergillus niger

<400> SEQUENCE: 21

```
atggatctcg ccagcctcat ctcccacccg ggacccgatc ccatcatgaa gtctagagcc     60

tcatacagcc ctcccatgac ttcctacaag cgctccatcg aacacacctc ggactcctac    120

ttcccctccg tcccgatctc ctacacccgc tccccgcagc ctcctctctc cccgcctgtc    180

gaggaccagt cccccaagtg ctctcttccc tccatctcta ccttgctcga gggcgcagat    240

ggcgcagcta tgcatgcagc aaagcgcact agaatgaccc ctcctctgca acgcgacctt    300

gattcccgcc aacagtcgca agcatatgac ctcaaagcta acggccccca aatcgccttg    360

ccccccaccc ccccattgcg ccccggttct agcttccaca gcgccggaca ctccccccgcc    420

tcctccatct ctgctgccag cgatgctgct gcgcccaagc gctccgactc ctaccctcaa    480

gtgcccatgg ctctgcctag cccctcggat cgctcgtcca tctccagcca gggttcagtt    540

cagggtgtct ccagtgcttc ctacgcttct cccgctccca gcgtctcttc ctactcctct    600

cccattgagc cttcggcctc gtccgccatg ttctaccaac gcacggctcc ctccacttcc    660

gccgctcctc tcccgacgcc agcagcaccg caacagatta tctcccctgt gaaccctgcc    720

tggcagcacc accactactt ccctccctcc agcaccacgc cctaccagca gaaccatgat    780

cgctatatct gccgcacctg ccacaaggcc ttctcgagac cctccagcct gcgcatccac    840

tcccacagcc acacgggcga gaagcccttc cgctgcaccc acgccggttg tgggaaggcc    900

ttcagcgtgc gcagcaacat gaagcgtcat gagcgtggct gccacagtgg tcggcccgtc    960

gcaaccgcca tggtttaa                                                  978
```

<210> SEQ ID NO 22
<211> LENGTH: 978

<212> TYPE: DNA
<213> ORGANISM: Aspergillus kawachii

<400> SEQUENCE: 22

```
atggatctcg ccagcctcat ctcccacccg ggacccgatc ccatcatgaa gtctagagcc     60
tcatacagcc ctcccatgac ctcttacaag cggtccatcg aacagacttc cgactcatac    120
ttcccctccg tcccgatctc ctacacccgc tccccgcagc ctcctctctc cccgcctgtg    180
gaggaccact ctcccaagtg ctctcttcct tccatctcta ccttgcttga gggcgcagat    240
ggcgcagcta tgcacgcagc aaagcgtact agaatgaccc ctcctctgca gcgcgacctt    300
gattcccgcc aacagtcgca agcatatgac ctcaaagcca acggccccca aatcgccctg    360
ccccccacgc cccattgcg ccctgggtct agcttccaca gcgccggcca ctccccccgct    420
tcctccatct ctgctgccag cgatgctgct gcgcccaagc gctccgactc ctaccctcaa    480
gtgcccatgg ctctgcctag cccttcggat cggtcgtcca tctccagcca gggttccgtt    540
cagggtgtct ccagcgcttc ctacgcttct cccgcgccca gcgtctcttc ctactcctct    600
cccattgagc cttcggcctc ctccgctatg ttctaccagc gcacggcgcc ttccacttcg    660
gccgctcctc tcccgacacc ggcagcaccg caacagatta tctcccctgt gaaccctgcc    720
tggcaacacc accactactt ccctccctcc agcaccacgc cctaccagca gaaccatgat    780
cgctatatct gccgcacctg ccacaaggcc ttctcgagac cttccagcct gcgcatccac    840
tcccacagcc acacgggcga gaagcccttc cgctgcaccc acgctggttg tgggaaggcc    900
ttcagtgtgc gcagcaacat gaagcgtcat gagcgtggtt gccacagtgg tcggcccgtc    960
gcaactgcca tggtataa                                                   978
```

<210> SEQ ID NO 23
<211> LENGTH: 1011
<212> TYPE: DNA
<213> ORGANISM: Aspergillus fumigatus

<400> SEQUENCE: 23

```
atggatgtcg caagcctcat ctcgccttct gaatcggata ctgtcccgac cttcaggtca     60
agatcgattc agaattcatc agccagccat tacaagcgcc tctccgaaca atcaacaggc    120
tcttacttct ctgctgtgcc aacacataca acgtcttact ctcgtacccc tcagccacca    180
ctgtcccctc cagcggagga ccagtccaaa tgctcgcttc cttccatctc gatcctgctt    240
gagaacgcag acggtgccgc cgcacacgca gcaaaacgcc aacgaaacag cctatcaacg    300
cacagggatt cggatccccg gcctccatat gactcgatca caccacacgc catgccgcca    360
acgccgccat tgcgtcccgg ttcgggcttc cacagtaatg gccattctcc ctcgacatca    420
tctgtctctg ccgctagctc cagcgctttg atgaaaaaca cagaatcgta tcctcaggcg    480
ccaattgggc ttcctagtcc aacggatcga tcctcgatct cgagccaagg gtccgttcag    540
catgccgcca gcgctccata tgcttcgcct gctcccagcg tatcgtcctt ctcttctccc    600
atcgagccct ctacaccatc aactgccgct tactaccaaa gaaatcctgc gccgaacacc    660
ttccaaaacc caagcccctt cccccaaaca tccacagcat ctcttccctc cccgggtcat    720
caacagatga tttctcccgt cacccccgcc tggcaacatc accactactt ccccccgtcc    780
agttccacgt cttaccagca gaaccatgat cgctacatct gccggacatg ccacaaggcc    840
ttttcgcggc cctccagcct gcgcatccac tcccacagcc acactggcga gaagcctttc    900
cgttgcacac atgccggctg cggcaaggcc ttcagcgtac ggagcaatat gaagcgtcat    960
```

gagcgtggtt gccatacggg ccgcccagtt gctaccgcca tggtccaata g 1011

<210> SEQ ID NO 24
<211> LENGTH: 1005
<212> TYPE: DNA
<213> ORGANISM: Neosartorya fischeri

<400> SEQUENCE: 24
atggatgtcg caagcctcat ctcgccttct gaatcggata cagttccgac cttcaggtca 60
agatcgattc agaattcatc agccagccat tacaagcgcc tctccgaaca atatacgggc 120
tcttacttct ctgctgcacc aacacatacg acgtcttact ctcgtacccc tcagccacca 180
ctgtcccctc cagccgagga ccagcccaaa tgctcgcttc cttccatctc gattctgctt 240
gagaacgcag acggtgccgc cgcacacgca gcaaaacgcc aaagaaccag tctatcaacg 300
cacagggatt cggggcctcc atatgactcg atcacaccac acgccatgcc accaacgccg 360
ccactgcgtc ctggttcggg cttccacagt aatggccatt ctccctcggc atcgtctgtc 420
tctgccacca gctccagcgc tgtgatgaag aacaccgaaa cgtattctca ggcgccaatt 480
gggcttccta gtccgacgga tcgatcctcg atctcgagcc aagggtccgt tcagcatgcc 540
gccggcgctc catatgcttc gcctgctccc agcgtgtcgt ccttctcttc tcccgtcgag 600
ccctctacac catcaactgc cgcttactac caaagaaacc ctgcgccgaa caccttccaa 660
aacccaggct ccttccctcc aacatccgcg gcctctcttc cttccccggg tcatcaacag 720
atgatttctc ccgtcacccc cgcctggcaa catcaccact acttcccccc gtccagttcc 780
acgccttacc agcagaacca tgatcgctac atctgccgga catgccacaa ggccttctcg 840
cggccatcca gcctgcgcat ccattcccac agccacactg gcgagaagcc tttccgctgc 900
acacatgccg gctgcggcaa ggcctttagc gtacggagca atatgaagcg tcacgagcgt 960
ggttgccata cgggccgccc ggttgctacc gccatggtcc aatag 1005

<210> SEQ ID NO 25
<211> LENGTH: 960
<212> TYPE: DNA
<213> ORGANISM: Aspergillus flavus

<400> SEQUENCE: 25
atggatctcg ccagccttat cactccgggt cctgaaccca tctacaagtc tcgggcatcc 60
tacagccctc ctcccagctc tgcgggttcc tacaagcgcc cggctgaaca cgactcttac 120
ttctcgtact cgcgcgcccc gcaagcccct ctttccccgc cagtcgagga ccagcccaag 180
tgctctcttc cctctatctc gactctcttg gaaggcgccg acagcgcatc gacatatgct 240
gcaaagcgtc aaagaaccag cccacccccg cgcagggagt ctgagttccg ttcaccttat 300
gactcagtct caacaccaaa tggccctcct actccacctt tgcgccctga atcgggcttc 360
cacagcggcc accactctcc ctctgcttcg tccgtgacta gtggaaaggc catcaagctc 420
gagtcgtact cgcaaacccc catgacactg cctagcccgt ccgatagatc ctcgatctcc 480
agccagggct ctgtccacca cgtttccgct gctccctacg cttctcctgc ccccagtgtg 540
gcctcgtact cttcgccggt tgaatcctcg gctccgtccg ccatgtacta ccagagacct 600
tccggctcct accagacccc tgctactgtg cctagcccct ccgctgctcc tatgcctgca 660
tctgccacac accagcagat gattactccc gtcactccgg cctggcagca ccaccactac 720
ttcccgcctt ccagctcggc accctaccaa cagaaccacg accggtatat ctgccggact 780
tgccacaagg ccttctccag accatccagc ctgcgcatcc actctcacag ccacactggc 840
gagaagccat tccgctgcac ccacgccggc tgcggtaagg cgttcagcgt acgaagcaac 900
atgaagcgcc acgagcgcgg ctgccacacc ggacgccccg tcgccaccgc catggtataa 960

<210> SEQ ID NO 26
<211> LENGTH: 960
<212> TYPE: DNA
<213> ORGANISM: Aspergillus terreus

<400> SEQUENCE: 26
atggatctcg ccagcctaat caccccggga cctactccct tcgcatctcg tccgcctcga 60
gcttcctaca gtcccccggc ttcttcgtcc ggttcataca aggcccctaa tgagcctcat 120
tatacggggt catacttccc cgccatgcct actgcgactc cagtgaccac cactacttcc 180
tactcgcgct cgccgcaacc gcctctctct cctcccgtcg aggaccagcc caagtgctct 240
ctcccttcca tctccaccct tctcggtgcc gcagacagcg ccccaatgcc cccagctaag 300
cgccagcgcc tcagtacccc cgcgcgcaga gaatccgata gctggctcca gacaacacca 360
tgcctgcctc cgacccccccc gttgcgtcca ggctccggct tccacagcag cggccaccgc 420
tcgccatcat ccaacaagcc caccgaatcg gcgcccttcc cgcaacagcc ccccgtgacg 480
ctccccagtc ccaccgagcg ctcctccatc tccagccagg gctccgcgca cgcgccgtac 540
gcttcgcccg cccccagcgt cgcctcgtac tcgtctcccg tcgagccctc cccggctccc 600
tccacgctgt actaccagcg ccccgccgcg cctccagcgc cttccgccgc cgccgctgct 660
cccgctcccg cgcagccctt gatctccccc gtcaccccgg cctggcagca ccaccactac 720
ttcccgccct ccagctccac cccctaccag cagaaccatg accggtacat ctgccgtacc 780
tgccacaagg cattctcgcg cccctcgagt ctgcgcatcc attcgcacag tcacaccggc 840
gagaagccct tccgctgcac ccacgccggc tgcggcaagg ccttcagcgt ccgcagcaac 900
atgaagcgcc atgagcgcgg atgccacagc ggccgtccgg ttgctaccgc tatggtatga 960

<210> SEQ ID NO 27
<211> LENGTH: 906
<212> TYPE: DNA
<213> ORGANISM: Penicillium chrysogenum

<400> SEQUENCE: 27
atggatctct ccaacctcct ctctcacagc gcggctgtca agccgatcta tactcctgtc 60
gagtccagtt actataagcg ctcgccgcct ctgtcgccgc cagccgaaga gcccaaggtc 120
tcattgcctt caatctcgtc tctctttgag ggtgctgatg gtgctcagca cgcagctacc 180
tcgctaaccc taaaccttcc agagcgccaa cgcttgtcac catctctcgg tgaccgccat 240
gtccgggttc agtcctacga actgccccca acaccacctc tgcgccccgg ctctggccac 300
gcccaccgcc gcgcatctcc cgtggagtcg ctgtctcaca aggaagcaca ccagcatcac 360
cttcaccgtt cctctatctc cagcaacagc tcagtccaca tccctcgcaa cacagtaccc 420
tacgcctcgc ctgtaccaag cgtctcatcc tacacatctc cagtcgacgc tcctcaacag 480
ccaatgtact accctcgccc accaaccaca tcctccttcc agccctcaac accagcatca 540
gcaccccaga tgccccctgt ccaggtccag acgcagcagc cgcactcgca ctctcactcg 600
tcttcggctc tcatctctcc tgtcaccccg gcctggcaac accaccacta cttcccgccc 660
tccaccacag ccccgtacca gcagaaccac gaccgctata tctgccgtac atgccacaag 720
gctttctcgc gcccttcctc cctgcgcatc cactcgcact cgcacactgg cgagaagccc 780

```
ttccgctgca cgcatgccgg ctgcggtaag gctttctccg tgcgcagtaa catgaagcgc    840

catgagcgtg gctgccattc tggtcgccct gcccctgccc ctgctgctac tgcgcttgtc    900

gtatag                                                               906


<210> SEQ ID NO 28
<211> LENGTH: 1011
<212> TYPE: DNA
<213> ORGANISM: Coccidioides immitis

<400> SEQUENCE: 28

atgaacgttt caagcctgat cacttgcgat cagccgcacc aattgcgcgc gcctgcatct     60

tcatattctg agcaccgtcg atccccatcc atccccaagc ctttgcagac ggagagcagt    120

tcatgcgctt ctccatactc gcggttcgag cgtctccctc tttcaccgcc ggaggaggat    180

ggcaagacac agttctcact tccttctatc tcgtctcttc ttcggggcgt agatggtgtt    240

tctgatgcgc acgttgctaa gagacaacga accaaccctc ctcctagcat tgacttaggg    300

atggagagac ggactataga ccaaacatta aagcagaggc cagcgctgcc tttgacgcct    360

cctctaaggc ctgagtctgg catgaatagc acaagccagt cgccgtcaac atcatcgcca    420

ccacgaagcg ccatctcact accgagtctt gttcggagtt atccgtctcc agtttcagaa    480

gttccagagg gacgacggat gtcacagata tcgcgacatt cgcgaggggc ttcgacgtcg    540

caaacttctc aactttcagg cccagaaaca cgttacccat cgccaccaaa tgtcaactct    600

ccaacctttg ctgcccctgt tgaaccagcg ccaaagccga cagaatacta cccagccagc    660

cgaccggtaa cgtttccgcc tgtggcgttc gcagttctgc caagccagcc aactcatcct    720

caggtgcttc ctcttggaag tcctgcgtgg cagcaccatc attatttccc tccttccaac    780

acagcaactt atcctctcaa tcacgataga tacatctgcc gaatatgtca taaggctttc    840

tcaagaccgt ccagcctgcg aatacactcc cacagtcata ctggcgagaa gcctttccgg    900

tgcccccatg ccggctgtgg gaaagcgttt agcgtgcgaa gcaacatgaa gcgacacgaa    960

aggggttgcc atcctggaag atcagcacca ccatcggccc tggttaactg a            1011


<210> SEQ ID NO 29
<211> LENGTH: 1038
<212> TYPE: DNA
<213> ORGANISM: Ajellomyces capsulatus

<400> SEQUENCE: 29

atgaatttat cccacttggt gaccagctat catagccctc cttcgacgta tccacactca     60

ggcacttcgc aaaagcgcca gtccttgcag agcgaatctt cattatctgt atcgaacgga    120

tactacgatc gcaatgcttc aaatcttgca tatgcccgct ctcctcaacc acccttatcc    180

ccacctgtcg aagagcagtc cagattctct cttccttcaa tatctagttt attgcaagga    240

gctgaccaac tctctcctgt tcatatagct aaaaaaacatc gtcccaatcc actctcaact    300

ggagaagttg atttaaaatc gcagggccat ggagccaccc aaaagcccat acacaggccg    360

agaatgattt taccaccgac ccctcccatg cgcccaggct ccggattaga tggaagaaat    420

cactctcctg ccggatcgtc gccatcgtct gcacactctc ccatttcagt agccaatctc    480

acaagttcgt catcggcgga cccttcctat cagcatcgga tgccccaagg tccgttaccc    540

ccacagtcaa ccagatcgtc cgtatctcaa aattctcctg tctctctacc cgaaaagcat    600

tacgctccat cctccaattt acccaccagc tcgactccat tcgcttcccc agttgaaccc    660

ctagcgaatt ctacggaata ttatcaccgc ccatcccatc cccttcttt ctcgacatct    720
```

```
attcctctgg cagccccgcc agcgcaacag caccatcacc attctatgat ctcaacctgg    780

caacaccacc actattttcc accgtcaaat acggctccct acccacaaaa tcatgacagg    840

tatatctgtc gaatatgtca caaggcgttt tctcggcctt ctagtctgcg gattcactcg    900

cacagccata ccggcgaaaa gccattcaaa tgcccgcatg tcaactgtgg caagtcattt    960

agtgtcagga gtaacatgaa gcgacatgaa cggggttgtc atacaggcag acctacgcaa   1020

gcagctttgg tgaattaa                                                 1038


<210> SEQ ID NO 30
<211> LENGTH: 1272
<212> TYPE: DNA
<213> ORGANISM: Uncinocarpus reesii

<400> SEQUENCE: 30

atgaacgttt ctagcctgat tagttgtgat cagactgctc ccttccacgg gtctgcaaca     60

tcatatttcg agcatcatca aagaatccga tcgccttcca ttcccaaaag atcacacgaa    120

gagaacagct catccgcctc tccctaccct ccttttgcaa ccctgcctct ttcgccacca    180

gaagatgacg ggaagacaac cttctcgctt ccttctatct catcccttct tcaaagcgtc    240

gacgctgctt ctgacactca cgttgccaaa cggcaacgag ccaacccccc tcctagcatt    300

gatttagctc tggagagacg aggtgcctgt gcggaccaag caatcagaca aaggccagcc    360

cttccactaa cgcctcccct gcgaccagag tcgggaatgg gcggtgtaaa tcactcgcca    420

tctgcatcat cccctccccg aaccgctatc tcactaccca gcctcattgg aagttaccca    480

tcgccagttt cagaggctcc agaaggacga cgaatgtcgc aaatctcacg acactcaagc    540

agaacttcca tctctcaatc ctcccaacat ccagggccgg aagcccgcta cccatcgcca    600

ccaactctca gctctccttc cttcgccgct cctattgaac cacctccaaa gccagagtac    660

tactcttctg gtgcccgacc gaccaacttt ccgccagtaa ctttcgctgt ccttccaagt    720

caaccaacgc atccgcagat ggtggccttg gggagtcctg cctggcagca tcaccactac    780

tttcctccat caaacacagc aacttaccca ctcaaccacg acagatacat ttgccgaata    840

tgccacaagg cattctcacg gccgtcaagc ctgcgaattc actcgcatag tcacacaggc    900

gagaagccgt ttcgatgccc ccatgccggc tgcgggaagg cattcagcgt gcgaaatcag    960

ccccgcagcc agcgctcgtt aattgaaaaa cggaaggggt acgcgatcgg atttgacgaa   1020

tgggttttga cgatgataac gcccacaata cggagtacca acgagcaaat ctacacaact   1080

gcatcgtgta agatcgcgaa cgtggcggtg atcaacatca atagaagaat tgccgagctt   1140

cgcaagtcat ttcgcaacag acgttcgaat gggacgttgt ccccgacgaa gcgccgcgtc   1200

aaattggcat tttccctgga ttgccaatct acatcctcat ccaggcttgc ccttttaccg   1260

cagtcccttt ga                                                       1272


<210> SEQ ID NO 31
<211> LENGTH: 744
<212> TYPE: DNA
<213> ORGANISM: Penicillium marneffei

<400> SEQUENCE: 31

atggataacg tgcctgcaag caaacgtgcc cgccatgact caggcgacta cagccgtggc     60

ttcttacctc caacaccgcc aatgcgcccc tgctccgggt tcacagaagg cagctcgcct    120

gcctctcttc cttctggacg atcacattct gcttctataa gcagcgcagt ttcgcatcca    180
```

```
tcacaccaac agcgtacatc tttaccatct atttctgcat ctcttcaaaa tacaccaatc    240

caccccttcag agcgtttatc catctcctct ctcgcctctc acgactcttc ccgcctttct    300

cacgccattc ccagcccttc atctaccaca gcctcgatca caaccacagc gactccatca    360

acgtcatatt attctacatc agaagagaaa gcatatccac gatcacatag cacatccgct    420

ccagtgaccc catcaacact tgtcccacca ccacccgcca tgctctcgcc tgtgaaccac    480

ccaggctggc aacaccacca ctacttccca ctttcgacta cgacatcata cccacaaaac    540

cacgagcggt atgtctgccg tacatgccac aaggcattct ctcgtccatc cagtcttcga    600

atccactcgc atagccacac tggcgagaag ccattccgat gcacacatgc aggctgcgga    660

aaggcgttca gtgtgcgcag caatatgaag cgccacgagc gcggctgtca tagcggacga    720

cctatgacgg caactgttgt ctaa                                            744
```

<210> SEQ ID NO 32
<211> LENGTH: 954
<212> TYPE: DNA
<213> ORGANISM: Botryotinia fuckeliana

<400> SEQUENCE: 32

```
atggcctcat cgttggtttc aaacccttat acagtccatc ctatggctca acactcttcc     60

tacacatacg ttaacgcacc tcaaccacca ccctcaccac ccgtagacga aacttcaaag    120

tgttccctac catctatttc aagtctgttg ggtttggccg atggatcgag tccaacagag    180

caggctcagc aacagtcatc gccacaacaa gcagctttca aggaagatta tagaccagag    240

tctggacatc agtacggtcc ttcctcatca atgagctctc gaggtgctct tccacctaca    300

cccccaatgc aatctgacgg tggattcgac ggcagacaat cgccgtctca agcatctact    360

tcatcatatt cagtagtttc tgcgccaaat tattacttta atccttctca agtctcggcc    420

atcaacaata tggagcctca tgcacaacgc cagccagtcc aaactgttac tcgaagagtt    480

tcaatgccag tgtcttcaat gcaatatggc cattctccgt tcaacggatc ctacactatg    540

tctcctggcg cccagtcttt gagctcttac tatccaagcc cgatacaaac acaatctccc    600

caagtttctt cactatacta tcaaagacca cttccacagc aatttcctcc gccaatgatg    660

ccagtgtctg tgactctgac tccatcatcc ggtgctaatc catggcaaca tcatcactat    720

atctctcctt cctcagcagc ctcatttcct cagtcacaag atagatacat ctgtcagact    780

tgtaacaaag ctttttcgag accatcgagt ctccgaatcc acagccactc acataccggc    840

gagaaaccct tcaagtgtcc acatcaaaac tgtgggaaag ccttcagcgt taggagcaac    900

atgaagagac acgagcgagg ttgtcacagt tttgaaagcg cttcaatggt ctga          954
```

<210> SEQ ID NO 33
<211> LENGTH: 918
<212> TYPE: DNA
<213> ORGANISM: Neurospora tetrasperma

<400> SEQUENCE: 33

```
atggcaccca cgacgttaac gcctcaatat cctgcccagc cttatggctt cgctccgcca     60

ccctcccctc ctttggacga ctccaacaag tgctccctgc cctcgatttc gaacctgctt    120

gtcatggccg atcagggatc tcctacctca gagacatctc ctcagtctca gcaattgcac    180

ttctcaaagc ctgacaaccg tcccaactct tcccagtttg gcaacccagc atcgatcagg    240

gcgaacctcc cccctagtcc tcccatgtct tcggaagctt cttttgaagg ataccgctct    300

ccttcaagca agccagcaag ccagtctcag ggcagctcca actactacta tgagaccacg    360
```

```
ccgcctttga gccagcatga agccgactcc cggcagatgg ccactgctgc acccagagcc    420

cctgttcagt catcaacctt ccaaacacag tacccgtcgt cagccggcta ctcgagtcag    480

tcaggcatga accottatta ccctcccatg cagccgacac cccctccgca gcagcagatg    540

tcgggcttgt attatcagcg accactccct cagactttca cccctgctgt gccagttcca    600

gtcactctcg caccagtcac gggagccaac ccttggcaac atcaccacta tattgctcct    660

tcttccactg catcttttcc gcagtctcaa gaccggtaca tctgccagac ttgcaacaag    720

gccttctctc gaccgagctc attgcgaatc cacagccact ctcacactgg tgagaagcct    780

ttcaagtgcc cccatgcagg ctgcggaaag gccttcagcg ttcgcagtaa catgaagcgt    840

catgagcgtg gctgccacag ttttgagagc agcaacggca gaagcagtgg caacagcaac    900

aacggcgcat ctgcctag                                                  918
```

<210> SEQ ID NO 34
<211> LENGTH: 918
<212> TYPE: DNA
<213> ORGANISM: Neurospora crassa

<400> SEQUENCE: 34

```
atggcaccca cgacgttaac gcctcaatat cctgcccagc cttatggctt cgctccgcca     60

ccctcccctc ctttggacga ctccaacaag tgctctctac cctcgatttc gaacctgctt    120

gtcatggccg atcagggatc tcctacctca gagacatctc ctcagtctca gcaattgcac    180

ttctcaaagc ctgacaaccg tcccaactct tcccagtttg gcaacccagc atcgatcagg    240

gcgaacctcc cccctagtcc tcccatgtct tcggaagctt cttttgaagg ataccgctct    300

ccttcgagca agccagcaag ccagtctcag ggcagctcca actactacta tgagaccacg    360

ccgcctttga gccagcatga agccgactcc cggcagatgg ccactgctac acctagagcc    420

cctgttcagt catcaacctt ccaaacacag tacccgtcgt cagccggcta ctcgagtcag    480

tcaggcatga acccttatta tcctcccatg cagccgacac cccctccgca gcagcagatg    540

tcgggcttgt attatcagcg accactccct cagactttca cccctgctgt gccagttcca    600

gtcactctcg caccagtcac gggagccaac ccttggcaac atcaccacta tattgctcct    660

tcttccactg catcttttcc gcagtctcaa gaccggtaca tctgccagac ttgcaacaag    720

gccttctctc gacccagctc attgcgaatc cacagccact ctcacactgg tgagaagcct    780

ttcaagtgcc cccatgcagg ctgcggaaag gccttcagcg ttcgcagtaa catgaagcgt    840

catgagcgtg gctgccacag ttttgagagc agcaacggca gaagcagtgg caacagcaac    900

aacagcgcat ctgcctag                                                  918
```

<210> SEQ ID NO 35
<211> LENGTH: 930
<212> TYPE: DNA
<213> ORGANISM: Magnaporthe oryzae

<400> SEQUENCE: 35

```
atggccgcca ccatgataca acagccctac ccaattcatc agcagcagtc gcagtacagc     60

tacatggttc agcctcaggg cccgccttcg ccgcccatgg acgacaacaa gtgctcgctt    120

ccatccatct cgaacctgct cggcttggcg gatcaaggat caccaacctc ggagacctcg    180

gcccaattcc gcgaggagca gaagcaacaa caagcagcac aacaatcaag acccaactcg    240

tcacactata gcaatgcagt ccagtctgtg cgccagggca tcccgccaac gccgccaatg    300
```

```
acttctgaga cctcattcga cggttacaac tcgccctcaa acaagtcggt cagccagctt    360
cccgccactg gctactactt tgaggcgacg ccacccccag gccacatgga gatggagccc    420
cgcccgcaca tgaccagcgt ttccagggtc ccagttcagg ctcccttcgc tcagtctgcc    480
tactcagctc cctatggcat ggcccccagc aacccgatgg cggcctacta cccgacgatg    540
cagcccacgc ctcctcctca gcagcctcag atctctagcc tttactacca gagacccctt    600
cctcaggcct tccctcccat gcctgtcaac gtctccatgg gtcctcagtc tggcgccaac    660
ccgtggcagc accaccacta catctcgcca tctgctgcgg catctttccc tcagtcccag    720
gaccgctaca tctgccagac ctgcaacaag gcattctccc gcccgagctc cttgaggata    780
cacagccact cgcacactgg cgagaagcct ttcaagtgcc ctcacgccgg ctgcggcaag    840
gctttcagcg tgcgcagcaa catgaagcgc cacgagaggg gctgccacaa ctatgacagc    900
agcagcagca acggcaccgc catgcactga                                     930
```

<210> SEQ ID NO 36
<211> LENGTH: 1029
<212> TYPE: DNA
<213> ORGANISM: Chaetomium globosum

<400> SEQUENCE: 36

```
atggcaaaca caatggtcac acactacgcg cacgtacctc aacatagcct tcagtatggc     60
tacatgccgc caccttcacc gccaatggat gaggcggcaa agtgctcgct cccctctatc    120
tcgaacctcc tcgggcttgc agaccaagga tcgccgactt cggaaacgtc gccccagtcc    180
cagcagcagc aacaggcgca gcagcagcag caacagcaat gtatgagcag ctcgtggtgg    240
gatatgggac acctagatac tgactcgacc ccagcgcaag gatccaagcc ggagacgagg    300
cccaactctt cgcattacac caacccggta accattcgga caggactccc gcccagcccg    360
cccatgtcct cggatgcatc ctttgaaggt ttcaactcgc catcgaccag gtcggtgagc    420
caggtgccga acgggtcaaa ctacttcttt gagacaacgc caccgcttca gatggaagcc    480
gatgcacggc agatgaccgc tgccgccgcc gtcccgcgag tttctgtcca ggcttcagcc    540
taccagcccc agtacgctcc cggccctgcg tacatgagtc aaccagccat gacctcatac    600
tatcctccga tgcaatccgc ggcgccaccg cagacgcaaa tgtccggcct ctactaccaa    660
cgaccgcttc ctcagtcttt tccgcctccg atgtccatgt ctatgactct tgcgccgacg    720
gccgggaacc cctggcagca ccatcactac attgcccctt cggcgtcagc atcctttccc    780
cagagccagg accggtatat ctgcccgacg tgcagcaaag ccttctcgcg gcccagctcg    840
ctgcggatcc acagccactc gcacacgggc gagaagccct tcaagtgccc gttcccgggt    900
tgcggcaagg ccttcagtgt gcgcagcaac atgaagcggc acgaacgtgg gtgccacaac    960
tacgacagca gcagcacgac gagcagcacc ggcaccatga acagcaacac cgggggaagc   1020
cgtccctga                                                           1029
```

<210> SEQ ID NO 37
<211> LENGTH: 831
<212> TYPE: DNA
<213> ORGANISM: Fusarium oxysporum

<400> SEQUENCE: 37

```
atggaggaac aaaagtgctc tctaccctca atctcgaacc tcttgggttt ggccgatgcc     60
ggctcaccca cgagtgagtc ctcaccaact tcacggcaac attctcctcg ctttgaagtt    120
cctccacctt cacatggtca tagccgagct ggatctgaat gggctaaatc atcgcaccgt    180
```

```
gggcttcccc ctacaccacc tatgagcaca gacgcatctt tcgaaggcta cagctccccc    240

acaaggaaac catccaacca ggcgtatcca ggctcagcac caagaacata ctattacgag    300

accacaccac ctctagaagc cgatgcacag cgtcaggcat cagtaacggc tattcctcga    360

gcaacacctc cagcaacggc tccttatcct cagcaagctc accccacggt atacgccaac    420

ccagcaccag tgggcgctta ttacccggcg gcacaggtgc ctcctgctgt ccagcctcaa    480

gagatgaacc cttactacca gcgccctctc ccacaggctt atcccccacc agtgagcatg    540

ccagcacctg ctccctcggg agcaaatcct tggcagcacc atcactatct taacccaact    600

ggagcggcgg cattcccgca aagccaggac cggtatattt gcccgacttg caacaaagcc    660

tttagcaggc ccagcagtct ccgaatccac agtcactcac ataccggaga gaaacccttc    720

aagtgtcccc atgctggatg tggcaaggct ttcagcgtac gcagcaacat gaaacgtcat    780

gagaggggct gtcacagctt cgaatttaat gggtctgtga ttcggggttg a             831


<210> SEQ ID NO 38
<211> LENGTH: 47
<212> TYPE: PRT
<213> ORGANISM: Aspergillus  nidulans

<400> SEQUENCE: 38

Met Ala Thr Leu Ala Ala Pro Pro Pro Pro Leu Gly Glu Ser Gly Asn
1               5                   10                  15

Ser Asn Ser Val Ser Arg Ile Thr Arg Glu Gly Lys Lys Ile Thr Tyr
            20                  25                  30

Lys Leu Asn Ile Met Gln Gln Pro Lys Arg Ala Arg Ala Cys Gly
        35                  40                  45


<210> SEQ ID NO 39
<211> LENGTH: 600
<212> TYPE: PRT
<213> ORGANISM: Aspergillus  nidulans

<400> SEQUENCE: 39

Met Ala Asp Asp Leu Asp Ala Glu Leu Leu Ala Leu Ala Gly Asp Asp
1               5                   10                  15

Ala Ser Ser Asp Glu Glu Thr Ser Pro Pro Pro Arg Lys His Thr Ser
            20                  25                  30

Ala Ser Pro Ala Gln Ser Ala Ser Pro Arg Ser Pro Glu Pro Thr Ser
        35                  40                  45

Thr Met Gly Arg Lys Gly Asn Ala Lys Pro Ala Arg Arg Ser Arg Lys
    50                  55                  60

Ser Arg Arg Asp Asp Asp Glu Glu Glu Asp Gly Glu Ile Ser Ala Asp
65                  70                  75                  80

Ser Leu Asn Ser Ala Ser Met Ser Glu Ser Glu Ala Pro Ser Asp Ser
                85                  90                  95

Glu Ser Ser Asp Ala Gly Val Glu Asp Glu Gly Pro Ile Tyr Pro Tyr
            100                 105                 110

Glu Lys Leu Tyr His Ser Ala Gln Asp Lys Gln Glu Ile Met Ala Leu
        115                 120                 125

Pro Glu Ile Gln Arg Glu Gln Ile Leu Ser Glu Arg Ala Gln Glu Val
    130                 135                 140

Asp Arg His Asn Gln Asp Leu Ala Leu Arg Arg Leu Leu Ala Ser Arg
145                 150                 155                 160

Glu Arg Glu Glu Ala Arg Lys Ala Lys Lys Asn Lys Arg Lys Ala Ser
```

```
                165                 170                 175

Ala Ala Asn Leu Asp Glu Gly Ser Arg Lys Ser Ser Arg Gln Lys Thr
            180                 185                 190

Thr Leu Gly Gly Arg Lys Val Gly Glu Ala Ser Glu Ala Ile Glu Ala
        195                 200                 205

Tyr Lys Arg Gln Arg Glu Gln Lys Gly Lys Arg Asp Glu Leu Arg Arg
    210                 215                 220

Arg Asp Thr Ala Thr Lys Asp His Lys Ser Lys Ser Arg Val Ser Asp
225                 230                 235                 240

Glu Asp Ala Asp Gly Glu Ser Glu Val Glu Trp Asp Asp Arg Glu Arg
                245                 250                 255

Ser Pro Thr Pro Pro Lys Asp Asp Pro Pro Ala Glu Leu Arg Asp Ile
            260                 265                 270

Gln Arg Ala Arg Val Gly Arg Thr Asn Phe Ala Gln Val Cys Phe Tyr
        275                 280                 285

Pro Gly Phe Glu Asp Thr Met Val Gly Cys Tyr Val Arg Leu Asn Val
    290                 295                 300

Gly Pro Asn Pro Asn Gly Val Asn Glu Tyr Arg Leu Ala Met Ile Thr
305                 310                 315                 320

Glu Ile Lys Glu Gly Lys Lys Tyr Ala Leu Glu Gly Ala Asn Gly Arg
                325                 330                 335

Thr Phe Thr Thr Asp Gln Tyr Ala Val Leu Ala His Gly Lys Thr Thr
            340                 345                 350

Arg Ala Phe Pro Phe Val Ala Cys Ser Asp Ser Pro Phe Thr Glu Ala
        355                 360                 365

Glu Phe Asn Arg Trp Arg Gln Val Met Ala Val Glu Asp Cys Lys Met
    370                 375                 380

Pro Thr Lys Ser Gln Leu Ala Lys Lys Val Met Asp Ile Asn Arg Leu
385                 390                 395                 400

Ile Asn His Gln Phe Thr Pro Glu Glu Leu Asn Glu Lys Leu Arg Lys
                405                 410                 415

Gln Gly Leu Leu Asp Thr Lys Thr Thr Phe Phe Lys Arg Val Asp Ile
            420                 425                 430

Glu Lys Lys Leu Lys Ile Ala Gln Glu Leu Gly Asp Asp Asp Glu Val
        435                 440                 445

Gly Arg Leu Gln Val Glu Leu Ala Asn Leu Gly Ser Ser Ala Lys Pro
    450                 455                 460

Arg Thr Glu Lys Lys Leu Thr Glu His Glu Arg Leu Ala Gln Leu Asn
465                 470                 475                 480

Leu Arg Asn Gln Lys Leu Asn Tyr Glu Asn Val Arg Arg Ala Gln Ile
                485                 490                 495

Glu Glu Arg Lys Ala Ser Arg Lys Ala Ala Ala Ala Ala Ala Arg Gly
            500                 505                 510

Glu Gly Ser Leu Asn Pro Phe Leu Arg Val Lys Thr Arg Ala Lys Thr
        515                 520                 525

His Tyr Asp Ala Asn Glu Ser Thr Pro Lys Ser Glu Asn Gly Ser Pro
    530                 535                 540

Ser Val Thr Pro Ala Ser Ser Thr Pro Asn Pro Ser Thr Pro Ala Arg
545                 550                 555                 560

Ser Ser Thr Pro Ser Asn Ser Gln Asn Lys Gln Ser Lys Gly Gly Gly
                565                 570                 575

Gly Lys Ile Arg His Arg Asn Met Asp Asp Glu Asn Ile Ala Ala Leu
            580                 585                 590
```

```
Asp Leu Asp Ile Asp Ile Glu Ile
        595                 600


<210> SEQ ID NO 40
<211> LENGTH: 612
<212> TYPE: PRT
<213> ORGANISM: Aspergillus  oryzae

<400> SEQUENCE: 40

Met Ala Asp Asp Leu Asp Ala Glu Leu Leu Ala Leu Ala Gly Asp Ala
1               5                   10                  15

Ser Asp Glu Glu Ala Ser Ser Pro Pro Arg Gln Lys Asp Ala Ser Pro
            20                  25                  30

Ser Ala Ser Pro Pro Gln Ser Pro Glu Glu Ser Ser Thr Met Gly Arg
        35                  40                  45

Lys Gly Thr Ala Lys Pro Val Arg Arg Gly Arg Lys Ser Arg Lys Asp
    50                  55                  60

Asp Glu Glu Asp Gly Glu Val Ser Ala Ala Glu Ser His Asn Ser Leu
65                  70                  75                  80

Asp Ser Ala Ser Met Val Glu Ser Glu Ser Gly Ser Asp Ser Glu Gly
                85                  90                  95

Ser Asp Ala Gly Ala Glu Asp Asp Gly Pro Ile Phe Pro Tyr Asp Lys
            100                 105                 110

Leu Tyr Tyr Ser Ser Lys Asp Lys Glu Glu Ile Met Ala Met Pro Glu
        115                 120                 125

Ile Gln Arg Glu Gln Ile Leu Ser Glu Arg Ala Gln Gln Val Asp Arg
    130                 135                 140

His Asn Gln Asp Leu Ala Leu Arg Arg Leu Leu Ala Ser Arg Glu Arg
145                 150                 155                 160

Glu Glu Ala Arg Gln Ala Lys Lys Asn Lys Arg Lys Ala Ser Met Ala
                165                 170                 175

Asn Leu Glu Asp Gly Gln Arg Lys Ser Ser Arg Gln Lys Thr Thr Leu
            180                 185                 190

Gly Gly Arg Lys Val Gly Glu Thr Ser Asp Ala Ile Glu Ala Tyr Lys
        195                 200                 205

Arg Gln Arg Glu Gln Lys Gly Arg Arg Asp Glu Leu Arg Arg Arg Glu
    210                 215                 220

Pro Ala Ser Lys Asp Gln Thr Val Arg Pro Arg Asp Arg Val Ser Asp
225                 230                 235                 240

Glu Asp Ala Glu Gly Glu Ser Asp Ala Glu Trp Asp Asp Gly Asp Arg
                245                 250                 255

Ser Pro Ser Leu Pro Lys Asp Asp Pro Pro Ala Glu Leu Arg Asp Ile
            260                 265                 270

Gln Arg Ala Arg Val Gly Arg Thr Asn Phe Ala Gln Val Cys Phe Tyr
        275                 280                 285

Pro Gly Phe Asp Asp Ala Ile Ser Gly Cys Tyr Ala Arg Val Asn Ile
    290                 295                 300

Gly Pro Asn Arg Glu Thr Gly Gln Asn Glu Tyr Arg Leu Cys Leu Ile
305                 310                 315                 320

Lys Lys Phe Thr Glu Gly Arg Pro Tyr Ser Met Glu Gly Pro Asn Gly
                325                 330                 335

Arg Ser Phe Val Thr Lys Gln Tyr Ala Val Leu Ala His Gly Lys Ala
            340                 345                 350

Glu Arg Glu Phe Pro Phe Val Ala Cys Ser Asp Ser Ala Ile Thr Glu
```

```
        355                 360                 365

Ala Glu Phe Asn Arg Tyr Arg Gln Thr Met Ala Val Glu Asp Cys Lys
    370                 375                 380

Met Ala Thr Lys Ser Thr Val Ala Glu Lys Val Val Asp Ile Asn Arg
385                 390                 395                 400

Leu Leu Asn His Lys Phe Thr Pro Glu Glu Leu Thr Glu Lys Leu Arg
                405                 410                 415

Lys Gln Gly Ser Leu Asp Thr Lys Ser Thr Val Phe Lys Arg Met Glu
            420                 425                 430

Thr Glu Lys Lys Leu Lys Leu Ala Lys Ala Ala Gly Asp Asp Ala Glu
        435                 440                 445

Val Glu Arg Leu Glu Ser Glu Leu Ala Ser Met Ser Thr Pro Lys Leu
    450                 455                 460

Ala Phe Asn Ala Thr Ser Ser Lys Pro Arg Ala Asp Lys Pro Ser Glu
465                 470                 475                 480

His Glu Arg Leu Leu Glu Leu Asn Leu Arg Asn Gln Arg Leu Asn Thr
                485                 490                 495

Glu Asn Val Arg Arg Ala Gln Leu Glu Glu Arg Lys Ala Ser Arg Lys
            500                 505                 510

Ala Ala Ala Ala Val Ala Arg Gly Glu Ala Gln Pro Asn Pro Phe Met
        515                 520                 525

Arg Val Arg Thr His Ala Arg Thr His Tyr Asp Ala Asn Gly Asn Gly
    530                 535                 540

Thr Thr Leu Ser Glu Thr Thr Thr Arg Asp Gly Thr Pro Ala Thr Gly
545                 550                 555                 560

Ser Asp Thr Pro Ser Lys Ala Asn Thr Pro Asn Gly Ser Asn Pro Pro
                565                 570                 575

Ser Gly Ser Gln Lys Lys Thr Thr Lys Gly Gly Val Ala Thr Ile Arg
            580                 585                 590

His Arg Asn Met Asp Asp Glu Asn Ile Ala Ala Leu Asp Leu Asp Leu
        595                 600                 605

Asp Ile Glu Ile
    610


<210> SEQ ID NO 41
<211> LENGTH: 628
<212> TYPE: PRT
<213> ORGANISM: Aspergillus  flavus

<400> SEQUENCE: 41

Met Ala Asp Asp Leu Asp Ala Glu Leu Leu Ala Leu Ala Gly Asp Ala
1               5                   10                  15

Ser Asp Glu Glu Ala Ser Ser Pro Pro Arg Gln Lys Asp Ala Ser Pro
            20                  25                  30

Ser Ala Ser Pro Pro Gln Ser Pro Glu Glu Ser Ser Thr Met Gly Arg
        35                  40                  45

Lys Gly Thr Ala Lys Pro Val Arg Arg Gly Arg Lys Ser Arg Lys Asp
    50                  55                  60

Asp Glu Glu Asp Gly Glu Val Ser Ala Ala Glu Ser His Asn Ser Leu
65                  70                  75                  80

Asp Ser Ala Ser Met Val Glu Ser Glu Ser Gly Ser Asp Ser Glu Gly
                85                  90                  95

Ser Asp Ala Gly Ala Glu Asp Asp Gly Pro Ile Phe Pro Tyr Asp Lys
            100                 105                 110
```

```
Leu Tyr Tyr Ser Ser Lys Asp Lys Glu Glu Ile Met Ala Met Pro Glu
        115                 120                 125

Ile Gln Arg Glu Gln Ile Leu Ser Glu Arg Ala Gln Gln Val Asp Arg
    130                 135                 140

His Asn Gln Asp Leu Ala Leu Arg Arg Leu Leu Ala Ser Arg Glu Arg
145                 150                 155                 160

Glu Glu Ala Arg Gln Ala Lys Lys Asn Lys Arg Lys Ala Ser Met Ala
                165                 170                 175

Asn Leu Glu Asp Gly Gln Arg Lys Ser Ser Arg Gln Lys Thr Thr Leu
            180                 185                 190

Gly Gly Arg Lys Val Gly Glu Thr Ser Asp Ala Ile Glu Ala Tyr Lys
        195                 200                 205

Arg Gln Arg Glu Gln Lys Gly Arg Arg Asp Glu Leu Arg Arg Arg Glu
    210                 215                 220

Pro Ala Ser Lys Asp Gln Thr Val Arg Pro Arg Asp Arg Val Ser Asp
225                 230                 235                 240

Glu Asp Ala Glu Gly Glu Ser Asp Ala Glu Trp Asp Asp Gly Asp Arg
                245                 250                 255

Ser Pro Ser Leu Pro Lys Asp Asp Pro Pro Ala Glu Leu Arg Asp Ile
            260                 265                 270

Gln Arg Ala Arg Val Gly Arg Thr Asn Phe Ala Gln Val Cys Phe Tyr
        275                 280                 285

Pro Gly Phe Asp Asp Ala Ile Ser Gly Cys Tyr Ala Arg Val Asn Ile
    290                 295                 300

Gly Pro Asn Arg Glu Thr Gly Gln Asn Glu Tyr Arg Leu Cys Leu Ile
305                 310                 315                 320

Lys Lys Phe Thr Glu Gly Arg Pro Tyr Ser Met Glu Gly Pro Asn Gly
                325                 330                 335

Arg Ser Phe Val Thr Lys Gln Tyr Ala Val Leu Ala His Gly Lys Ala
            340                 345                 350

Glu Arg Glu Phe Pro Phe Val Ala Cys Ser Asp Ser Ala Ile Thr Glu
        355                 360                 365

Val Cys Phe Ile Phe Leu Pro Ala Asn Pro Leu Ser Asn Thr Val Ala
    370                 375                 380

Ala Glu Phe Asn Arg Tyr Arg Gln Thr Met Ala Val Glu Asp Cys Lys
385                 390                 395                 400

Met Ala Thr Lys Ser Thr Val Ala Glu Lys Val Val Asp Ile Asn Arg
                405                 410                 415

Leu Leu Asn His Lys Phe Thr Pro Glu Glu Leu Thr Glu Lys Leu Arg
            420                 425                 430

Lys Gln Gly Ser Leu Asp Thr Lys Ser Thr Val Phe Lys Arg Met Glu
        435                 440                 445

Thr Glu Lys Lys Leu Lys Leu Ala Lys Ala Ala Gly Asp Asp Ala Glu
    450                 455                 460

Val Glu Arg Leu Glu Ser Glu Leu Ala Ser Met Ser Thr Pro Lys Leu
465                 470                 475                 480

Ala Phe Asn Ala Thr Ser Ser Lys Pro Arg Ala Asp Lys Pro Ser Glu
                485                 490                 495

His Glu Arg Leu Leu Glu Leu Asn Leu Arg Asn Gln Arg Leu Asn Thr
            500                 505                 510

Glu Asn Val Arg Arg Ala Gln Leu Glu Glu Arg Lys Ala Ser Arg Lys
        515                 520                 525

Ala Ala Ala Ala Val Ala Arg Gly Glu Ala Gln Pro Asn Pro Phe Met
```

```
    530                 535                 540

Arg Val Arg Thr His Ala Arg Thr His Tyr Asp Ala Asn Gly Asn Gly
545                 550                 555                 560

Thr Thr Leu Ser Glu Thr Thr Thr Arg Asp Gly Thr Pro Ala Thr Gly
                565                 570                 575

Ser Asp Thr Pro Ser Lys Ala Asn Thr Pro Asn Gly Ser Asn Thr Pro
            580                 585                 590

Ser Gly Ser Gln Lys Lys Thr Thr Lys Gly Gly Val Ala Thr Ile Arg
        595                 600                 605

His Arg Asn Met Asp Asp Glu Asn Ile Ala Ala Leu Asp Leu Asp Leu
    610                 615                 620

Asp Ile Glu Ile
625


<210> SEQ ID NO 42
<211> LENGTH: 607
<212> TYPE: PRT
<213> ORGANISM: Aspergillus  terreus

<400> SEQUENCE: 42

Met Ala Asp Asp Leu Asp Ala Glu Leu Leu Ala Leu Ala Gly Asp Ser
1               5                   10                  15

Asp Glu Glu Ser Ser Pro Pro Ser Lys Gln Lys Pro Thr Ser Pro Ser
            20                  25                  30

Ala Ser Pro Asp Pro His Ser Pro Glu Pro Ser Ser Ala Thr Met Gly
        35                  40                  45

Arg Lys Gly Thr Ala Lys Pro Val Arg Arg Gly Arg Lys Val Arg Arg
    50                  55                  60

Ala Pro Glu Glu Asp Gly Glu Leu Ser Ala Ala Glu Ser His His Ser
65                  70                  75                  80

Leu Asp Ser Ala Ser Met Ser Glu Ser Glu Ala Ala Ser Asp Ser Glu
                85                  90                  95

Gly Ser Ala His Gly Glu Asp Glu Gly Pro Ile Phe Pro Tyr Asp Lys
            100                 105                 110

Leu Tyr Tyr Ser Ala Lys Asp Lys Glu Glu Ile Met Ala Met Pro Glu
        115                 120                 125

Ile Gln Arg Glu Gln Ile Leu Ser Glu Arg Ala Gln Glu Val Asp Arg
    130                 135                 140

His Asn Gln Asp Leu Ala Leu Arg Arg Leu Leu Ala Ser Arg Glu Arg
145                 150                 155                 160

Glu Glu Ala Arg Gln Ala Lys Lys Asn Lys Arg Lys Ala Ser Met Ala
                165                 170                 175

Asn Leu Glu Asp Gly Asn Arg Lys Ser Ser Arg Gln Lys Thr Thr Leu
            180                 185                 190

Gly Gly Arg Lys Val Gly Glu Thr Ser Asp Ala Ile Glu Ala Tyr Lys
        195                 200                 205

Arg Gln Arg Glu Gln Lys Gly Lys Arg Asp Glu Leu Arg Arg Arg Glu
    210                 215                 220

Pro Ala Val Lys Glu Lys Ser Arg Thr Arg Asp Glu Leu Ser Asp Glu
225                 230                 235                 240

Asp Ala Glu Gly Glu Ser Asp Ala Glu Trp Asp Glu Gly Glu Arg Ser
                245                 250                 255

Pro Ser Pro Pro Lys Asp Asp Pro Pro Ala Glu Leu Arg Asp Ile Gln
            260                 265                 270
```

```
Arg Ala Arg Val Gly Arg Ser Asn Phe Ala Gln Val Cys Phe Tyr Pro
        275                 280                 285

Gly Phe Asp Glu Ala Ile Ser Gly Cys Tyr Ala Arg Val Asn Ile Gly
    290                 295                 300

Pro Asn Arg Asp Thr Gly Gln Asn Glu Tyr Arg Leu Cys Leu Ile Lys
305                 310                 315                 320

Lys Phe Thr Glu Gly Arg Pro Tyr Ser Met Glu Gly Pro Asn Gly Arg
                325                 330                 335

Ser Phe Val Thr Asn Gln Tyr Ala Val Leu Ala His Gly Lys Ala Glu
            340                 345                 350

Arg Glu Phe Pro Phe Ile Ala Cys Ser Asp Ser Pro Phe Thr Glu Ala
        355                 360                 365

Glu Phe Asn Arg Tyr Arg Gln Thr Met Ala Val Glu Asp Cys Lys Ile
    370                 375                 380

Ala Thr Lys Ser Val Leu Ala Glu Lys Val Ala Asp Ile Asn Arg Leu
385                 390                 395                 400

Leu Asn His Lys Phe Thr Lys Glu Glu Leu Asn Glu Lys Leu Arg Lys
                405                 410                 415

Gln Gly Ser Phe Asp Thr Lys Ala Met Phe Phe Lys Arg Val Glu Leu
            420                 425                 430

Glu Arg Gln Ile Lys Leu Ala Lys Ala Ala Gly Glu Asp Ala Glu Val
        435                 440                 445

Glu Lys Leu Glu Glu Glu Leu Arg Ser Leu Ser Thr Pro Lys Leu Ala
    450                 455                 460

Phe Ser Ser Gly Ser Ser Lys Pro Arg Pro Ser Gln Thr Ser Glu His
465                 470                 475                 480

Glu Arg Leu Leu Glu Leu Asn Leu Arg Asn Gln Lys Leu Asn Tyr Glu
                485                 490                 495

Asn Val Arg Arg Ala Gln Leu Glu Glu Arg Arg Ala Gly Arg Lys Ala
            500                 505                 510

Ala Ala Ala Val Ala Arg Gly Glu Ala Ala Ala Asn Pro Phe Leu Arg
        515                 520                 525

Val Arg Thr His Ala Arg Thr His Tyr Asp Ala Asn Gly Asn Ser Leu
    530                 535                 540

Thr Pro Lys Ser Glu Asp Thr Gly Ala Ser Arg Asp Gly Thr Pro Gly
545                 550                 555                 560

Thr Gly Pro Asn Thr Pro Gln Arg Ser Asn Thr Pro Ser Ser Ser Gln
                565                 570                 575

Lys Lys Thr Lys Ser Gly Ala Val Ser Ile Arg His Arg Asn Met Asp
            580                 585                 590

Asp Glu Asn Ile Ala Ala Leu Asp Leu Asp Leu Asp Ile Glu Ile
        595                 600                 605


<210> SEQ ID NO 43
<211> LENGTH: 605
<212> TYPE: PRT
<213> ORGANISM: Aspergillus clavatus

<400> SEQUENCE: 43

Met Ala Asp Glu Leu Asp Ala Glu Leu Leu Ala Leu Ala Gly Asp Ser
1               5                   10                  15

Ser Asp Glu Glu Ser Ser Pro Pro Pro Lys Gln Lys Ser Glu Ser Pro
            20                  25                  30

Ala Pro Ser Ala Ser Pro Ser Ser Ser Met Ala Arg Lys Gly Val Ala
        35                  40                  45
```

```
Lys Pro Val Arg Arg Asn Lys Lys Ser Arg Arg Asp Asp Glu Glu Asp
    50                  55                  60

Gly Glu Val Ser Asp Ala Gly Ser His His Ser Leu Glu Ser Ala Ser
65                  70                  75                  80

Met Ser Glu Ser Glu Ala Ala Ser Asp Ser Glu Gly Ser Ser Glu Gly
                85                  90                  95

Gly Asp Glu Asp Arg Pro Ile Phe Pro Tyr Glu Lys Leu Tyr Tyr Ser
            100                 105                 110

Ala Lys Asp Lys Glu Glu Ile Met Ala Met Pro Glu Ile Gln Arg Glu
        115                 120                 125

Gln Ile Leu Ser Glu Arg Ala Gln Glu Val Asp Arg Arg Asn Gln Asp
    130                 135                 140

Leu Ala Leu Arg Arg Leu Leu Ala Ser Arg Glu Arg Asp Glu Ala Arg
145                 150                 155                 160

Arg Val Lys Lys Ser Lys Arg Lys Ala Ser Val Ala Asp Leu Glu Glu
                165                 170                 175

Gly Gln Arg Lys Ser Ser Arg Gln Lys Thr Thr Leu Gly Gly Arg Lys
            180                 185                 190

Val Gly Glu Ala Ser Glu Ala Ile Glu Ala Tyr Lys Arg Gln Arg Glu
        195                 200                 205

Lys Lys Gly Lys Arg Asp Glu Leu Arg Arg Arg Glu Thr Ala Thr Gly
    210                 215                 220

Asp Gln Ala Thr Pro Lys Asp Glu Gly Pro Ser Asp Lys Asp Ala Asp
225                 230                 235                 240

Gly Glu Ser Glu Val Glu Trp Asp Asn Arg Glu Arg Ser Pro Ser Leu
                245                 250                 255

Pro Lys Asp Asp Pro Pro Ala Glu Leu Arg Asp Ile Gln Arg Ala Arg
            260                 265                 270

Val Gly Arg Thr Asn Phe Ala Gln Val Cys Phe Tyr Pro Arg Phe Asp
        275                 280                 285

Glu Cys Ile Ser Gly Cys Tyr Ala Arg Val Asn Ile Gly Pro Asn Arg
    290                 295                 300

Asp Ser Gly Asn Asn Glu Tyr Arg Leu Cys Leu Ile Lys Arg Phe Thr
305                 310                 315                 320

Val Gly Arg Pro Tyr Ala Met Glu Gly Pro Asn Gly Arg Ser Phe Val
                325                 330                 335

Thr Asn Gln Tyr Ala Val Leu Ala His Gly Lys Ala Glu Arg Glu Phe
            340                 345                 350

Pro Phe Val Ala Cys Ser Asp Ser Pro Phe Thr Glu Ala Glu Phe Ser
        355                 360                 365

Arg Tyr Arg Gln Thr Met Ala Val Glu Asp Cys Lys Ile Ala Thr Lys
    370                 375                 380

Ser Thr Leu Ala Glu Lys Val Ala Asp Ile Asn Arg Leu Leu Asn His
385                 390                 395                 400

Gln Phe Thr Lys Glu Glu Leu Asn Glu Lys Leu Arg Lys Gln Gly Ser
                405                 410                 415

Leu Asp Asn Lys Met Arg Thr Phe Lys Arg Leu Glu Thr Glu Lys Gln
            420                 425                 430

Leu Lys Leu Ala Arg Ala Ala Gly Asp Asp Glu Glu Val Ser Lys Leu
        435                 440                 445

Glu Lys Glu Leu Ala Glu Leu Ala Gly Pro Lys Leu Ala Val Ser Ser
    450                 455                 460
```

-continued

His Asn Ala Arg Pro Arg Ser Lys Lys Pro Ser Asp Tyr Glu Arg Leu
465 470 475 480

Ala Glu Leu Asn Phe Arg Asn Gln Lys Leu Asn Thr Glu Ser Val Arg
485 490 495

Arg Ala Gln Leu Glu Glu Arg Arg Ala Asn Arg Lys Ala Ala Ala Ala
500 505 510

Val Ala Arg Gly Glu Ala Gln Ala Asn Pro Phe Met Arg Val Arg Thr
515 520 525

Leu Ala Arg Thr His Tyr Asp Ala Asn Gly Asn Ser Leu Thr Pro Asp
530 535 540

Ser Thr Ala Ser Arg Asn Glu Thr Pro Ala Thr Ala Ser Glu Thr Pro
545 550 555 560

Ser Lys Ala Gly Thr Pro Lys Pro Thr Gly His Val Gln Lys Lys Gln
565 570 575

Ser Lys Gly Gly Val Ala Thr Ile Arg His Arg Asn Met Asp Asp Glu
580 585 590

Asn Ile Ala Ala Leu Asp Leu Asp Ile Asp Ile Glu Ile
595 600 605

<210> SEQ ID NO 44
<211> LENGTH: 558
<212> TYPE: PRT
<213> ORGANISM: Saccharomyces cerevisiae

<400> SEQUENCE: 44

Met Ser Asp Leu Asp Glu Asp Leu Leu Ala Leu Ala Gly Ala Asp Glu
1 5 10 15

Ser Glu Glu Glu Asp Gln Val Leu Thr Thr Thr Ser Ala Lys Arg Ala
20 25 30

Lys Asn Asn Asp Gln Ser Leu Ser Lys Lys Arg Arg Ile Glu Val Gly
35 40 45

Ser Val Glu Asp Asp Asp Glu Glu Asp Asp Tyr Asn Pro Tyr Ser Val
50 55 60

Gly Asn Ala Asp Tyr Gly Ser Glu Glu Glu Glu Glu Ala Asn Pro Phe
65 70 75 80

Pro Leu Glu Gly Lys Tyr Lys Asp Glu Ser Asp Arg Glu His Leu Glu
85 90 95

Ser Leu Pro Glu Met Glu Arg Glu Thr Leu Leu Phe Glu Arg Ser Gln
100 105 110

Ile Met Gln Lys Tyr Gln Glu Arg Lys Leu Phe Arg Glu Arg Gly Arg
115 120 125

Asp Met Lys Glu Gln Gln Gln Arg Ala Lys Asn Asp Glu Asp Ser Arg
130 135 140

Lys Thr Arg Ala Ser Thr Arg Ser Thr His Ala Thr Gly His Ser Asp
145 150 155 160

Ile Lys Ala Ser Lys Leu Ser Gln Leu Lys Lys Gln Arg Ala Arg Lys
165 170 175

Asn Arg His Tyr Ser Asp Asn Glu Asp Glu Asp Asp Glu Glu Asp Tyr
180 185 190

Arg Glu Glu Asp Tyr Lys Asp Asp Glu Gly Ser Glu Tyr Gly Asp Asp
195 200 205

Glu Glu Tyr Asn Pro Phe Asp Arg Arg Asp Thr Tyr Asp Lys Arg Glu
210 215 220

Glu Val Glu Trp Ala Glu Glu Glu Asp Glu Gln Asp Arg Glu Pro Glu
225 230 235 240

```
Ile Ser Asp Phe Asn Lys Leu Arg Ile Gly Arg Ser Phe Val Ala Lys
                245                 250                 255

Phe Cys Phe Tyr Pro Gly Phe Glu Asp Ala Val Lys Gly Cys Tyr Gly
            260                 265                 270

Arg Val Asn Val Gly Thr Asp Lys Arg Thr Gly Lys Thr Ser Tyr Arg
        275                 280                 285

Met Val Arg Ile Glu Arg Val Phe Leu Gln Lys Pro Tyr Asn Met Gly
    290                 295                 300

Lys Phe Tyr Thr Asn Gln Tyr Phe Gly Val Thr Gln Gly Lys Asp Arg
305                 310                 315                 320

Lys Val Phe Gln Met Asn Tyr Phe Ser Asp Gly Leu Phe Ala Glu Asp
                325                 330                 335

Glu Tyr Gln Arg Tyr Leu Arg Ala Leu Asp Asn Ser Gln Met Ile Lys
            340                 345                 350

Pro Ser Leu His Ser Leu Ser Asn Lys Thr Lys Glu Val Met Asp Phe
        355                 360                 365

Val Asn Thr Pro Leu Thr Asp Lys Thr Thr Asp Glu Val Val Arg His
    370                 375                 380

Arg Met Gln Phe Asn Lys Lys Leu Ser Gly Thr Asn Ala Val Leu Glu
385                 390                 395                 400

Lys Thr Val Leu Arg Glu Lys Leu Gln Tyr Ala Lys Glu Thr Asn Asn
                405                 410                 415

Glu Lys Asp Ile Ala Lys Tyr Ser Ala Gln Leu Arg Asn Phe Glu Lys
            420                 425                 430

Arg Met Ser Val Tyr Glu Lys His His Glu Asn Asp Gln Ser Asp Ile
        435                 440                 445

Lys Lys Leu Gly Glu Leu Thr Ser Lys Asn Arg Lys Leu Asn Met Ser
    450                 455                 460

Asn Ile Arg Asn Ala Glu His Val Lys Lys Glu Asp Ser Asn Asn Phe
465                 470                 475                 480

Asp Ser Lys Ser Asp Pro Phe Ser Arg Leu Lys Thr Arg Thr Lys Val
                485                 490                 495

Tyr Tyr Gln Glu Ile Gln Lys Glu Glu Asn Ala Lys Ala Lys Glu Ile
            500                 505                 510

Ala Gln Gln Glu Lys Leu Gln Glu Asp Lys Asp Ala Lys Asp Lys Arg
        515                 520                 525

Glu Lys Glu Leu Leu Val Ala Gln Phe Arg Arg Leu Gly Gly Leu Glu
    530                 535                 540

Arg Met Val Gly Glu Leu Asp Ile Lys Phe Asp Leu Lys Phe
545                 550                 555


<210> SEQ ID NO 45
<211> LENGTH: 311
<212> TYPE: PRT
<213> ORGANISM: Aspergillus nidulans

<400> SEQUENCE: 45

Met Asp Leu Ala Asn Leu Ile Ser Gln Pro Gly Pro Glu Pro Ala Leu
1               5                   10                  15

Thr Ala Lys Ser Arg Tyr Ser Pro Pro Ala Phe Glu Pro Gly Ser Phe
            20                  25                  30

Tyr Ala Ala Ser Thr Ser Phe Thr Arg Thr Gln Ala Pro Leu Ser Pro
        35                  40                  45

Pro Val Glu Asp Arg Ser Ser Arg Cys Ser Leu Pro Ser Ile Ser Ala
```

```
    50                  55                  60

Leu Leu Asp Ser Ala Asp Gly Ala Ser Thr Gln Ala Pro Lys Arg Gln
65                  70                  75                  80

Arg Leu Ser Ser Pro Met His Arg Glu Pro Leu Asp Lys Asn Pro Ser
                85                  90                  95

Ala Gly Ala Ala Pro Ile Arg Leu Pro Pro Thr Pro Pro Leu Arg Pro
            100                 105                 110

Gly Ser Gly Phe His Ser Ala Gly His Ser Pro Ser Ser Ser Ile Ser
        115                 120                 125

Ser Ile Ser Met Ile Lys Ser Glu Tyr Pro Ala Pro Pro Ser Ala Pro
    130                 135                 140

Val Ser Leu Pro Gly Leu Pro Ser Pro Thr Asp Arg Ser Ser Ile Ser
145                 150                 155                 160

Ser Gln Gly Ser Ala Pro Gln His Gln His Gly Pro Tyr Ala Ser Pro
                165                 170                 175

Ala Pro Ser Val Ala Pro Ser Tyr Ser Ser Pro Val Glu Pro Ser Pro
            180                 185                 190

Ser Ser Ala Met Tyr Tyr Gln His Gln Arg Pro Ala Ser Ser Gly Thr
        195                 200                 205

Tyr Gln Ala Pro Pro Pro Pro Pro Gln His Gln Pro Met Ile Ser Pro
    210                 215                 220

Val Thr Pro Ala Trp Gln His His His Tyr Phe Pro Pro Ser Ser Asn
225                 230                 235                 240

Thr Pro Tyr Gln Gln Asn His Asp Arg Tyr Ile Cys Arg Thr Cys His
                245                 250                 255

Lys Ala Phe Ser Arg Pro Ser Ser Leu Arg Ile His Ser His Ser His
            260                 265                 270

Thr Gly Glu Lys Pro Phe Arg Cys Thr His Ala Gly Cys Gly Lys Ala
        275                 280                 285

Phe Ser Val Arg Ser Asn Met Lys Arg His Glu Arg Gly Cys His Thr
    290                 295                 300

Gly Arg Ala Val Ala Met Val
305                 310


<210> SEQ ID NO 46
<211> LENGTH: 319
<212> TYPE: PRT
<213> ORGANISM: Aspergillus terreus

<400> SEQUENCE: 46

Met Asp Leu Ala Ser Leu Ile Thr Pro Gly Pro Thr Pro Phe Ala Ser
1               5                   10                  15

Arg Pro Pro Arg Ala Ser Tyr Ser Pro Pro Ala Ser Ser Ser Gly Ser
            20                  25                  30

Tyr Lys Ala Pro Asn Glu Pro His Tyr Thr Gly Ser Tyr Phe Pro Ala
        35                  40                  45

Met Pro Thr Ala Thr Pro Val Thr Thr Thr Thr Ser Tyr Ser Arg Ser
    50                  55                  60

Pro Gln Pro Pro Leu Ser Pro Pro Val Glu Asp Gln Pro Lys Cys Ser
65                  70                  75                  80

Leu Pro Ser Ile Ser Thr Leu Leu Gly Ala Ala Asp Ser Ala Pro Met
                85                  90                  95

Pro Pro Ala Lys Arg Gln Arg Leu Ser Thr Pro Ala Arg Arg Glu Ser
            100                 105                 110
```

```
Asp Ser Trp Leu Gln Thr Thr Pro Cys Leu Pro Pro Thr Pro Pro Leu
        115                 120                 125

Arg Pro Gly Ser Gly Phe His Ser Ser Gly His Arg Ser Pro Ser Ser
    130                 135                 140

Asn Lys Pro Thr Glu Ser Ala Pro Phe Pro Gln Gln Pro Pro Val Thr
145                 150                 155                 160

Leu Pro Ser Pro Thr Glu Arg Ser Ser Ile Ser Ser Gln Gly Ser Ala
                165                 170                 175

His Ala Pro Tyr Ala Ser Pro Ala Pro Ser Val Ala Ser Tyr Ser Ser
            180                 185                 190

Pro Val Glu Pro Ser Pro Ala Pro Ser Thr Leu Tyr Tyr Gln Arg Pro
        195                 200                 205

Ala Ala Pro Pro Ala Pro Ser Ala Ala Ala Ala Ala Pro Ala Pro Ala
    210                 215                 220

Gln Pro Leu Ile Ser Pro Val Thr Pro Ala Trp Gln His His His Tyr
225                 230                 235                 240

Phe Pro Pro Ser Ser Ser Thr Pro Tyr Gln Gln Asn His Asp Arg Tyr
                245                 250                 255

Ile Cys Arg Thr Cys His Lys Ala Phe Ser Arg Pro Ser Ser Leu Arg
            260                 265                 270

Ile His Ser His Ser His Thr Gly Glu Lys Pro Phe Arg Cys Thr His
        275                 280                 285

Ala Gly Cys Gly Lys Ala Phe Ser Val Arg Ser Asn Met Lys Arg His
    290                 295                 300

Glu Arg Gly Cys His Ser Gly Arg Pro Val Ala Thr Ala Met Val
305                 310                 315


<210> SEQ ID NO 47
<211> LENGTH: 319
<212> TYPE: PRT
<213> ORGANISM: Aspergillus flavus

<400> SEQUENCE: 47

Met Asp Leu Ala Ser Leu Ile Thr Pro Gly Pro Glu Pro Ile Tyr Lys
1               5                   10                  15

Ser Arg Ala Ser Tyr Ser Pro Pro Pro Ser Ser Ala Gly Ser Tyr Lys
            20                  25                  30

Arg Pro Ala Glu His Asp Ser Tyr Phe Ser Tyr Ser Arg Ala Pro Gln
        35                  40                  45

Ala Pro Leu Ser Pro Pro Val Glu Asp Gln Pro Lys Cys Ser Leu Pro
    50                  55                  60

Ser Ile Ser Thr Leu Leu Glu Gly Ala Asp Ser Ala Ser Thr Tyr Ala
65                  70                  75                  80

Ala Lys Arg Gln Arg Thr Ser Pro Pro Pro Arg Arg Glu Ser Glu Phe
                85                  90                  95

Arg Ser Pro Tyr Asp Ser Val Ser Thr Pro Asn Gly Pro Pro Thr Pro
            100                 105                 110

Pro Leu Arg Pro Glu Ser Gly Phe His Ser Gly His His Ser Pro Ser
        115                 120                 125

Ala Ser Ser Val Thr Ser Gly Lys Ala Ile Lys Leu Glu Ser Tyr Ser
    130                 135                 140

Gln Thr Pro Met Thr Leu Pro Ser Pro Ser Asp Arg Ser Ser Ile Ser
145                 150                 155                 160

Ser Gln Gly Ser Val His His Val Ser Ala Ala Pro Tyr Ala Ser Pro
                165                 170                 175
```

```
Ala Pro Ser Val Ala Ser Tyr Ser Ser Pro Val Glu Ser Ser Ala Pro
            180                 185                 190

Ser Ala Met Tyr Tyr Gln Arg Pro Ser Gly Ser Tyr Gln Thr Pro Ala
        195                 200                 205

Thr Val Pro Ser Pro Ser Ala Ala Pro Met Pro Ala Ser Ala Thr His
    210                 215                 220

Gln Gln Met Ile Thr Pro Val Thr Pro Ala Trp Gln His His His Tyr
225                 230                 235                 240

Phe Pro Pro Ser Ser Ser Ala Pro Tyr Gln Gln Asn His Asp Arg Tyr
                245                 250                 255

Ile Cys Arg Thr Cys His Lys Ala Phe Ser Arg Pro Ser Ser Leu Arg
            260                 265                 270

Ile His Ser His Ser His Thr Gly Glu Lys Pro Phe Arg Cys Thr His
        275                 280                 285

Ala Gly Cys Gly Lys Ala Phe Ser Val Arg Ser Asn Met Lys Arg His
    290                 295                 300

Glu Arg Gly Cys His Thr Gly Arg Pro Val Ala Thr Ala Met Val
305                 310                 315


<210> SEQ ID NO 48
<211> LENGTH: 335
<212> TYPE: PRT
<213> ORGANISM: Aspergillus clavatus

<400> SEQUENCE: 48

Met Asp Leu Ala Asn Leu Ile Ser His Pro Thr Ser Glu Ala Ala Ser
1               5                   10                  15

Thr Phe Lys Ser Arg Ser Ala Gln Ser Pro Pro Ala Phe Gln Ala Asn
            20                  25                  30

Pro Tyr Lys Arg Leu Ser Gly Ser Ser Met Ser Ser Tyr Phe Thr Ser
        35                  40                  45

Val Pro Thr Thr Ala Thr Ser Tyr Ser Arg Thr Pro Gln Pro Pro Leu
    50                  55                  60

Ser Pro Pro Val Asp Asp Arg Pro Arg Cys Ser Leu Pro Ser Ile Ser
65                  70                  75                  80

Thr Leu Leu Glu Gly Ala Asp Ser Ala Ala Ala His Ala Ala Lys Arg
                85                  90                  95

Gln Arg Thr Ser Leu Ser Ala His Arg Asp Leu Asp Ala Arg Pro Gln
            100                 105                 110

Ser Gln Pro Tyr Asp Thr Ile Thr Pro His Ala Leu Pro Pro Thr Pro
        115                 120                 125

Pro Leu Arg Pro Gly Ser Gly Phe Arg Ser Asn Gly His Ser Pro Ser
    130                 135                 140

Ala Ser Ser Val Ser Ala Thr Ser Ala Ser Thr Val Ile Lys Thr Glu
145                 150                 155                 160

Thr Tyr Pro Gln Pro His Ile Gly Leu Pro Ser Pro Thr Asp Arg Ser
                165                 170                 175

Ser Ile Ser Ser Gln Gly Ser Val Gln His Ala Pro Gly Ala Pro Tyr
            180                 185                 190

Ala Ser Pro Ala Pro Ser Val Ala Ser Tyr Ser Ser Pro Val Glu Pro
        195                 200                 205

Ser Thr Pro Ser Ser Ala Ala Tyr Tyr Gln Arg Lys Ala Pro Ser Ala
    210                 215                 220

Pro Phe Gln Asn Pro Gly Ser Val Pro Ser Ala Ser Ala Ala His Gln
```

```
225                 230                 235                 240

Gln Leu Ile Thr Pro Ile Thr Pro Ala Trp Gln His His His Tyr Phe
                245                 250                 255

Pro Pro Ser Ser Ser Thr Ala Tyr Gln Gln Asn His Asp Arg Tyr Ile
            260                 265                 270

Cys Arg Thr Cys His Lys Ala Phe Ser Arg Pro Ser Ser Leu Arg Ile
        275                 280                 285

His Ser His Ser His Thr Gly Glu Lys Pro Phe Arg Cys Thr His Ala
    290                 295                 300

Gly Cys Gly Lys Ala Phe Ser Val Arg Ser Asn Met Lys Arg His Glu
305                 310                 315                 320

Arg Gly Cys His Thr Gly Arg Pro Val Ala Thr Ala Met Val Ser
                325                 330                 335


<210> SEQ ID NO 49
<211> LENGTH: 336
<212> TYPE: PRT
<213> ORGANISM: Aspergillus fumigatus

<400> SEQUENCE: 49

Met Asp Val Ala Ser Leu Ile Ser Pro Ser Glu Ser Asp Thr Val Pro
1               5                   10                  15

Thr Phe Arg Ser Arg Ser Ile Gln Asn Ser Ser Ala Ser His Tyr Lys
            20                  25                  30

Arg Leu Ser Glu Gln Ser Thr Gly Ser Tyr Phe Ser Ala Val Pro Thr
        35                  40                  45

His Thr Thr Ser Tyr Ser Arg Thr Pro Gln Pro Pro Leu Ser Pro Pro
    50                  55                  60

Ala Glu Asp Gln Ser Lys Cys Ser Leu Pro Ser Ile Ser Ile Leu Leu
65                  70                  75                  80

Glu Asn Ala Asp Gly Ala Ala Ala His Ala Ala Lys Arg Gln Arg Asn
                85                  90                  95

Ser Leu Ser Thr His Arg Asp Ser Asp Pro Arg Pro Pro Tyr Asp Ser
            100                 105                 110

Ile Thr Pro His Ala Met Pro Pro Thr Pro Pro Leu Arg Pro Gly Ser
        115                 120                 125

Gly Phe His Ser Asn Gly His Ser Pro Ser Thr Ser Ser Val Ser Ala
    130                 135                 140

Ala Ser Ser Ser Ala Leu Met Lys Asn Thr Glu Ser Tyr Pro Gln Ala
145                 150                 155                 160

Pro Ile Gly Leu Pro Ser Pro Thr Asp Arg Ser Ser Ile Ser Ser Gln
                165                 170                 175

Gly Ser Val Gln His Ala Ala Ser Ala Pro Tyr Ala Ser Pro Ala Pro
            180                 185                 190

Ser Val Ser Ser Phe Ser Ser Pro Ile Glu Pro Ser Thr Pro Ser Thr
        195                 200                 205

Ala Ala Tyr Tyr Gln Arg Asn Pro Ala Pro Asn Thr Phe Gln Asn Pro
    210                 215                 220

Ser Pro Phe Pro Gln Thr Ser Thr Ala Ser Leu Pro Ser Pro Gly His
225                 230                 235                 240

Gln Gln Met Ile Ser Pro Val Thr Pro Ala Trp Gln His His His Tyr
                245                 250                 255

Phe Pro Pro Ser Ser Ser Thr Ser Tyr Gln Gln Asn His Asp Arg Tyr
            260                 265                 270
```

-continued

```
Ile Cys Arg Thr Cys His Lys Ala Phe Ser Arg Pro Ser Ser Leu Arg
        275                 280                 285

Ile His Ser His Ser His Thr Gly Glu Lys Pro Phe Arg Cys Thr His
    290                 295                 300

Ala Gly Cys Gly Lys Ala Phe Ser Val Arg Ser Asn Met Lys Arg His
305                 310                 315                 320

Glu Arg Gly Cys His Thr Gly Arg Pro Val Ala Thr Ala Met Val Gln
                325                 330                 335
```